US007687608B2

(12) United States Patent
Lancaster et al.

(10) Patent No.: US 7,687,608 B2
(45) Date of Patent: Mar. 30, 2010

(54) METHODS FOR REDUCING THE MITOGENICITY OF LECTIN COMPOSITIONS

(75) Inventors: Thomas M. Lancaster, Stoneham, MA (US); Wenyi Cai, Somerville, MA (US); Ryan Faucette, Somerville, MA (US); Matthew Pecukonis, Salem, MA (US); Todd C. Zion, Marblehead, MA (US)

(73) Assignee: SmartCells, Inc., Berverly, MA (US)

( * ) Notice: Subject to any disclaimer, the term of this patent is extended or adjusted under 35 U.S.C. 154(b) by 0 days.

(21) Appl. No.: 11/583,993

(22) Filed: Oct. 19, 2006

(65) Prior Publication Data

US 2007/0110811 A1 May 17, 2007

Related U.S. Application Data

(60) Provisional application No. 60/728,652, filed on Oct. 19, 2005.

(51) Int. Cl.
*C07K 16/00* (2006.01)
*A61K 6/14* (2006.01)
*A61K 35/00* (2006.01)
*G01N 33/53* (2006.01)

(52) U.S. Cl. .......................... 530/396; 525/54.1; 514/3; 424/486; 424/124; 424/9.35; 436/827

(58) Field of Classification Search ....................... None
See application file for complete search history.

(56) References Cited

U.S. PATENT DOCUMENTS

| | | | | |
|---|---|---|---|---|
| 4,002,531 | A | 1/1977 | Royer | |
| 4,145,410 | A | 3/1979 | Sears | |
| 4,348,387 | A | 9/1982 | Brownlee et al. | |
| 4,478,746 | A * | 10/1984 | Kim et al. | 530/303 |
| 4,766,106 | A | 8/1988 | Katre et al. | |
| 5,284,934 | A | 2/1994 | Allen | |
| 5,349,052 | A | 9/1994 | Delgado et al. | |
| 5,612,460 | A | 3/1997 | Zalipsky | |
| 5,672,662 | A * | 9/1997 | Harris et al. | 525/408 |
| 5,814,449 | A | 9/1998 | Schultz et al. | |
| 5,830,506 | A | 11/1998 | Taylor | |
| 5,902,603 | A | 5/1999 | Chen et al. | |
| 5,902,607 | A | 5/1999 | Taylor | |
| 6,063,116 | A | 5/2000 | Kelleher | |
| 6,210,306 | B1 | 4/2001 | Miller | |
| 6,267,002 | B1 | 7/2001 | Ehwald et al. | |
| 6,410,053 | B1 | 6/2002 | Taylor | |
| 6,413,494 | B1 | 7/2002 | Lee et al. | |
| 6,454,710 | B1 | 9/2002 | Ballerstadt et al. | |
| 6,477,891 | B2 | 11/2002 | Ehwald et al. | |
| 6,671,527 | B2 | 12/2003 | Petersson et al. | |
| 6,673,596 | B1 | 1/2004 | Sayler et al. | |
| 6,938,463 | B2 | 9/2005 | Ehwald et al. | |
| 2002/0054884 | A1 | 5/2002 | Peetermans et al. | |
| 2002/0168409 | A1 | 11/2002 | Taylor | |
| 2004/0043446 | A1 | 3/2004 | DeFrees et al. | |
| 2004/0202719 | A1 * | 10/2004 | Zion et al. | 424/489 |
| 2006/0067917 | A1 * | 3/2006 | Sambanis et al. | 424/93.7 |

FOREIGN PATENT DOCUMENTS

| | | | |
|---|---|---|---|
| EP | 0626862 | B1 | 9/1999 |
| EP | 0706401 | B1 | 11/2002 |
| WO | WO-93/13803 | | 7/1993 |
| WO | WO-95/01186 | | 1/1995 |
| WO | WO-95/06058 | | 3/1995 |
| WO | WO-98/32466 | | 7/1998 |
| WO | WO 2005/051987 | | 6/2005 |

OTHER PUBLICATIONS

Mourao et al, Isolation and partial characterization of heterophyllin, a new lectin from Artocarpus heterophyllus seeds, Acta Farmaceutica Bonaerense, (Jan.-Mar. 1999) vol. 18, No. 1, pp. 41-47.*

Agrawal et al., "Protein-Carbohydrate Interaction. XVIII. The Preparation and Properties of Acetylated Concanavalin A, the Hemagglutinin of the Jack Bean", *Biochemistry*, 7:4211-18, 1968.

Allen et al., "Binding of Rat and Human Surfactant Proteins A and D to Aspergillus Fumigatus Conidia", *Infection and Immunity*, 67(9): 4563-4569, 1999.

Armstrong et al., "Dextran-linked insulin: a soluble high molecular weight derivative with biological activity in vivo and in vitro", *Biochem. Biophys. Res. Commun*., 47: 354, 1972.

Ballerstadt et al., "Competitive-binding assay method based of fluorescence quenching of ligands held in close proximity by a multivalent receptor", *Anal. Chim. Acta*., 345: 203-12, 1997.

Baudys et al., "Extending Insulin Action in Vivo by Conjugation to Carboxymethyl Dextran", *Bioconjugate Chem*., 9: 176-183, 1998.

De Jong, et al. "Physically Crosslinked Dextran Hydrogels by Stereocomplex Formation of Lactic Acid Oligomers: Degradation and Protein Release Behavior", *Journal of Controlled Release*, 71: 261-275, 2001.

Dillman et al., "Preclinical Trials with Combinations and Conjugates of T101 Monoclonal Antibody and Doxorubicin", *Cancer Research*, 46:4886-4891, 1986.

Dumestre-Perard et al., "Evaluation and Clinical Interest of Mannan Binding Lectin Function in Human Plasma", *Molecular Immunology*, 39: 465-473, 2002.

Eda et al., "Characterization of Truncated Human Mannan-Binding Protein (MBP) Expressed in *Escherichia coli", Biosci. Biotechnol. Biochem*., 62(7): 1326-1331, 1998.

Eda, et al., "Recombinant bovine conglutinin, lacking the N-terminal and collagenous domains, has less conglutination activity but is able to inhibit haemagglutination by influenza A virus", *Biochem J*., 316:43-48, 1996.

(Continued)

*Primary Examiner*—Christopher R Tate
*Assistant Examiner*—Qiuwen Mi
(74) *Attorney, Agent, or Firm*—Choate, Hall & Stewart LLP

(57) ABSTRACT

Methods for reducing the T-cell mitogenicity of lectin compositions are provided. In one aspect this is achieved by chemically modifying mitogenic lectin compositions under optimized conditions. Additionally or alternatively, the reduction in T-cell mitogenicity is achieved by removing unmodified subunits chemically modified mixtures. Modified lectin compositions with reduced T-cell mitogenicity are also provided as are uses of the inventive compositions.

11 Claims, 22 Drawing Sheets

OTHER PUBLICATIONS

Eda et al., "Structure of a truncated human surfactant protein D is less effective in agglutinating bacteria than the native structure and fails to inhibit haemagglutination by influenza A virus", *Biochem J.*, 323:393-399, 1997.

Engel et al., "The Crystal Structure of Dipeptidyl Peptidase IV (CD26) Reveals is Functional Regulation and Enzymatic Mechanism", *PNAS*, 100(9): 5063-5068,2003.

Gunther et al., "Concanavalin A Derivatives with Altered Biological Activities", *Proc. Natl. Acad. Sci. USA*, 70: 1012-6, 1973.

Halestrap et al., "The Proton Linked Monocarboxylate Transporter (MCT) Family: Structure, Function and Regulation", *Biochem. J.*, 343: 281-299, 1999.

Harada et al., "Determinants for the Drug Release from T-0128, Camptothecin Analogue-Carboxymethyl Dextran Conjugate", *Journal of Controlled Release*, 69: 399-412, 2000.

Huynh et al., "Carboxymethylation of Dextran in Aqueous Alcohol as the First Step of the Preparation of Derivatized Dextrans", *Die Angewandte Makromolekulare Chemie*, 254: 61-65, 1998.

Kagedal et al., "Binding of Covalent Proteins to Polysaccharides by Cyanogen Bromide and Organic Cyanates. I. Preparation of Soluble Glycine-, Insulin- and Ampicillin-Dextran", *Acta Chemica Scandinavica*, 25: 1855-1859, 1971.

Kim and Park "Glucose-binding property of pegylated concanavalin A", *Pharmaceutical Research*, 18: 794-99, 2001.

Kim and Park "Modulated insulin delivery from glucose-sensitive hydrogel dosage forms", *J. Controlled Release*, 77: 39, 2001.

Kim et al. "Insulinotropic activity of sulfonylurea/pullulan conjugate in rat islet microcapsule", *Biomaterials*, 24: 4843, 2003.

Looger et al., "Computational Design of Receptor and Sensor Proteins with Novel Functions", *Nature*, 423: 185-190, 2003.

Medina-Bolivar et al., "A non-toxic lectin for antigen delivery of plant-based mucosal vaccines", *Vaccine*, 21: 997-1005, 2003.

Mehvar et al., "Molecular-Weight-Dependent Pharmacokinetics of Fluorescein-Labeled Dextrans in Rats", *Journal of Pharmaceutical Sciences*, 81(9): 908-912, 1992.

Mislovicova et al., "Neoglycoconjugates of Mannan with Bovine Serum Albumin and Their Interaction with Lectin Concanavalin A", *Bioconjugate Chem.*, 13: 136-142, 2002.

Mitra et al., "Tumour Targeted Delivery of Encapsulated Dextran-Doxorubicin Conjugate Using Chitosan Nanoparticles as Carrier", *Journal of Controlled Release*, 74: 317-323, 2001.

Ohya et al., "Design of Macromolecular Prodrug of Cisplatin Using Dextran with Branched Galactose Units as Targeting Moieties to Hepatoma Cells", *Biomacromolecules*, 2: 927-933, 2001.

Persson et al., "Surfactant Protein D is a Divalent Cation-Dependent Carbohydrate-Binding Protein", *The Journal of Biological Chemistry*, 265(10): 5755-5760, 1990.

Sakamoto et al., "Comparative Effects of Native Insulin and Insulin-Dextran Complexes on the Metabolism of Adipose Tissue", *Biochimica et Biophysica Acta*, 498: 102-113, 1977.

Salins et al., "A Novel Reagentless Sensing System for Measuring Glucose Based on the Galactose/Glucose-Binding Protein", *Analytical Biochemistry*, 294: 19-26, 2001.

Sheriff et al., "Human Mannose-Binding Protein Carbohydrate Recognition Domain Trimerizes Through a Triple $\alpha$-Helical Coiled-Coil", *Structural Biology*, 1(11): 789-794, 1994.

Sugahara et al., "Characteristics of Tissue Distribution of Various Polysaccharides as Drug Carriers: Influences of Molecular Weight and Anionic Charge on Tumor Targeting", *Biol. Pharm. Bull.*, 24(5): 535-543, 2001.

Suzuki et al., "Studies on the mode of insulin: properties and biological activity of an insulin-dextran complex", *Endocrinology*, 90: 1220-1230, 1972.

Tanna et al., "Covalent coupling of concanavalin A to a Carbopol 934P and 941P carrier in glucose-sensitive gels for delivery of insulin", *J. Pharm. Pharmacol.*, 11: 1461, 2002.

Thoma et al., "Versatile Functionalization of Polylysine: Synthesis, Characterization, and Use of Neoglycoconjugates", *J. Am. Chem. Soc.*, 121: 5919-5929, 1999.

Ueno et al., "Polyethylene Glycol-Modified Concanavalin A as an Effective Agent to Stimulate Anti-Tumor Cytotoxicity", Cancer Detection and Prevention, 24(1): 100-6, 2000.

Ueno et al., "Polyethylene glycol-modified pokeweed mitogen (PWM) as a potential non-immunogenic stimulator of lymphokine-activated killer cells", *J. Biomater. Sci. Polymer Edn.*, 7: 753, 1996.

Zion et al., "Bio-Inspired Nanoscale Hybrid Systems", *Materials Research Society*, Fall Meeting, Boston, MA, C10.12: p. 44, 55, Dec. 2-4, 2002.

Zion et al., "Glucose-responsive materials for self-regulated insulin delivery", Thesis, Massachusetts Institute of Technology, Dept. of Chemical Engineering, 2004.

International Search Report for PCT/US03/40393.

International Search Report for PCT/US 06/41035, mailed Aug. 8, 2007.

Cheng, *Development of a Tissue Engineered Pancreatic Substitute Based on Genetically Engineered Cells*, Thesis, Georgia Institute of Technology, 2005.

He, et al., *Life Sciences*, 65(4): 355-368, 1999.

Johnson, et al., *J. of Bacteriology*, 91(3): 967-974, 1966.

Walsh, et al., *Antimicrobal Agents and Chemotherapy*, 47(2): 554-558, 2003.

International Searching Report for PCT/US06/41167 mailed Oct. 19, 2006.

* cited by examiner

| Fraction# | Time Start | Time End |
|---|---|---|
| 1 | 5.6 | 15.6 |
| 2 | 15.6 | 20.1 |
| 3 | 20.1 | 26.2 |
| 4 | 26.2 | 31.5 |
| 5 | 31.5 | 36.0 |
| 6 | 36.0 | 39.5 |
| 7 | 39.5 | 42.5 |
| 8 | 42.5 | 45.5 |
| 9 | 45.5 | 49.0 |
| 10 | 49.0 | 52.0 |
| 11 | 52.0 | 55.0 |
| 12 | 55.0 | 59.0 |
| 13 | 59.0 | 64.0 |
| 14 | 64.0 | 67.5 |
| 15 | 67.5 | 77.5 |

| | FP62 Stock Concentration (mg/mL) | | | | | | | |
|---|---|---|---|---|---|---|---|---|
| | **A** | **B** | **C** | **D** | **E** | **F** | **G** | **H** |
| **Row 1 - FITC-FP62 Control**<br>50 uL of FP62 stock<br>100 uL of S7 buffer | 30 | 3 | 0.3 | 0.03 | 0.003 | 0.0003 | 0.00003 | 0.000003 |
| **Row 2 - FITC-FP62 Control w/Glc**<br>50 uL of FP62 stock<br>50 uL of S7 Stock<br>50 uL of Glucose stock | 30 | 3 | 0.3 | 0.03 | 0.003 | 0.0003 | 0.00003 | 0.000003 |
| **Row 3 - FITC-FP62 + TRITC-mannan, No Glc**<br>50 uL of FP62 stock<br>50 uL of TRITC-mannan Stock<br>50 uL of S7 stock | 30<br>**30** | 3<br>**3** | 0.3<br>**0.3** | 0.03<br>**0.03** | 0.003<br>**0.003** | 0.0003<br>**0.0003** | 0.00003<br>**0.00003** | 0.000003<br>**0.000003** |
| **Row 4 - FITC-FP62 + TRITC-mannan, WITH Glc**<br>50 uL of FP62 stock<br>50 uL of TRITC-Mannan Stock<br>50 uL of Glucose stock | 30<br>**30** | 3<br>**3** | 0.3<br>**0.3** | 0.03<br>**0.03** | 0.003<br>**0.003** | 0.0003<br>**0.0003** | 0.00003<br>**0.00003** | 0.000003<br>**0.000003** |
| **Row 5 - FITC-FP62 + Reverse TRITC-mannan, No Glc**<br>50 uL of FP62 stock<br>50 uL of TRITC-Mannan Stock<br>50 uL of S7 stock | 30<br>**0.000003** | 3<br>**0.00003** | 0.3<br>**0.0003** | 0.03<br>**0.003** | 0.003<br>**0.03** | 0.0003<br>**0.3** | 0.00003<br>**3** | 0.000003<br>**30** |
| **Row 6 - FITC-FP62 + Reverse TRITC-mannan, No Glc**<br>50 uL of FP62 stock<br>50 uL of TRITC-Mannan Stock<br>50 uL of Glucose stock | 30<br>**0.000003** | 3<br>**0.00003** | 0.3<br>**0.0003** | 0.03<br>**0.003** | 0.003<br>**0.03** | 0.0003<br>**0.3** | 0.00003<br>**3** | 0.000003<br>**30** |
| **Row 7 - TRITC-mannan Control, NO Glc**<br>50 uL of TRITC-Mannan stock<br>100 uL of S7 buffer | 30 | 3 | 0.3 | 0.03 | 0.003 | 0.0003 | 0.00003 | 0.000003 |
| **Row 8 - TRITC-mannan Control, WITH Glc**<br>50 uL of FP62 stock<br>50 uL of S7 Stock<br>50 uL of Glucose stock | 30 | 3 | 0.3 | 0.03 | 0.003 | 0.0003 | 0.00003 | 0.000003 |

Figure 20

Steady state flow viscosities of all samples at 22°C

Steady state flow viscosities of all samples at 37°C

| Lectin Monomer Site of Modification | Polymer activation agent | Polymer | Conjugate Bond Type | Notes | Reference |
|---|---|---|---|---|---|
| Amine (primary or secondary) | N-hydroxysuccinimide | Carboxyl terminated poly(ethylene glycol) | Amide | | |
| | N-hydroxysuccinimide | Any | Amide | Examples 1-43 | |
| | Cyanogen bromide or cyanodimethylaminopyridine tetrafluoroborate (CDAP) | Polysaccharide | Carbamate | Example 44 | |
| | Sodium periodate | Polysaccharide | Amine | Secondary reduction with sodium cyanoborohydride | |
| | None | Carboxylic acid containing polymer | Amide | Use water soluble coupling agent - EDAC | |
| Aromatic alcohol (tyrosine) | N-hydroxysuccinimide | Poly(ethylene glycol)<br>Any | Ester | pH dependent | |
| Sulfhydryl (cysteine) | Maleimide | Any | Thioether | | |
| | Divinyl sulfone | Alcohol or amine containing polymer | Ether or amine | | |
| | None | Sulfhydryl-containing polymer | Disulfide | | |
| Carboxyl | None | Amine containing polymer | Amide | Use water soluble coupling agent - EDAC | |

METHODS FOR REDUCING THE MITOGENICITY OF LECTIN COMPOSITIONS

PRIORITY INFORMATION

This application claims priority to U.S. Ser. No. 60/728,652 filed Oct. 19, 2005. The entire contents of this application are hereby incorporated by reference.

STATEMENT REGARDING FEDERALLY SPONSORED RESEARCH OR DEVELOPMENT

This invention was made with government support under Grant Number 1R43DK069870, awarded by the National Institutes of Health ("NIH"). The U.S. government has certain rights in the invention.

BACKGROUND OF THE INVENTION

Lectins are highly specific carbohydrate-binding proteins. Lectins have been isolated from a variety of natural sources including seeds, roots, bark, fungi, bacteria, seaweed, sponges, mollusks, fish eggs, body fluids of invertebrates and lower vertebrates, and mammalian cell membranes (e.g., see *The Lectins: Properties, Functions, and Applications in Biology and Medicine*, Edited by Liener et al., Academic Press, 1986). A number of lectins have also been produced recombinantly (e.g., see Streicher and Sharon, *Methods Enzymol.* 363:47-77, 2003). As noted, lectins bind carbohydrates with a high degree of specificity. For example, some lectins will bind only to carbohydrates with mannose or glucose residues, while others only recognize carbohydrates that include galactose residues. Some lectins require that the particular residue be in a terminal position, while others bind to residues within a carbohydrate chain. Some lectins require specific anomeric structures and yet others recognize specific sugar sequences. The structures and properties of lectins have been extensively described in the literature. For recent reviews see *Lectins*, Edited by Sharon and Lis, Kluwer Academic Publishers, 2003; *Handbook of Animal Lectins: Properties and Biomedical Applications*, Edited by Kilpatrick, Wiley, 2000; and *Handbook of Plant Lectins: Properties and Biomedical Applications*, Edited by Van Damme et al., Wiley, 1998. Each of these references and any other publication that is cited herein is hereby incorporated by reference.

Most lectins studied to date are multimeric, consisting of non-covalently associated subunits. While some multimeric lectins include two or more identical subunits (e.g., Concanavalin A), others are composed of different subunits (e.g., *Phaseolus vulgaris*). Each subunit can bind an independent carbohydrate structure. The multivalent binding properties of multimeric lectins allow them to agglutinate cells by binding to carbohydrate structures on multiple cell surfaces. For this reason, cellular agglutination assays are commonly used to identify novel lectins. Although most lectins can agglutinate some cell type, cellular agglutination is not a prerequisite. In particular some lectins are monovalent while others do not recognize cell-surface carbohydrate structures. Most multivalent lectins are also capable of forming precipitates with glycoconjugates (e.g., complex carbohydrates, glycoproteins, glycolipids, etc.).

Lectins bind carbohydrate structures non-covalently. The binding in a lectin-carbohydrate complex can therefore be reversed or inhibited by competing monosaccharides such as glucose (and even certain di-, tri- or polysaccharides). A variety of methods and devices have been described in the art that take advantage of the reversible carbohydrate binding properties of lectins. For example, sensors that monitor sugar concentrations using lectins have been described (e.g., see U.S. Pat. Nos. 5,814,449; 6,454,710 and 6,671,527). Devices that rely on lectins to deliver drugs such as insulin in a controlled and glucose responsive manner have also been described (e.g., see U.S. Pat. Nos. 5,830,506; 5,902,607 and 6,410,053).

Unfortunately, many of the most readily available lectins pose great risks in vivo because they have the potential to stimulate lymphocyte proliferation (e.g., without limitation, Artocarpus integrifolia agglutinin (Jacalin), Bauhinia purpurea agglutinin (BPA), Concanavalin A (Con A), succinyl-Concanavalin A (s-Con A), Erythrina corallodendron agglutinin (ECorA), Euonymus europaeus agglutinin (EEA), Glycine max agglutinin (SBA), Lens culinaris agglutinin (LcH), Maackia amurensis agglutinin (MAA), *Phaseolus vulgaris* agglutinin (PHA), Pokeweed mitogen (PWM), Wheat germ agglutinin (WGA), and Vicia faba agglutinin (VFA) all of which are available from Sigma-Aldrich of St. Louis, Mo.). By binding to carbohydrate receptors on the surfaces of certain types of lymphocytes, these and other so-called "mitogenic" lectins induce the mitosis of lymphocytes and thereby cause them to proliferate. Most mitogenic lectins including Con A and PHA are selective T-cell mitogens. A few lectins such as PWM are less selective and stimulate both T-cells and B-cells. Local or systemic in vivo exposure to mitogenic lectins results in inflammation, cytotoxicity, macrophage digestion, and allergic reactions including anaphylaxis. In addition, plant lectins are known to be highly immunogenic, giving rise to the production of high titers of anti-lectin specific antibodies.

It will be appreciated that mitogenic lectins cannot therefore be used for in vivo methods and devices unless great care is taken to prevent their release. For example, in U.S. Pat. No. 5,830,506, the inventor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in vivo uses of lectins could be significantly diminished if the mitogenicity of lectin compositions could be reduced or even eliminated. There is therefore a need in the art for methods of reducing the T-cell mitogenicity of lectin compositions. In particular, there is a need for methods that reduce the T-cell mitogenicity of lectins under physiological conditions. There is also a need for methods that do not adversely affect the carbohydrate binding properties of lectins.

SUMMARY OF THE INVENTION

In one aspect the invention provides methods for reducing the T-cell mitogenicity of lectin compositions. In one embodiment, this is achieved by chemically modifying mitogenic lectin compositions under optimized conditions (e.g., chemical compound used as a modifying reagent, temperature, pH, etc.). In particular, we have found that conditions and chemical compounds that produce modified lectins with uniform levels of modification are preferred. Conditions that produce high levels of modifications are particularly preferred. Additionally or alternatively, the reduction in T-cell mitogenicity is achieved by removing unmodified subunits (and/or subunits with low levels of modification) from chemically modified mixtures. In certain embodiments, the resulting modified lectin compositions retain advantageous properties including the ability to bind cognate saccharide and polysaccharide ligands.

In another aspect the invention provides modified lectin compositions with reduced T-cell mitogenicity. In one embodiment, the modified lectin compositions retain their binding affinity for cognate saccharide and polysaccharide ligands. Additionally or alternatively, the modified lectin compositions have increased minimum agglutination concentrations, higher cell viability properties, a reduced ability to activate antigens on the surface of T-cells, a reduced ability to induce production of cytokines, reduced in vivo toxicity, and/or a reduced ability to trigger the production of unmodified lectin-specific antibodies.

In yet another aspect the invention provides various uses of the inventive compositions including glucose sensors and controlled delivery systems for therapeutic agents.

BRIEF DESCRIPTION OF THE DRAWING

FIG. 20. Microtiter plate layout for the FP62/FRET glucose sensor application.

FIG. 29. An abbreviated listing of lectin monomer site modification site moieties, potential polymer coupling methods, compatible polymer agent chemistries, and the final polymer-lectin conjugate bond type.

FIG. 30. SDS-PAGE analysis-standard, native lanes (3), Batch A and Batch B.

DEFINITIONS

Figure 1:
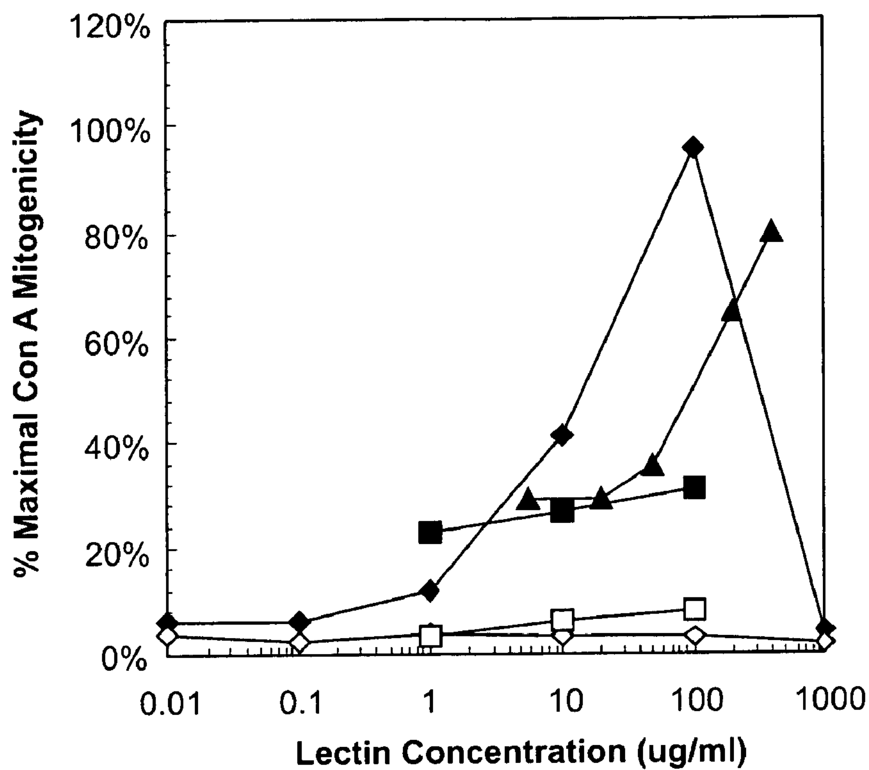
FIG. 1. % maximal Con A mitogenicity vs. the concentration evaluated in the PBMC culture medium. (♦) P39, (▲) Ueno's High PEG Con A adapted from published results, (■) P44-4, (□) P44-7, and (◇) P26.

Agglutinated—When two or more cells are "agglutinated" by a lectin as described herein, they are each physically associated with the lectin in a cell-lectin-cell complex. Typically, lectin-induced cell agglutination only occurs once the lectin concentration reaches a threshold concentration. This concentration is referred to as the minimum agglutination concentration (MAC). The MAC for a given lectin composition is commonly measured using a spectrophotometric plate reader that can quantify changes in solution absorbance.

Associated—When two entities are physically "associated" with one another as described herein, they are linked by direct non-covalent interactions. The term "bound" is used interchangeably with the term "associated" herein. Desirable non-covalent interactions include, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. The association properties of selected molecular entities (e.g., a lectin and a saccharide or polysaccharide) can be quantified using methods well known in the art (e.g., see Davies et al., *Annual Rev. Biochem.* 59:439, 1990).

Carbohydrate, polysaccharide or oligosaccharide—As used herein a "carbohydrate", "polysaccharide" or "oligosaccharide" is a polymer of sugars, typically of at least three sugars. The terms may be used interchangeably. The polymer may include natural sugars (e.g., glucose, fructose, galactose, mannose, arabinose, ribose, and xylose) and/or modified sugars (e.g., 2'-fluororibose, 2'-deoxyribose, hexose, etc.).

Cognate ligand—As used herein, the "cognate ligand" of a particular lectin is any one of the saccharides or polysaccharides that is recognized by the native lectin.

Lectin—As used herein, a "lectin" is a protein that binds with specificity to saccharides and polysaccharides. A lectin can be of any origin (e.g., plant, animal or other). In certain embodiments a lectin can be isolated from a natural source. In other embodiments a lectin can be produced synthetically or recombinantly. A lectin can be composed of one or more subunits under physiological conditions. In preferred embodiments a lectin is composed of two or more subunits under physiological conditions (e.g., four subunits). The subunits may be the same or different.

Mitogenic lectin—A "mitogenic lectin" is a lectin that stimulates the proliferation of T-cells as measured by a thymidine uptake assay using peripheral blood mononuclear cells (PBMC) from one or more healthy patients. Generally a mitogenic lectin will produce a detectable level of thymidine uptake at concentrations of 1 ug/ml. Preferred mitogenic lectins include, but are not limited to, Artocarpus integrifolia agglutinin (Jacalin), Bauhinia purpurea agglutinin (BPA), Concanavalin A (Con A), succinyl-Concanavalin A (s-Con A), Erythrina corallodendron agglutinin (ECorA), Euonymus europaeus agglutinin (EEA), Glycine max agglutinin (SBA), Lens culinaris agglutinin (LcH), Maackia amurensis agglutinin (MAA), *Phaseolus vulgaris* agglutinin (PHA), Pokeweed mitogen (PWM), Wheat germ agglutinin (WGA), and Vicia faba agglutinin (VFA) all of which are available from Sigma-Aldrich of St. Louis, Mo. It is to be understood that the terms "mitogenic lectin" include derivatives of native lectins that retain the ability to stimulate the proliferation of T-cells (e.g., derivatives that include amino acid substitutions, deletions or additions). Exemplary derivatives are those into which amino acid residues have been introduced by site-directed mutagenesis (e.g., in order to provide additional reactive groups for chemical modification). Generally, suitable derivatives will have at least 90% sequence homology with a native lectin as determined using standard methods known in the art (e.g., using Blast with default settings). Preferably the derivatives will have at least 95% sequence homology, more preferably 99% sequence homology with a native lectin. Without limitation, exemplary derivatives may induce a level of T-cell proliferation that is at least 90% that of their native counterparts. More preferably, the level is at least 95%, even more preferably at least 99%.

Modified subunit—As used herein, a "modified subunit" refers to a subunit of a lectin that has been modified by treatment with a chemical compound. For purposes of this invention, the chemical compound reacts with the subunit to form a covalent bond, e.g., without limitation an amino acid residue. For example, in one embodiment the chemical compound is an activated pegylation agent. In certain embodiments, the chemical compound is monovalent and reacts with a single subunit. In other embodiments the chemical compound may be multivalent in which case it may react with one or more subunits.

Native lectin—As used herein, a "native lectin" is a protein with the chemical composition of a lectin that is found in nature.

Physiological conditions—As used herein, "physiological conditions" are those conditions that are found in the arterial blood of a typical patient. Generally, the patient is a mammal, e.g., a human, dog, cat, mouse, etc. In human patients, the pH under physiological conditions is typically between about 7.35 and about 7.45 (preferably about 7.40). Human physiological temperatures range from about 36.4 to about 37.4 C. (preferably about 36.9 C.).

Polypeptide—As used herein a "polypeptide" is a polymer that includes a string of at least two amino acid residues linked together by peptide bonds. The terms "oligopeptide", "peptide", "polypeptide" and "protein" may be used interchangeably. Polypeptides preferably contain only natural amino acid residues, although non-natural amino acids (i.e., compounds that do not occur in nature but that can be incorporated into a polypeptide chain) and/or amino acid analogs as are known in the art may alternatively be employed. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Reduced T-cell mitogenicity—A lectin composition is said to exhibit "reduced T-cell mitogenicity" or "reduced mitogenicity" as compared to a native lectin composition if it induces a detectably lower level of T-cell proliferation as measured by a thymidine uptake assay using peripheral blood mononuclear cells (PBMCs) from one or more healthy patients. Generally, the comparative assay is performed across a range lectin concentrations, e.g., 0.01, 0.1, 1, 10, 100 and 1000 ug/ml. In preferred embodiments, the thymidine uptake assay is performed with samples that include approximately 500,000 PBMCs. The mitogenicity of the test composition (e.g., a chemically modified composition) is then expressed as the % maximal native mitogenicity. The % maximal native mitogenicity is obtained by dividing the maximal CPM (counts per minute) value for the test composition over all measured concentrations by the maximal CPM value of the native lectin composition over all measured concentrations. Preferably, the test composition with reduced mitogenicity induces a level of T-cell proliferation that is at least 50% lower than the native lectin composition. More preferably, the level is at least 75% lower, even more preferably at least 90%, 95% or 99% lower.

Saccharide—As used herein, the term "saccharide" refers to monomers of sugars. A saccharide can be a natural sugar (e.g., glucose, fructose, galactose, mannose, arabinose, ribose, and xylose) or a modified sugar (e.g., 2'-fluororibose, 2'-deoxyribose, hexose, etc.).

Substantially non-mitogenic—As used herein, a "substantially non-mitogenic" composition is a composition that induces an undetecable level of T-cell proliferation as measured by a thymidine uptake assay using peripheral blood mononuclear cells (PBMCs) from one or more healthy patients. As defined herein, a lectin composition is said to induce an undetectable level of T-cell proliferation when it yields thymidine uptake values that are statistically insignificant (i.e., P>0.05) as compared to a control composition (i.e., plain medium). As defined herein, a substantially non-mitogenic composition of the invention includes lectins at a concentration of at least 1 ug/ml. In certain preferred embodiments, the same composition still yields thymidine uptake values that are statistically insignificant when concentrated up to 10 ug/ml.

Substantially the same—As used herein, a second value is "substantially the same" as a first value if the second value is within ±25% of the first value.

DETAILED DESCRIPTION OF CERTAIN PREFERRED EMBODIMENTS OF THE INVENTION

A. Introduction

Methods for chemically modifying lectins have been described in the prior art. For example, pegylation has been used to reduce the immunoreactivity (i.e., antibody reactivity) and immunogenicity (i.e., antibody production) of PWM and Con A; to increase the circulation half-life of Con A; and to increase the solubility and stability of Con A. To date, no one has attempted to chemically modify lectins in order to reduce their T-cell mitogenicity. Others have measured the incidental effect of chemical modification on T-cell mitogenicity; however, in each case the mitogenicity was not significantly reduced. In particular, no method has been disclosed that significantly reduced the T-cell mitogenicity of a lectin composition while preserving its beneficial carbohydrate binding properties.

Ueno used pegylation to prepare modified Con A compositions that stimulate anti-tumor cytotoxicity in peripheral lymphocytes (Ueno et al., *Cancer Detection and Prevention* 24:100-106, 2000). 2,4-bis[O-methoxypoly(ethylene glycol)]-6-chloro-s-triazine was used as an activated pegylation agent and the reaction was performed at 37 C. and pH 10. The maximum level of pegylation that was achieved under these conditions was only about 35% (i.e., 4.5/13 available amine group pegylation sites per Con A molecule). Ueno compared the cytotoxicity, immunoreactivity, immunogenicity and circulation half-lives of native Con A and 35% pegylated Con A. The T-cell mitogenicity of each composition was also measured using murine spleen T-cells at 37 C. in RPMI 1640 medium and was found to be reduced in the modified compositions as compared to native Con A. However, as noted by Ueno, the modified compositions retained the ability to stimulate a proliferative T-cell response. Specifically, the maximal T-cell mitogenicity of a modified Con A composition evaluated from 0.05-400 ug/ml (with about 4.5/13 available amine group pegylation sites) was 79% of the maximal mitogenicity for native Con A evaluated over the same concentration range. As described in Examples 1, 15, and 17, we have also attempted to reproduce the Ueno modification protocol and performed mitogenicity assays using radioactive thymidine uptake on human PBMC cells. We found that the maximal T-cell mitogenicity of a modified Con A composition evaluated from 0.01-100 ug/ml (with about 4.5/13 available amine group pegylation sites) was 31% of the maximal mitogenicity for native Con A evaluated over the same concentration range.

Kim and Park used pegylation to increase the solution stability of Con A compositions (Kim and Park, *Pharmaceutical Research* 18:794-799, 2001). Monomethoxy poly(ethylene glycol) p-nitrophenol carbonate was used as an activated pegylation agent; the reaction was begun at 4 C. and then slowly warmed to room temperature. The reaction mixture was buffered at pH 8.5 and they were able to obtain relatively high levels of pegylation (i.e., up to 77% pegylation or 10/13 available amine group pegylation sites per Con A molecule). The solubility and stability of the modified Con A compositions was increased as compared to native Con A. However, while moderately pegylated Con A molecules (i.e., below 5/13 available amine group pegylation sites) retained the carbohydrate binding properties of native Con A, these properties vanished rapidly if the level of pegylation was increased. Kim and Park were not interested in and did not measure the T-cell mitogenicity of their modified compositions. However, as described in Examples 1, 16, and 17, we have attempted to reproduce their modification protocol and performed mitogenicity assays using human PBMC cells. We found that the maximal T-cell mitogenicity of a modified Con A composition evaluated from 0.01-1000 ug/ml (with about 5/13 available amine group pegylation sites) was 96% of the maximal mitogenicity for native Con A evaluated over the same concentration range.

We have developed methods that allow the mitogenicity of modified lectin compositions (including the Ueno and Kim and Park modified Con A compositions) to be significantly reduced. We have also developed methods that allow the carbohydrate binding properties of modified lectin compositions to be substantially preserved as described in Examples 4 and 19. Finally, we have determined the properties of modified compositions that are the best predictors of reduced mitogenicity as described in Examples 18, 25, 26 and 27.

In one aspect, the inventive methods stem from our finding that the degree of modification in the mitogenic modified Con A compositions of the prior art (including those of Ueno and Kim and Park) is non-uniform. In particular, instead of finding that the subunits in modified Con A compositions were uniformly modified, we unexpectedly found that mitogenic modified compositions tend to include significant fractions of native (i.e., unmodified) subunits as well as modified subunits with low levels of modification. Based on these findings we speculated that these unmodified subunits and subunits with low degrees of modification were responsible for the residual mitogenicity exhibited by these compositions. As described in Examples 1, 5, 17, and 18, subsequent experiments have confirmed this to be the case. In another set of experiments we optimized the modification protocol (i.e., the reagents and reaction conditions) as described in Examples 11, 18 and 21 in order to improve the uniformity of modification. Uniformly modified compositions were shown to exhibit reduced mitogenicity. In another set of experiments described in Examples 22-24 we removed native (i.e., unmodified) subunits from mitogenic modified compositions and demonstrated that this step correlated with a significant reduction in T-cell mitogenicity. In preferred cases, no T-cell mitogenicity could be detected.

B. Methods for Reducing the Mitogenicity of Lectin Compositions

In one aspect the present invention provides methods for reducing the mitogenicity of lectin compositions by removing unmodified subunits from compositions that have been treated with a chemical compound such as an activated pegylation agent. The methods may begin directly with the chemically modified composition or may include a preliminary step of preparing this composition.

In the latter situation one would generally begin with a composition that includes a plurality of mitogenic lectins. The mitogenic lectins are each comprised of one or more subunits. In one embodiment they include two or more subunits (e.g., four subunits) that may be identical or different. The mitogenic lectin composition is then reacted with a chemical compound that reacts with at least some of the subunits to produce modified subunits. Without limitation, the chemical compound may be a pegylation agent. The mitogenicity of the chemically modified composition is preferably, but not necessarily, reduced as compared to the mitogenic lectin composition.

Then, the chemically modified composition is treated by removing at least a portion of the unmodified subunits. Unmodified subunits may be removed by any means. For example, they may be isolated from the remainder of the chemically modified composition based on their differential molecular size, e.g., by methods outlined in Example 13; their differential electrical charges, e.g., as demonstrated by Example 22; and/or their differential binding affinities for a saccharide or polysaccharide, e.g., as shown in Examples 23 and 24. The T-cell mitogenicity of the chemically modified lectin composition is reduced as a result of this removal step.

Step of Reacting with a Chemical Compound

A variety of chemical compounds may be used in the step of reacting. Generally, any chemical compound that reacts with lectins may be used. Preferred chemical compounds reduce the T-cell mitogenicity of the resulting composition. The chemical compound or compounds may react with any residue or residues on the mitogenic lectin.

In one embodiment, the chemical compound or compounds are monovalent. Activated pegylation agents are preferred but non-limiting monovalent chemical compounds of the invention (e.g., without limitation N-hydroxysuccinimide activated PEG, succinimidyl ester of PEG propionic acid, succinimidyl ester of PEG butanoic acid, succinimidyl ester of PEG alpha-methylbutanoate, etc.). Examples 1-43 deal with pegylated Con A, while Example 44 describes the use of a polysaccharide as the chemical compound. Other exemplary monovalent chemical compounds include natural and synthetic amino acids, other water soluble but non-PEG-containing polymers such as poly(vinyl alcohol), reagents that can be easily coupled to lysines, e.g., through the use of carbodiimide reagents, and perfluorinated compounds. The skilled artisan will readily recognize other suitable chemical compounds, e.g., by referring to the comprehensive review that can be found in "*Chemical Reagents for Protein Modification*" by Lundblad, CRC Press, 3rd Edition, 2004.

In another embodiment, the chemical compound or compounds are multivalent. Multivalent chemical compounds can react with more than one lectin subunit and are therefore capable of crosslinking two or more subunits. Examples 40 and 41 describe inventive methods that used the exemplary bivalent crosslinking agent ethylene glycol-bis(succinic acid-N-hydroxy-succinimide ester). It is to be understood that the invention is in no way limited to the exclusive use of monovalent or multivalent chemical compounds and that in certain embodiments it may prove advantageous to react the mitogenic lectin composition with a multivalent chemical compound and then react the crosslinked lectin subunits with a monovalent chemical compound (or vice versa). It will also be appreciated that the same mitogenic lectin composition may be simultaneously or sequentially treated with more than one monovalent (or multivalent) chemical compound.

Generally the chemical compounds may be of any molecular weight, and may be branched or unbranched. Preferably the chemical compounds have a molecular weight of about 1 to about 100 kD, more preferably 1 to 10 kD, for example about 1, 2, 5 or 10 kD. In the case of pegylation agents, the preferred molecular weight is between about 1 kD and about 40 kD, preferably 1 to 10 kD. The chemical compound may have a branched structure. Branched PEGs are described, for example, in U.S. Pat. No. 5,643,575; Morpurgo et al., *Appl. Biochem. Biotechnol.* 56:59-72, 1996; Vorobjev et al., *Nucleosides Nucleotides* 18:2745-2750, 1999; and Caliceti et al., *Bioconjug. Chem.* 10:638-646, 1999.

The chemical compounds may be attached to a mitogenic lectin via any of a number of attachment methods known to those skilled in the art (e.g., via amine, carboxyl, hydroxyl or sulfhydryl groups on the lectin subunits). The potential covalent linkages are similarly diverse (e.g., including amide bonds, carbamate bonds, ester bonds, thioether bonds, ether bonds, disulfide bonds, etc.). In certain embodiments suitable reactive groups can be grafted onto a mitogenic lectin by introducing an appropriate amino acid by site-directed mutagenesis as is known in the art.

For example, PEGs are conveniently attached through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues may also be used as a reactive group for attaching the PEGs (or other chemical compounds). In preferred embodiments PEGs are covalently attached to an amino group, especially the free amino group found in lysine residues.

Numerous methods for directly attaching PEGs to proteins are described in Delgado et al., *Crit. Rev. Thera. Drug Carrier Sys.* 9:249-304, 1992; Francis et al., *Intern. J. of Hematol.* 68:1-18, 1998; U.S. Pat. No. 4,002,531; U.S. Pat. No. 5,349,052; WO 95/06058; and WO 98/32466. One such method uses tresylated monomethoxy poly(ethylene glycol) (MPEG), which is produced by reacting MPEG with tresylchloride ($ClSO_2CH_2CF_3$). Tresylated MPEG reacts with exposed amine groups on lectins. A skilled person will recognize that the invention is not limited to any specific pegylation agent (or chemical compound) and will be able to identify other suitable chemical compounds that are known in the art.

In certain embodiments PEGs may be attached to a lectin via an intervening linker. For example, U.S. Pat. No. 5,612,460, discloses urethane linkers for connecting polyethylene glycol to proteins. PEGs can be attached to a lectin via a linker by reaction with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. In the Examples below we described the use of succinimidyl propionic acid activated MPEG. Kim and Park (supra) describe the use of MPEG p-nitrophenol carbonate. Ueno et al. (supra) describe the modification of lectins using a branched MPEG, namely 2,4-bis[O-methoxypoly(ethylene glycol)]-6-chloro-s-triazine. A number additional PEG derivatives and reaction chemistries for attaching polyethylene glycol to proteins are described in WO 98/32466 and other patents, e.g., those that are assigned to Shearwater of Huntsville, Ala.; Nektar Therapeutics of San Carlos, Calif.; and/or Enzon Pharmaceuticals of Bridgewater, N.J. Catalogues can be obtained from these commercial PEG suppliers that describe a range of suitable PEG compounds and chemistries (e.g., see the Nektar Advanced PEGylation CATALOG 2004).

The number of chemical compounds that are attached to each lectin subunit (i.e., the degree of substitution) will vary based on the nature of the chemical compound or compounds, the number of reaction sites available and the reaction conditions. For example, the subunits of Con A each include twelve lysine residues. Thus if Con A is pegylated with an agent that reacts with lysine residues then each Con A subunit can be covalently linked to 1, 2, 3, 4, 5, 6, 7, 8, 9, 10, 11 or 12 PEG molecules. Methods for determining the degree of substitution are discussed in the Examples and also in Delgado et al., *Crit. Rev. Thera. Drug Carrier Sys.* 9:249-304, 1992.

In preferred embodiments, the chemical modification of a mitogenic lectin composition will be optimized using a plurality of chemical compounds and a plurality of reaction conditions (e.g., that vary the reagent concentrations, pH, temperature, etc.). Preferred chemical compounds and reaction conditions are such that the mitogenicity of the treated composition is reduced as compared to the untreated compositions. For example, an automated robotic handling device may be used to prepare a range of modified compositions with different chemical compounds and different reaction conditions. Using routine orthogonal experimentation a skilled person can then screen the mitogenicity of the treated compositions using a T-cell proliferation assay as described below and in Example 1. Compositions that exhibit reduced mitogenicity are identified. In certain embodiments further rounds of orthogonal optimization are performed around the preferred conditions to further refine the preferred chemical compounds and reaction conditions.

In one embodiment, optimal reaction conditions are identified by separating treated compositions by electrophoresis, preferably by denaturing SDS-PAGE electrophoresis as described in Example 5. Compositions with uniformly modified lectin subunits are preferred compositions of the invention. These preferred compositions will have weaker bands at the molecular weight of the native unmodified subunits as measured by SDS-PAGE and demonstrated in Examples 18 and 19. It will also be appreciated that the inventive methods are not limited to such compositions. In fact, as discussed in the following section, the inventive methods are most usefully applied to compositions that do not include uniformly modified subunits. Indeed, by removing unmodified subunits, the inventive methods are able to substantially reduce the mitogenicity of these compositions.

Step of Removing Unmodified Lectin Subunits

Once the chemically modified lectin composition has been prepared, preferably under optimized conditions, the inventive method includes a step of removing at least a portion of the unmodified subunits from the treated composition. It is to be understood that this portion may be removed by any method. Generally, unmodified subunits may be removed based on their physical properties (e.g., electrical charge; molecular weight; and/or size) and/or based on their chemical properties (e.g., binding affinity for a ligand such as a saccharide or polysaccharide). In certain embodiments optimal removal may be achieved by combining two or more methods that rely on these differential properties.

In one embodiment described in Examples 18 and 19, unmodified subunits are removed under denaturing conditions (i.e., under conditions where the subunits are not associated in dimers, tetramers or higher order aggregates). In other embodiments unmodified subunits are removed under non-denaturing conditions. In the latter case it will be appreciated that unmodified and modified subunits may be associated, e.g., as dimers or tetramers at the time of removal and thus that some modified subunits may be removed along with unmodified subunits. However, as long as the removal step preferentially removes those aggregates that include unmodified subunits then a net removal of unmodified subunits will still be achieved. For example, if the lectin is tetrameric under the removal conditions then a net removal of unmodified subunits can be achieved by removing tetramers that include 4 unmodified subunits; by removing tetramers that include 3 or 4 unmodified subunits; by removing tetramers that include 2, 3 or 4 unmodified subunits; or by removing tetramers that include 1, 2, 3 or 4 unmodified subunits. Variations on this logic will be understood by a skilled artisan.

Unmodified subunits can be removed from a treated composition on the basis of their net charge by ion-exchange chromatography via methods in Example 22. For example, if the unmodified subunits carry more positive charge than modified subunits (as is the case for pegylated lectins) they will bind to a column of beads containing negative charges with greater affinity than modified subunits. The positively charged subunits that are bound to such a column can then be eluted by increasing the concentration of sodium chloride or another salt in the eluting buffer. The sodium ions will compete with positively charged groups on the unmodified subunits for binding to the column. This type of column is commonly referred to as a cation exchange column. Subunits that have a low density of net positive charge will tend to emerge first, followed by those having a higher charge density. If the unmodified and modified subunits carry different amounts of negative charge these can be separated in the same manner using a column of beads containing positive charges (i.e., an anion exchange column). Eluent sampling can be performed over periodic intervals, and the individual fractions assayed by SDS-PAGE to analyze the molecular weight composition of each fraction.

Gel-filtration chromatography may be used to discriminate between modified and unmodified subunits on the basis of size as described in Example 13. Unmodified subunits (and aggregates that include these) will be lighter and smaller than their modified counterparts. The method involves passing the treated composition through a column that consists of porous beads made of an insoluble but highly hydrated polymer such as polyacrylamide. Smaller moieties can enter these beads, but large ones cannot. Larger moieties (i.e., those with a greater proportion of modified subunits) flow more rapidly through the column and emerge first because a smaller volume is accessible to them. Smaller moieties (e.g., unmodified subunits or aggregates with a greater proportion of unmodified subunits) which take a longer, tortuous path, will exit last. Eluent sampling can be performed over periodic intervals, and the individual fractions assayed by SDS-PAGE to analyze the molecular weight composition of each fraction.

Affinity chromatography is another method that may be used to remove unmodified subunits. This approach takes advantage of the differential binding affinity of modified and unmodified subunits for a specific ligand, e.g., glucose or other saccharide such as mannose, a polysaccharide, e.g., dextran, glycogen, or mannan in the case of glucose/mannose binding lectins. For example, the treated composition can be passed through a column of beads with covalently attached glucose or mannose. In another embodiment, the treated composition can be passed through a column of beads with covalently attached dextran, or mannan residues as described in Examples 23 and 24. The modified and unmodified subunits (or aggregates that include these) bind to the beads with differing affinities. The bound entities can then be released from the column by adding a concentrated solution of glucose. The free glucose will compete with the covalently linked glucose, mannose, dextran, or mannan for binding to the subunits. In preferred embodiments the concentration of glucose is increased gradually or stepwise in order to release subunits with different binding affinities at different points. Subunits with lower binding affinities will be released at a lower concentration of glucose and will therefore exit first. Subunits with higher binding affinities will be released at a higher concentration of glucose and will therefore exit last. Eluent sampling can be performed over periodic intervals, and the individual fractions assayed by SDS-PAGE to analyze the molecular weight composition of each fraction.

Mitogenicity Assay

In preferred embodiments the T-cell mitogenicity of the chemically modified composition is reduced after the step of removing. As described in the Examples we have found that this step can lead to a dramatic reduction in T-cell mitogenicity thereby allowing lectin compositions to be used for in vivo applications. The T-cell mitogenicity of compositions of interest may be determined and thence compared using any known assay. Generally, suitable assays will involve contacting the compositions of interest with a T-cell culture (e.g., PBMC cells) for a period of time and then measuring the level of T-cell proliferation. Various methods for measuring cell proliferation are known. In one embodiment the cell density may be measured spectrophotometrically at 450 nm. In another embodiment an indirect measure can obtained by detecting the reduction of MTT at 570 nm (e.g., see Ohno et al., *J. Immunol. Methods* 145:199-203, 1991). In preferred embodiments, the level of cell proliferation is determined using the tritiated thymidine uptake assay that is described Example 1. Those skilled in the art will recognize that other suitable methods may be used and that the invention is in no way limited to a specific proliferation assay.

Cell Viability Assay

In preferred embodiments the cell viability of a T-cell culture treated with the chemically modified composition is substantially unchanged or improved after the step of removing. As described in the Examples we have found that the removal step can lead to a substantial retention of T-cell viability thereby allowing lectin compositions to be used for both in vitro and in vivo applications. The T-cell viability of compositions of interest may be determined and thence compared using any known assay. Generally, suitable assays will involve contacting the compositions of interest with a T-cell culture (e.g., PBMC cells) for a period of time and then measuring the level of T-cell viability. Various methods for measuring cell proliferation are known.

In a preferred embodiment described in Example 2, Trypan Blue is added to the culture. A representative sample of the cells are counted, noting those that either take up the trypan or still exclude the trypan (i.e., those that become blue vs. those that do not). The % viability is then calculated by dividing the number of cells that exclude the trypan (alive, "not blue") by the total number of cells counted (dead, "blue," plus live, "not blue"). Those skilled in the art will recognize that other suitable methods may be used and that the invention is in no way limited to a specific viability assay.

Binding Affinity Assay

In certain embodiments the modified composition has a binding affinity for a cognate saccharide and/or polysaccharide after the removal step that is substantially the same as the original mitogenic lectin composition. Preferably the binding affinity is at least 75% that of the mitogenic lectin composition. More preferably the binding affinity is at least 85% and yet more preferably at least 95% that of the mitogenic lectin composition. Binding affinities can be ascertained using any known method. In preferred embodiments the binding affinities are compared under physiological conditions and using a lectin concentration of 1 or 10 μg/ml. For example the relative binding affinities can be determined by affinity chromatography using a saccharide resin. Equilibrium dialysis can also be used as is known in the art. In one embodiment the concentration of saccharide required to inhibit the precipitation of glycogen, branched dextran, or mannan can be determined and a binding affinity derived therefrom using standard calculations. In preferred embodiments, microcalorimetry is used as described in the Example 4.

Agglutination Assay

In other embodiments the modified composition has a minimum agglutinating concentration (MAC) after the removal step that is higher than the mitogenic lectin composition. Preferably the MAC is 25 times that of the untreated composition. More preferably the MAC is 50 times and yet more preferably more than 100 times that of the untreated composition. The MAC can be ascertained using any known agglutination assay. In preferred embodiments the MACs are compared using rabbit erythrocytes as described in the Example 6.

Glycogen Precipitation Assay

In other embodiments the modified composition has a reduced glycogen precipitation value after removal despite being capable of binding analogous saccharides and polysaccharides. Preferably the glycogen precipitation value is less than 50% of the original mitogenic lectin composition value. More preferably the value is less than 75%, and yet preferably less than 90% of that value. The glycogen precipitation value can be ascertained using any known glycogen precipitation assay, e.g., see Goldstein et al., *Biochim. Biophys. Acta* 97:68-76, 1965. In preferred embodiments the glycogen precipitation value is ascertained by mixing compositions with glycogen solutions of varying concentration and measuring the absorbance at 490 nm as described in the Examples 7 and 27.

In some applications, it may be desirable to precipitate a chemically modified lectin with a polysaccharide. In order for precipitation to occur the lectin must be able to form multimers so that it can simultaneously bind more than one polysaccharide (i.e., one polysaccharide via each subunit in the multimer). We hypothesized that chemical modification of the lectins would potentially disrupt the degree of valency by preventing the formation of higher order multimers. Such a phenomenon has been observed for Con A chemically modified with succinyl groups (Gunther et al., *Proc. Natl. Acad. Sci. USA* 70:1012-1016, 1973) or acetyl groups (Agrawal et al., *Biochemistry* 7:4211-4218, 1968). In order to overcome the potentially decreased ability to precipitate polysaccharides, in one embodiment it may prove advantageous to chemically crosslink the lectin subunits together to prevent dissociation after chemical modification and/or to create even higher valency structures. This type of crosslinking was described above in the context of multivalent chemical compounds and is further explored in Example 40.

C. Compositions

The present invention encompasses all chemically modified lectin compositions that have been prepared and treated according to the aforementioned methods. Generally, an inventive compositions includes a plurality of modified lectins. The modified lectins are comprised of one or more subunits that have been modified by reaction with a chemical compound and the inventive composition is substantially free of unmodified subunits. The T-cell mitogenicity of the composition is also reduced as compared to an otherwise equivalent composition that comprises a plurality of unmodified lectins (e.g., the native lectin composition).

In one embodiment, the one or more subunits have been modified by reaction with a monovalent chemical compound as described previously. In another embodiment, the one or more subunits have been crosslinked by reaction with a multivalent chemical compound. Optionally the crosslinked subunits have been further modified by reaction with a monovalent chemical compound. The composition may include a modified lectin that is multimeric and comprised of identical subunits in its native form. For example, the composition might include a modified lectin that is tetrameric in its native form. Preferred compositions include modified Concanavalin A, modified Pisum sativum agglutinin, modified Lens culinaris lectin, modified Vicia faba lectin, modified Glycine max lectin, modified Wheat germ agglutinin, or a combination thereof. All of the details regarding the nature of the chemical compound and the linkage, etc. that were described in the previous methods section apply equally here and are incorporated herein by reference.

In one embodiment, fewer than 50% of the subunits in an inventive composition are unmodified as determined by denaturing gel electrophoresis. Preferably fewer than 25% and even more preferably fewer than 10% of the subunits in an inventive composition are unmodified as determined by denaturing gel electrophoresis.

In another embodiment, the T-cell mitogenicity of an inventive composition is less than 50% the T-cell mitogenicity of an otherwise equivalent composition that comprises a plurality of unmodified lectins (e.g., the native lectin composition). As previously discussed, the reduction in T-cell mitogenicity is generally assessed by performing a comparative thymidine uptake assay across a range lectin concentrations, e.g., 0.01, 0.1, 1, 10, 100 and 1000 ug/ml. In preferred embodiments, the thymidine uptake assay is performed with samples that include approximately 500,000 PBMCs. The mitogenicity of the test composition (e.g., a chemically modified composition) is then expressed as the % maximal native mitogenicity. The % maximal native mitogenicity is obtained by dividing the maximal CPM (counts per minute) value for the test composition over all measured concentrations by the maximal CPM value of the native lectin composition over all measured concentrations. Preferably, the test composition with reduced mitogenicity induces a level of T-cell proliferation that is at least 50% lower than the native lectin composition. More preferably, the level is at least 75% lower, even more preferably at least 90%, 95% or 99% lower.

In one embodiment, an inventive composition may also exhibit a binding affinity for a cognate saccharide ligand that is substantially equal to or greater than an otherwise equivalent composition that comprises a plurality of unmodified lectins. In another embodiment, an invention composition binds detectably with a cognate polysaccharide ligand.

In certain embodiments, the present invention provides a chemically modified lectin composition that exhibits a minimum agglutination concentration (MAC) with a 2% v/v suspension of formaldehyde-stabilized rabbit erythrocytes that is greater than 4 ug/ml, and a binding affinity for a cognate saccharide ligand that is substantially equal to or greater than an otherwise equivalent composition that comprises a plurality of unmodified lectins. Preferably the MAC is greater than 6 ug/ml, more preferably greater than 10 ug/ml, even more preferably greater than 25 ug/ml.

In certain embodiments, the present invention provides a chemically modified lectin composition that exhibits a percentage cell viability at 100 ug/ml that is greater than 10% when assayed using PBMCs at a concentration of 500,000 cells/ml, and a binding affinity for a cognate saccharide ligand that is substantially equal to or greater than an otherwise equivalent composition that comprises a plurality of unmodified lectins. Preferably the percentage cell viability is greater than 25%, more preferably greater than 50%, even more preferably greater than 90%.

In certain embodiments, the present invention provides a chemically modified lectin composition that exhibits reduced activation of antigens on the surface of T-cells at 1 ug/ml as compared to an otherwise equivalent composition that comprises a plurality of unmodified lectins when assayed using PBMCs at a concentration of 500,000 cells/ml, and a binding affinity for a cognate saccharide ligand that is substantially equal to or greater than an otherwise equivalent composition that comprises a plurality of unmodified lectins.

In certain embodiments, the present invention provides a chemically modified lectin composition that exhibits a reduced ability to induce production of cytokines at 1 ug/ml as compared to an otherwise equivalent composition that comprises a plurality of unmodified lectins when assayed using PBMCs at a concentration of 500,000 cells/ml, and a binding affinity for a cognate saccharide ligand that is substantially equal to or greater than an otherwise equivalent composition that comprises a plurality of unmodified lectins.

In certain embodiments, the present invention provides a chemically modified lectin composition that exhibits reduced in vivo toxicity as compared to an otherwise equivalent composition that comprises a plurality of unmodified lectins, and a binding affinity for a cognate saccharide ligand that is substantially equal to or greater than an otherwise equivalent composition that comprises a plurality of unmodified lectins.

D. Applications

Chemically modified lectin compositions that have been prepared and treated according to the methods of the present invention may be used in a variety of contexts. In particular, the compositions may be used for in vivo applications since they exhibit reduced T-cell mitogenicity but also greater T-cell viability, reduced cell agglutination, preserved saccharide and substantially preserved polysaccharide binding affinity, reduced in vivo toxicity, reduced ability to activate T-cell antigens, and/or a reduced ability to induce cytokine or antibody production. The following are non-limiting examples of suitable applications.

Glucose Sensors

Non-mitogenic lectins of the invention may be used in glucose sensors.

In one embodiment, non-mitogenic lectins of the invention may be used in glucose sensors that are based on fluorescence resonance energy transfer (FRET). FRET is based on the fact that when two different fluorophores are brought closely together this allow for energy transfer between the two fluorophores, resulting in a decrease in the fluorescence of one or both of the fluorophores, which is called fluorescence quenching (Ballerstadt et al., *Anal. Chim. Acta* 345:203-212, 1997). In the absence of a monosaccharide inhibitor, a mixture of a fluorescent modified Con A and a fluorescent polysaccharide will form a compact gel and the neighboring fluorophores will undergo FRET. In the presence of a monosaccharide inhibitor such as glucose, the average distance between the fluorescent modified Con A and the fluorescent polysaccharide will increase causing the level of FRET to decrease and thereby leading to an increase in the individual fluorescence signals. As discussed in detail in Example 35, inventive modified lectins that retain the ability to bind higher affinity polysaccharides and saccharides such as glucose are ideally suited for this application.

In another embodiment, non-mitogenic lectins of the invention may be used in glucose sensors that are based on the changes in viscosity of a glucose-responsive solution. The method requires a polymer containing a plurality of saccharide moieties and a modified lectin from an inventive composition that exhibits affinity for glucose and for the saccharide moieties of the polymer. When the polymer and modified lectin are mixed together, the viscosity of the resulting mixture will be due to the binding between the polymer and the modified lectin. The mixture can then be contacted with a sample containing glucose which displaces the polymer from the modified lectin and causes a concentration dependent reduction in viscosity. By measuring the resulting change in viscosity once can calculate the concentration of glucoe in the sample of interest. Example 36 provides further details for this application.

Glucose Sensitive Systems for Controlled Delivery of Therapeutic Agents

Non-mitogenic lectins of the invention may also be used in glucose sensitive systems for controlled delivery of therapeutic agents. Insulin is a preferred therapeutic agent but the invention is in no way limited to the use of insulin.

In one embodiment the non-mitogenic lectins could be used in a system with a conjugate of a saccharide or a relatively small polysaccharide and the therapeutic agent of interest (e.g., an insulin-maltose conjugate as described in U.S. Pat. No. 4,348,387). These small conjugates will form water soluble complexes when contacted with the inventive lectins. Release of the conjugate from the inventive modified lectin will then be controlled primarily by competitive binding between free glucose and the conjugate. As noted, maltose is a suitable saccharide for the conjugate; however, other saccharides and small polysaccharides can be used, e.g., a manno-oligosaccharide containing from 2 to 7 (1→2) α-D-mannopyranosyl residues. It is to be understood that the present invention also provides a composition comprising the inventive water soluble complex. This application of the inventive compositions is further discussed in Example 37.

In another embodiment the non-mitogenic lectins could be used in a system that uses an unconjugated therapeutic agent, e.g., free insulin. Preferred systems would use modified lectins that still contain multiple binding sites for saccharides, with a particular affinity for glucose and mannose residues. The binding of glucose to the binding site should remain reversible. The inactive form of the drug system comprises glucose or mannose present as terminal moieties of a polysaccharide. The polysaccharide is a branched chain polysaccharide with many terminal glucose or mannose moieties which can bind to the binding sites of modified lectins and in so doing cross-link the modified lectins together to form a viscous gel matrix. An unconjugated therapeutic agent is premixed with the gel, so that when the modified lectin is added to the mixture, a gel is formed between the polysaccharide and the modified lectin with the agent relatively immobilized inside the gel matrix and thus unable to escape rapidly. The binding of polysaccharide to modified lectin is reversed when there is an increase in the concentration of free glucose in the physiological environment. The free glucose displaces the terminal glucose or mannose from the binding sites of the modified lectins. The matrix undergoes a conformational change allowing mobilization and release of the therapeutic agent into the environment. Once the level of free glucose falls (e.g., in response to the action of the released insulin), the displaced terminal glucose or mannose molecules will re-bind to the modified lectin molecules and the matrix will re-gel, thus again restricting the therapeutic agent to remain within the matrix. The mechanism of this drug system is thus repeatable and releases the therapeutic agent in response to a number of free glucose insults, in a similar manner to the in vivo feedback mechanism of the pancreatic cells. It is to be understood that the present invention also provides a composition comprising inventive gelled matrices. Example 38 provides additional details and embodiments for this specific application.

In yet another embodiment the non-mitogenic lectins could be used in a system with a conjugate of a polysaccharide and the therapeutic agent of interest (e.g., based on the teachings of U.S. Patent Publication No. 2004/0202719). Suitable modified lectins would have at least two binding sites, each with an affinity for glucose and the polysaccharide portion of the conjugate. The conjugate and modified lectin would need to combined under conditions in which the modified lectin cross-links the conjugate to form a water insoluble gelled matrix. When the matrix is placed in a glucose solution the cross-links are competitively dissociated thereby causing an ungelling of the matrix and a release of the conjugate into the solution. It is to be understood that the present invention also provides a composition comprising inventive gelled matrices. Examples 40 and 41 provide additional details and embodiments for this specific application.

EXAMPLES

(A) General Methods

Examples 1-13 describe general methods (e.g., assays and purification methods) that were used in preparing and characterizing lectin compositions that are described in later examples.

Example 1 describes an assay that was used to characterize and thereby compare the T-cell mitogenicity of different lectin compositions.

Example 2 describes an assay that was used to determine the impact of different lectin compositions on the viability of human peripheral blood mononuclear cells (PBMCs) in culture.

Example 3 describes an assay that was used to determine the percent pegylation of modified Con A compositions. The same assay can be used to determine the level of modification with other chemicals and/or for other lectins.

Example 4 describes a microcalorimetry method that was used to evaluate the saccharide binding affinities of various lectin compositions.

Example 5 describes a method that was used to perform SDS-PAGE separations of various lectin compositions.

Example 6 describes a method that was used to determine the cell agglutination properties of various lectin compositions.

Example 7 describes an assay that was used to characterize the glycogen precipitation properties of various lectin compositions. As discussed in Example 27, the results of this assay were found to correlate with the results obtained using the mitogenicity assay of Example 1.

Example 8 describes a general method for preparing pegylated Con A compositions. This particular example describes the reagents and conditions for preparing modified Con A composition P62. Other pegylated Con A compositions that are described in later examples (e.g., those of Example 11) were prepared using slight variations on this general method (e.g., different pegylation reagent, different ratios of reagents, different pH and/or temperature, different buffers, etc.).

Examples 9 and 10 describe ultrafiltration and dialysis methods, respectively, for removing reaction byproducts and unreacted reagents from modified lectin compositions.

Example 11 describes a high throughput method for preparing families of pegylated Con A compositions. As discussed, the method is derived from the general procedure of Example 8.

Example 12 describes a general procedure for establishing the glucose set point (GSP) curve for a glucose-regulated insulin delivery system comprising an insulin-polymer conjugate and a multivalent glucose binding molecule such as the modified lectin molecules present in the compositions of the invention (e.g., see Examples 39 and 41).

Example 13 describes a general method for characterizing lectin compositions with varying degrees of chemical modification on the basis of molecular size using size-exclusion chromatography (SEC). As discussed in Example 40, this method can also be used to separate the component molecules of a single modified lectin composition.

Example 1

Mitogenicity Assay

This example describes an assay that was used to characterize and thereby compare the T-cell mitogenicity of different lectin compositions. Modifications and alternatives to this typical assay will be apparent to those skilled in the art. Peripheral blood mononuclear cells (PBMCs), rather than highly purified T-cells, were used for this assay since T-cell activation by lectins generally requires the presence of non-T-cell populations collectively termed accessory cells (e.g., monocytes, dendritic cells). In a typical assay, PBMCs were isolated from the whole blood of three healthy donors and plated out separately at about 100,000 cells per well in a 96 well plate. Triplicate serial dilutions of different lectin compositions (e.g., native and treated) starting at 1000 (or 100) ug/ml concentration were then added to the wells. The plates were incubated for three days at 37 C, at which time 0.8 uCi of $^{3}$H-thymidine was added to each well for an additional 18 hours. The degree of mitogenicity was then measured by $^{3}$H-thymidine uptake by the proliferating PBMCs. In some cases, the mitogenicity of a lectin composition (e.g., a treated composition) was expressed as the % maximal native mitogenicity. The % maximal native mitogenicity was obtained by dividing the maximal CPM (counts per minute) value for the lectin composition over all measured concentrations by the maximal CPM value of the native lectin composition over all measured compositions.

Example 2

Cell Viability Assay

This example describes an assay that was used to determine the impact of different lectin compositions on the viability of human PBMCs in culture. PBMCs were incubated as described in Example 1 (i.e., three days, plus 18 hours) with a particular concentration of a lectin composition of interest (e.g., 0.01-1000 ug/ml). At the end of the incubation period, Trypan Blue (Sigma-Aldrich, St. Louis, Mo.) was added to the culture. A representative sample of cells from the culture was then counted while noting those that either took up the trypan (i.e., those that were blue and thus dead) or still excluded the trypan (i.e., those that were not blue and thus alive). The % viability was calculated by dividing the number of cells that excluded the trypan (i.e., live cells) by the total number of cells counted (i.e., dead plus live cells).

Example 3

Measuring the Extent of Chemical Modification

This example describes an assay that was use to determine the pegylation levels for various modified Con A compositions. It will be appreciated by those skilled in the art that the same assay can be modified for use with other forms of chemical modification and/or with other lectins. Lyophilized samples of the modified Con A compositions were dissolved to known concentrations in PBS (10 mM Na-phosphate, pH 7.2, 0.15 M NaCl, 0.1 mM $CaCl_2$, and 0.04% $NaN_3$). UV absorbance spectra were recorded between 240 nm and 320 nm using a Shimadzu UV160 spectrophotometer and 0.2, 0.5, or 1.0 cm cuvettes (depending on the concentration used). Spectra were compared to that of native Con A at 1 mg dry wt/ml in the same buffer. The native Con A sample had a peak absorbance at 278 nm at this concentration. All pegylated samples of Con A exhibited the same shape spectrum in this wavelength range (comparing both actual spectra and first derivative spectra), thereby indicating that pegylation does not alter the absorption spectrum of Con A. Therefore, absorption at 278 nm was used to estimate the actual concentration of Con A in the modified Con A compositions. The percent protein and percent pegylation were then calculated by comparing the actual protein concentration to the total weight concentration.

Example 4

Measuring Saccharide Binding Affinities

This example describes a method that was used to evaluate the saccharide binding affinities of various lectin compositions. The binding constants between lectins and various saccharides, oligosaccharides and polysaccharides were determined by microcalorimetry. The number of binding sites per lectin molecule could also be determined. The lectin was first dissolved at a given concentration in solution. The cell in which the lectin resides was controlled in a manner so as to keep the cell temperature constant by means of constant heat flow (i.e., the calorimeter measures the total heat supplied or removed from the cell in order to maintain a constant temperature). A saccharide (e.g., glucose, mannose, α-methyl mannose), oligosaccharide (e.g., 3,6-Di-O-(a-D-mannopyranosyl)-D-mannopyranose), or polysaccharide (e.g., dextran or mannan of molecular weight less than 150 kD) solution was then added to the cell in small increments. The added saccharide binds to the lectin, and the thermodynamically favorable interaction releases a small quantity of heat into the solution, which is measured by the calorimeter as a reduction in the amount of heat supplied to maintain the constant temperature. Small aliquots of saccharide were continually added until all of the lectin binding sites had been "titrated" with saccharide. The resulting data could then be fitted with a thermodynamic model using two parameters, namely the binding constant, $K_a$ and the number of binding sites per molecule, n.

Calorimetry was performed in a Micro-Cal VP-ITC microcalorimeter, using a 1.4 cm titration cell. Typical lectin concentrations were in the range of 4-6 mg total dry wt/ml PBS. All samples were titrated with 1-10 mM saccharide solutions in the same buffer, using 4 μl increments, increasing to 8 μl after the expected stoichiometric end point until only background heat of dilution was observed (i.e., total saturation was reached). Data were fit to the single site model using Origins software supplied with the instrument.

Example 5

SDS-PAGE Separations

This example describes a method that was used to perform sodium dodecyl sulfate-polyacrylamide gel electrophoresis (SDS-PAGE) separations of various lectin compositions. SDS-PAGE is commonly used to separate and characterize proteins in a mixture on the basis of size. The SDS helps denature proteins so as to rule out "size effects" caused by compactly coiled or folded proteins.

SDS-PAGE separations were performed essentially as described by Laemmli, *Nature* 227:680:685, 1970. Briefly, Laemmli sample buffer was made by mixing 950 ul of 1× Laemmli Sample Buffer (Bio-Rad, Hercules, Calif.) with 50 ul of 2-mercaptoethanol. The desired protein sample was diluted in 1×PBS buffer to a concentration of 1.0 mg/ml. 25 ul of this solution was pipetted into a microcentrifuge tube, followed by 50 ul of 1× Laemmli Sample Buffer. The centrifuge tube was closed, vortexed briefly, and then placed into boiling water for 5 minutes. After boiling, the sample was cooled in ice-cold water. The desired samples were then pipetted into a BioRad 15-well (15 ul capacity) precast 4-15% gradient polyacrylamide gel and run at 150 V for 70 minutes. The desired samples were run against a mixture of proteins that act as molecular weight standards. After running the gel, the protein bands were fixed in the gel using a 40:10:50 methanol:acetic acid:water mixture by volume for 15 minutes, followed by washing twice with distilled water. The bands were revealed by staining with colloidal Coomassie blue stain for 1.5 hours. The background staining was removed from the gel by 3× washing in distilled water. Pictures of the bands were taken by placing the developed gels on a light table and capturing images of the gel with a digital camera attached to a personal computer. The relative densities of electrophoretic bands were quantitatively measured by AlphaImage software. Multimeric lectins (e.g., Con A which exists as a tetramer in solution) stain at monomeric molecular weights because of the SDS denaturing gel conditions.

Example 6

Cell Agglutination Assay

This example describes a method that was used to determine the cell agglutination properties of various lectin compositions. The minimum agglutinating concentrations (MAC) of each composition was determined in V-well microtitre plates using a 2% v/v suspension of formaldehyde-stabilized rabbit erythrocytes according to the procedure of Crowley et al., *Methods. Enzymol.* 83:368-373, 1982. Formaldehyde-treated rabbit erythrocytes, prepared by published procedures (Nowak et al., *Biochim. Biophys. Acta* 393:115-123, 1975), from rabbit blood obtained from University of Michigan Unit for Laboratory Animal Medicine, were available from previous studies. The MAC is defined as the lectin protein concentration (exclusive of attached chemical compounds such as PEG) in the highest dilution showing visible agglutination.

Briefly, an aqueous solution of a lectin composition was added to the wells of a 96-well plate using 2× serial dilutions so that the lectin concentration spanned from about 0.1 to 100 ug/ml. An aliquot of the formaldehyde-treated Rabbit erythrocytes was then pipetted into each well. At low lectin concentrations, there was insufficient lectin to form a network of crosslinked cells, and the solutions remained clear. However, once the lectin concentration reached the minimum agglutination concentration (MAC), the lectin molecules began crosslinking the saccharide receptors on the erythrocyte surfaces, resulting in an opaque solution. The change in solution absorbance was quantified using a spectrophotometric plate reader.

Example 7

Glycogen Precipitation Assay

This example describes an assay that was used to characterize the glycogen precipitation properties of various lectin compositions. As discussed in Example 27, the results of this assay were found to correlate with results obtained with the mitogenicity assay of Example 1. Thus in certain cases, this assay was used as a surrogate for the mitogenic assay of Example 1.

Briefly, unmodified Oyster glycogen Type II (Sigma Aldrich, St. Louis, Mo.) was dissolved at 10 mg/ml in pH 7, 200 mM BES buffer (Sigma Aldrich, St. Louis, Mo.). 50 ul of the glycogen solution was then pipetted into a well of a 96-well microtiter plate (VWR Scientific, Bridgeport, N.J.). Lectin compositions were dissolved from a lyophilized powder at 10 mg/ml in pH 7, 100 mM BES buffer containing 1 mM manganese chloride and 1 mM calcium chloride. 50 ul of the lectin solution was then added to the 50 ul glycogen solution in the microtiter plate well, and the plate was gently vibrated to ensure adequate mixing of the two liquids.

Similarly, a negative control well was made by adding 100 ul of the 10 mg/ml glycogen solution to one separate well on the microtiter plate, and one positive control well was made by mixing 50 ul of the glycogen solution with 50 ul of a 10 mg/ml native lectin solution in pH 7, 100 mM BES buffer containing 1000 mM sodium chloride and 1 mM manganese chloride and 1 mM calcium chloride.

The plate was allowed to develop at room temperature for 10 minutes, after which time the turbidity of each plate well was assayed using a commercially available microplate reader (SpectraMAx, Molecular Devices, Mountain View, Calif.) at a wavelength of 490 nm (OD490). The OD490 values could then be compared to the positive (native lectin plus glycogen) control and negative control (glycogen only) to determine the relative amount of glycogen precipitation for a given lectin composition. Generally, lectin compositions with OD490 values >0.3 were found to be also mitogenic as measured by the assay of Example 1.

Example 8

General Method for Preparing Pegylated Con A Compositions (P62)

The modified lectin compositions that are discussed in the following examples are each given the label P followed by a numerical identifier. For pegylated Con A compositions, the modified Con A molecules within each composition are also sometimes given an identifier of the type "PEG-X-Y-Con A," where X refers to the number of moles of PEG reagent added to the reaction mixture per mole of native Con A subunit (MW 26 kD) and Y refers to the molecular weight of the PEG reagent in daltons (D).

This particular example describes the preparation of modified Con A composition P62 that is composed of "PEG-10-5k-Con A" molecules. Other pegylated Con A compositions that will described in later examples were prepared using slight variations on this general method (e.g., different pegylation reagent, different ratios of reagents, different pH and/or temperature, different buffers, etc.).

100 mg of native Con A (Type V, Sigma-Aldrich, St. Louis, Mo.) was dissolved in 10 ml of 100 mM BES buffer at pH 7.4 containing 1 M NaCl, 1 mM $CaCl_2$ and 1 mM $MnCl_2$. The resulting mixture included 10 mg of Con A per ml and was stirred at room temperature until all components were dissolved.

Separately, 190 mg of the pegylation agent mPEG-SPA-5K (succinimidyl propionic acid activated mPEG, MW 5 kD, Nektar Therapeutics, San Carlos, Calif.) was added to 1.90 ml of 100 mM BES buffer at pH 7.4 containing 1 M NaCl, 1 mM $CaCl_2$ and 1 mM $MnCl_2$ and vortexed until dissolved. This mixture was then slowly added dropwise using a pipette to the above solution at room temperature. The amount of pegylation agent was adjusted so that the molar ratio of pegylation agent to Con A monomer (MW 26 kD) was about 10. After addition, the resulting solution was stirred overnight at room temperature.

The following day the solution was ultrafiltered as described in Example 9. The resulting solution was then lyophilized to yield modified Con A composition P62.

Example 9

Ultrafiltration and Lyophilization of Modified Lectins

In some of the examples, the modified lectin compositions were purified free of reaction byproducts and unreacted reagents through ultrafiltration. In the case of pegylated Con A compositions, the compositions were taken from their reaction mixtures at a concentration of approximately 10 mg/ml (on a Con A reagent mass basis) and ultrafiltered at room temperature using a 200 ml size stirred cell (Amicon Model 3000, Millipore Corporation, Billerica, Mass.) using a 50 kD MW cut-off filtration disc (Millipore Corporation, Billerica, Mass.). The solutions were extensively ultrafiltered against 100 mM BES buffer at pH 7 containing 1000 mM NaCl, 1 mM $CaCl_2$ and 1 mM $MnCl_2$ to remove unreacted pegylation agent, and then extensively against deionized water containing 1 mM $CaCl_2$ and $MnCl_2$. The role of manganese and calcium ions has been described previously (Sophianopoulos et al., *Prep. Biochem.* 11:413-435, 1981). The resulting solutions were then lyophilized to yield essentially pure, pegylated Con A compositions.

Example 10

Dialysis and Lyophilization of Modified Lectins

In other examples, the modified lectin compositions were purified free of reaction byproducts and unreacted reagents through equilibrium dialysis. This was found to be particularly convenient when preparing small batches of a modified lectin. In the case of pegylated Con A compositions, the compositions were taken from their reaction mixtures at a concentration of approximately 10 mg/ml (on a Con A reagent mass basis) and placed into equilibrium dialysis tubing (MW cut-off of 50 kD, Spectrapor brand, VWR Scientific, Bridgeport, N.J.). The solutions were extensively dialyzed against 100 mM BES buffer at pH 7 containing 1000 mM NaCl, 1 mM $CaCl_2$ and 1 mM $MnCl_2$ to remove unreacted pegylation agent (100× volume turnover, dialysis buffer changed twice daily for 3 days), and then extensively against deionized water containing 1 mM $CaCl_2$ and 1 mM $MnCl_2$ (100× volume turnover, dialysis buffer changed twice daily for 3 days). The resulting solutions were then lyophilized to yield essentially pure, pegylated Con A compositions.

We have observed that for modified Con A compositions containing PEG:Con A monomer molar ratios of greater than or equal to 5, it is useful to dialyze or ultrafilter the compositions against a buffer containing manganese ions or calcium ions at a sufficient concentration in order to preserve the saccharide binding properties of the modified Con A compositions. In this context, we note that Kim and Park (*Pharmaceutical Research,* 18:794-799, 2001) found that modified Con A compositions with high PEG:Con A monomer molar ratios lost their ability to bind saccharides (see page 797). Of interest, the authors described dialysis against distilled, deionized water and made no reference, specific or otherwise, to the incorporation of manganese or calcium ions in their procedure.

Example 11

High Throughput Method for Preparing Pegylated Con A Compositions

A high throughput method (based on the general method of Example 8) was developed to facilitate the synthesis of pegylated Con A compositions to allow for the screening of large numbers of compositions based on different variables such as buffer choice, pH, reaction temperature, PEG reagent molecular weight, PEG reagent linker group, degree of pegylation, etc.

This specific example describes the use of this method in preparing a family of PEG-X-Y-Con A compositions with X values of (0, 2.5, 5, 7.5, 10, 12.5, 15, 17.5 and 20) and a Y value of 2 kD. As noted in Example 8, X refers to the number of moles of PEG reagent added to the reaction mixture per mole of native Con A subunit (MW 26 kD) while Y refers to the molecular weight of the PEG reagent in daltons (D). There are 12 accessible lysine amino acid residues on each Con A subunit that are preferred to react with PEG reagents in this example.

Briefly, native Con A (Type V, Sigma Aldrich, St. Louis, Mo.) was dissolved in a synthesis buffer of choice (in this case pH 7, 100 mM BES containing 1 M NaCl) at a concentration of 10 mg/ml. The protein solution was stirred gently until all of the protein was dissolved and the solution was visibly clear. Next, 500 ul of the Con A solution was pipetted into each well of a 24-well cell culture plate (VWR Scientific, Bridgeport, N.J.) and each well was equipped with a miniature half inch-long magnetic stir bar. The 24-well plate was placed onto a magnetic stirrer to allow for good mixing in each well.

In a new beaker, PEG with a MW of 2 kD and the linker group SPA (Succinimidyl Propionate, Nektar Therapeutics, San Carlos, Calif.) was dissolved in pH 7, 100 mM BES containing 1000 mM NaCl at 100 mg/ml by mixing 0.100 g of the PEG-SPA-2k in 1.0 ml of buffer. Because most PEG reagents, including PEG-SPA-2k, are susceptible to hydrolysis in aqueous buffers, the PEG reagent-buffer solution was vortexed to aid in its dissolution and was used quickly (within 15 minutes of dissolution) to prevent undue hydrolysis.

Aliquots of the PEG reagent stock solution were added in the amounts set forth in Table 1 to each well of the 24-well plate to achieve the desired degree of pegylation. The mixtures were allowed to react overnight at room temperature.

TABLE 1

Amounts of PEG-SPA-2k stock used to achieve desired PEG:Con A monomer molar ratios.

| Con A Solution (mL) | PEG reagent | Amount of PEG solution (mL) | PEG:Con A Monomer Molar Ratio | PEG:Con A Monomer Mass Ratio |
|---|---|---|---|---|
| 0.5 | — | 0.000 | 0.0 | 0.000 |
| 0.5 | PEG-SPA-2k | 0.010 | 2.5 | 0.192 |
| 0.5 | PEG-SPA-2k | 0.019 | 5.0 | 0.385 |
| 0.5 | PEG-SPA-2k | 0.029 | 7.5 | 0.577 |
| 0.5 | PEG-SPA-2k | 0.038 | 10.0 | 0.769 |
| 0.5 | PEG-SPA-2k | 0.048 | 12.5 | 0.962 |
| 0.5 | PEG-SPA-2k | 0.058 | 15.0 | 1.154 |
| 0.5 | PEG-SPA-2k | 0.067 | 17.5 | 1.346 |
| 0.5 | PEG-SPA-2k | 0.077 | 20.0 | 1.538 |

Because no saccharides were used in the high throughput synthesis approach and since unreacted PEG reagent does not adversely affect the glycogen precipitation assay, the cell agglutination assay, or the mitogenicity assay, the high throughput compositions could be used directly for these studies without further purification. However, if desired, the samples could be purified by one of the methods described in Examples 9 and 10.

Example 12

Glucose Set Point Assay

This example describes the general procedure for establishing the glucose set point (GSP) curve for a glucose-regulated insulin delivery system comprising an insulin-polymer conjugate and a multivalent glucose binding molecule such as the modified lectin molecules present in the compositions of the invention (e.g., see Examples 39 and 41). Briefly, 1.0 ml of 1×PBS buffer containing 0 mg/dl of D-glucose is added to each of the 24 wells of a Multiwell™ plate (Becton Dickinson, Franklin Lakes, N.J.). An amount of the test delivery system is then added to the solution (in the form of a gel) and agitated for 1 hour using a microplate incubator/shaker ("Jitterbug," Boekel Industries, Philadelphia, Pa.) set at 37 C. After 1 hour, 0.5 ml of release medium is removed and the insulin-polymer concentration in the medium is determined by porcine insulin ELISA (ALPCO Diagnostics, Windham, N.H.). The remaining release medium is then supplemented with 0.5 ml of a 100 mg/dl glucose serum solution to make a 50 mg/dl solution, and the gels are agitated for another hour. Again 0.5 ml of release medium is then removed and the insulin-polymer concentration measured. This process is repeated for release media with glucose concentrations of 100, 200, 400, 800, 1600, and 3200 mg/dl for a total of 8 concentrations over 8 hours. The percent insulin-polymer dissolution at each glucose concentration is then calculated by normalizing the cumulative concentration of insulin-polymer in the release medium as measured by ELISA by that released at 100% gel dissolution. In all cases, 100% dissolution is obtained after the 3200 mg/dl glucose incubation. $G_{10\%}$ and $G_{50\%}$ are then determined by plotting cumulative release curves as a function of glucose concentration and estimating the glucose concentration at which 10% and 50% of the insulin-polymer is released.

Example 13

Size-Exclusion Chromatography

A general method was developed for characterizing lectin compositions with varying degrees of chemical modification on the basis of molecular size using size-exclusion chromatography (SEC). As discussed in Example 40, this method can also be used to separate the component molecules of a single modified lectin composition.

This specific example describes the use of this method in characterizing native and pegylated Con A molecules with different degrees of pegylation. The pegylated Con A compositions were prepared as described in Example 11 but using PEG-SPA-5k reagent instead of PEG-SPA-2k. The following compositions were generated: PEG-5-5k, PEG-7.5-5k, PEG-10-5k, PEG-15-5k, and PEG-20-5k. The final pegylated and native Con A compositions each included 10 mg/ml Con A (based on Con A content without PEG reagent) in 100 mM BES, pH 7, 1.0 M NaCl, 1 mM $MnCl_2$ and 1 mM $CaCl_2$.

20 ul of each solution was injected separately onto a polyacrylamide-based size exclusion resin column (Ultrahydrogel 500, Waters Corp., Milford, Mass.) connected to an HPLC equipped with an absorbance detector measuring at 280 nm and a refractive index detector. The retention times of the peaks were recorded using Breeze software (Waters Corp., Milford, Mass.). The separation mobile phase comprised 50 mM Tris buffer, pH 7.4, at a flow rate of 0.3 ml/min. The Ultrahydrogel column separates proteins on the basis of size, whereby larger molecules have shorter retention times, and smaller molecules have longer retention times in the column.

In a separate experiment, dextran standards of various molecular weights (4-2000 kD, Sigma-Aldrich, St. Louis, Mo.) were run under identical conditions to generate a calibration curve to correlate dextran molecular weight with column retention time. This allowed the native and pegylated Con A sample molecular sizes to be determined as a dextran-equivalent molecular weight. The results for the native Con A and pegylated Con A compositions are shown in Table 2.

Native Con A appeared to be a very compact molecule at a dextran equivalent molecular weight of 3 kD, whereas the pegylated Con A compositions displayed shorter retention times and acted as if they were much larger in size compared to native Con A. The retention time was directly correlated to PEG-Con A size and degree of pegylation, with the highest pegylated compositions giving the shortest retention times.

TABLE 2

Native and modified Con A compositions, their SEC-HPLC retention times and dextran-equivalent molecular weights.

| Sample | PEG:Con A Monomer Molar Ratio | Retention Time (min) | Dextran-Equivalent MW (kDa) |
|---|---|---|---|
| Native Con A | 0.0 | 31.1 | 3 |
| PEG-5.0-5k | 5.0 | 27.1 | 36 |
| PEG-7.5-5k | 7.5 | 26.6 | 51 |
| PEG-10.0-5k | 10.0 | 26.5 | 56 |
| PEG-15.0-5k | 15.0 | 26.2 | 67 |
| PEG-20.0-5k | 20.0 | 25.9 | 135 |

(B) Correlations Between the Presence of Unmodified Lectin Subunits and Mitogenicity Examples 14-18 describe experiments that were performed in order to identify deficiencies in prior art methods for preparing modified lectin compositions. These experiments led us to identify a correlation between the presence of unmodified lectin subunits (as determined by SDS PAGE) and the mitogenicity of modified lectin compositions.

Example 14 describes the preparation of pegylated Con A compositions P44-7 and P26 under inventive conditions. As demonstrated in Example 17, these compositions exhibit very low levels of mitogenicity as compared to the prior art compositions of Examples 15 and 16.

Example 15 describes the preparation of a comparative pegylated Con A composition according to the teachings of Ueno et al., *Cancer Detection and Prevention* 24:100-106, 2000. This sample is referred to herein as P44-4 or the "Ueno sample."

Example 16 describes the preparation of a comparative pegylated Con A composition according to the teachings of Kim and Park, *Pharmaceutical Research* 18:794-799, 2001. This sample is referred to herein as P39 or the "Park sample."

Example 17 describes experiments that identified a correlation between the presence of unmodified lectin subunits (as determined by SDS PAGE) and the mitogenicity of modified lectin compositions. This correlation was observed by comparing the results obtained with a native Con A composition and pegylated Con A compositions P44-7 (Example 14), P26 (Example 14), P44-4 (Ueno sample, Example 15), and P39 (Park sample, Example 16).

Example 18 describes additional experiments that further demonstrate and refine the correlation that was identified in Example 17.

Example 14

Preparation of Pegylated Con A Compositions P44-7 and P26

This example describes the preparation of pegylated Con A compositions P44-7 and P26. P44-7 and P26 were both prepared according to the general procedures described in Example 8, except for the changes in conditions that are described in Table 3.

TABLE 3

Synthesis parameters for modified Con A compositions P44-7 and P26.

| Sample | PEG Reagent | Desired Degree of PEGylation (mol PEG/mol of monomer) | g PEG/g Con A | Buffer | Temperature |
|---|---|---|---|---|---|
| P44-7 | PEG2-10K-NHS | 10 | 4.0 | pH 7 BES | RT |
| P26 | PEG-5K-SPA | 10 | 2.0 | pH 8.5 Borate | 4° C. |

Example 15

Ueno Comparative Example (P44-4)

This example describes the preparation of pegylated Con A composition P44-4. P44-4 was prepared essentially as described in Ueno et al., *Cancer Detection and Prevention* 24:100-106, 2000 for the preparation of their "PEG-Con A (High)" except for the following minor variations. In particular, Ueno et al. used $PEG_2$-CNS-10K as their reagent. This pegylation reagent is no longer commercially available, accordingly, we had to use $PEG_2$-NHS-10K instead. This NHS reagent is much more hydrolytically stable than the CNC reagent used by Ueno et al., and hence a much lower PEG:Con A monomer molar ratio was required to achieve the same degree of pegylation as Ueno et al. The synthesis was carried out in a similar manner to Example 8, except that the for the changes that are described in Table 4.

Briefly, 0.050 g of Con A (Type V, Sigma Aldrich Co., St. Louis, Mo.) was dissolved in 10 ml of 0.2 M borate buffer, pH 10 to give a 5 mg/ml solution of Con A. 0.096 g of the pegylation agent $PEG_2$-NHS-10K was then added to the mixture. This mixture was then stirred at 37 C. for about one hour until the reaction was complete. After 1 hour, the reaction mixture was diluted with 300 ml of PBS at pH 7.4 and the unreacted pegylation agent and salts were removed by ultrafiltration according to methods of Example 9.

TABLE 4

Conditions used in this example, Ueno et al. and Example 8.

| Synthesis Variable | This Example - P44-4 | Ueno et al. | Example 8 |
|---|---|---|---|
| Temperature | 37 C. | 37 C. | 25 C. |
| Reaction Time | 1 hr | 1 hr | 24 hr |
| Buffer | 200 mM Sodium Borate | 200 mM Sodium Borate | 100 mM BES, 1000 mM NaCl 1 mM CaCl2, 1 mM MnCl2 |
| Con A Concentration (mg/mL) | 5 | 5 | 10 |
| Con A Type (Sigma-Aldrich) | Type V | Unknown (Seikagaku) | Type V |

TABLE 4-continued

| Conditions used in this example, Ueno et al. and Example 8. | | | |
|---|---|---|---|
| Synthesis Variable | This Example - P44-4 | Ueno et al. | Example 8 |
| PEG reagent | PEG2-NHS-10k | PEG2-CNC-10k | PEG-SPA-2k |
| PEG:Con A Monomer Molar Ratio Added | 5.000 | 78.000 | range |
| PEG:Con A Monomer Mass Ratio Added | 1.920 | 30 | range |
| PEG:Con A Monomer Molar Ratio by SDS-PAGE | 8-12 | unknown | range |
| Sample name | PEG2-5-10k-Con A | PEG-Con A (High) | — |

The P44-4 composition of this example was then analyzed by SDS-PAGE using the methods of Example 5. The results confirmed that the pegylation linkage and structure of P44-4 are the same as those observed in Ueno et al.

Example 16

Park Comparative Example (P39)

This example describes the preparation of pegylated Con A composition P39. P39 was prepared essentially as described in Kim and Park, *Pharmaceutical Research* 18:794-799, 2001 for the preparation of their "PEG-5-Con A".

The synthesis was carried out in a similar manner to Example 8, except that the conditions were adjusted to closely resemble those found in Kim and Park (see Table 5 below). Briefly, 0.100 g of Con A (Type V, Sigma Aldrich Co., St. Louis, Mo.) was dissolved in 10 ml of 0.1 M borate buffer, pH 8.5 and the solution was kept in an ice bath. The Con A solution was stirred using a magnetic stirrer.

Separately, 0.192 g of the pegylation agent mPEG-NPC-5k was added to 1.92 ml deionized water of the synthesis buffer (100 mM borate buffer, pH 8.5) and used as soon as all of the PEG reagent dissolved. The PEG reagent mixture was then slowly added dropwise using a pipette to the above cooled solution. The amount of pegylation agent was adjusted so that the molar ratio of pegylation agent to Con A monomer (MW 26 kD) was about 5. After addition, the temperature of the reaction mixture was gradually increased from 4 C. to room temperature and the reaction was allowed to continue for 20 hours. At the end of the reaction, the solution was extensively dialyzed as described in Example 10. The resulting solution was then lyophilized to yield pegylated Con A composition P39.

Example 17

Correlation Between Mitogenicity and the Presence of Unmodified Lectin Subunits (Comparative Studies with Prior Art Compositions)

This example demonstrated the existence of a correlation between the results of SDS-PAGE separations and the mitogenicity of Con A compositions. This correlation was observed by comparing the SDS-PAGE and mitogenicity data obtained with a native Con A composition and pegylated Con A compositions P44-7 (Example 14), P26 (Example 14), P44-4 (Ueno, Example 15), and P39 (Park, Example 16).

The mitogenicity of compositions P44-4 and P44-7 were evaluated at 100, 10, and 1 ug/ml as described in Example 1. The SDS-PAGE separations of compositions P44-4 and P44-7 were performed as described in Example 5 using a 4-15% gel.

The mitogenicity of compositions P26 and P39 were evaluated at 1000, 100, 10, 1, 0.1, and 0.01 ug/ml as described in Example 1. The SDS-PAGE separations of P26 and P39 were performed as described in Example 5 using a 15% gel.

FIG. 1 is a plot of the % maximal native mitogenicity against Con A concentration. Included on this same plot is the relevant mitogenicity data for Ueno et al.'s "PEG-Con A (High)" material as obtained from the published results. The plot shows that P44-4 (Ueno comparative sample), Ueno et al.'s published results, and P39 (Park comparative sample) all retain significant mitogenicity, especially at high lectin concentrations (e.g., above 10 ug/ml). In contrast, compositions P44-7 and P26 exhibit less than 10% of the native Con A mitogenicity even at concentrations as high as 100 and 1000 ug/ml.

Figure 2:
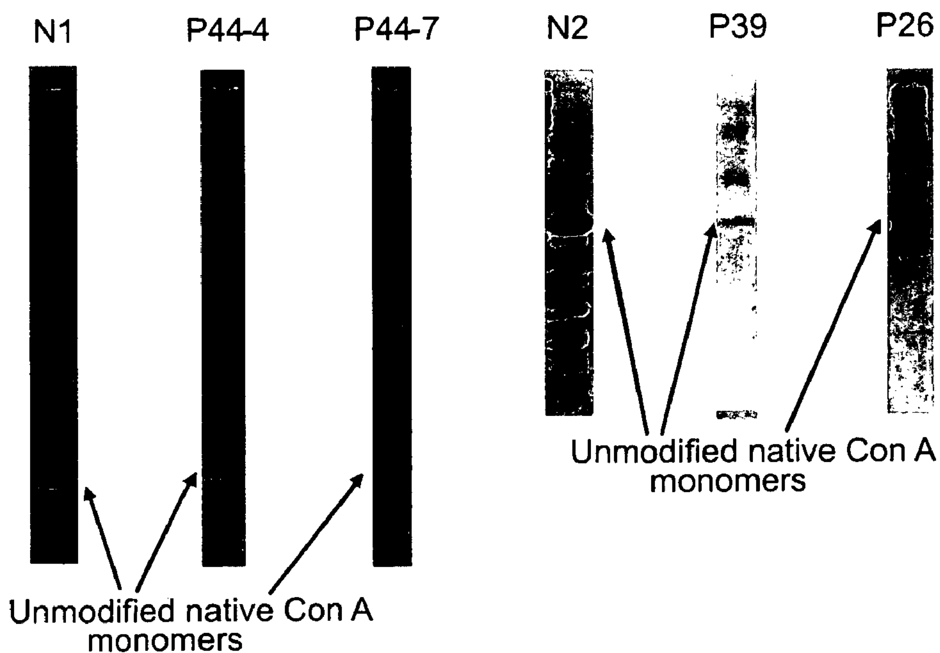
FIG. 2. SDS-PAGE gel images.
Figure 3:
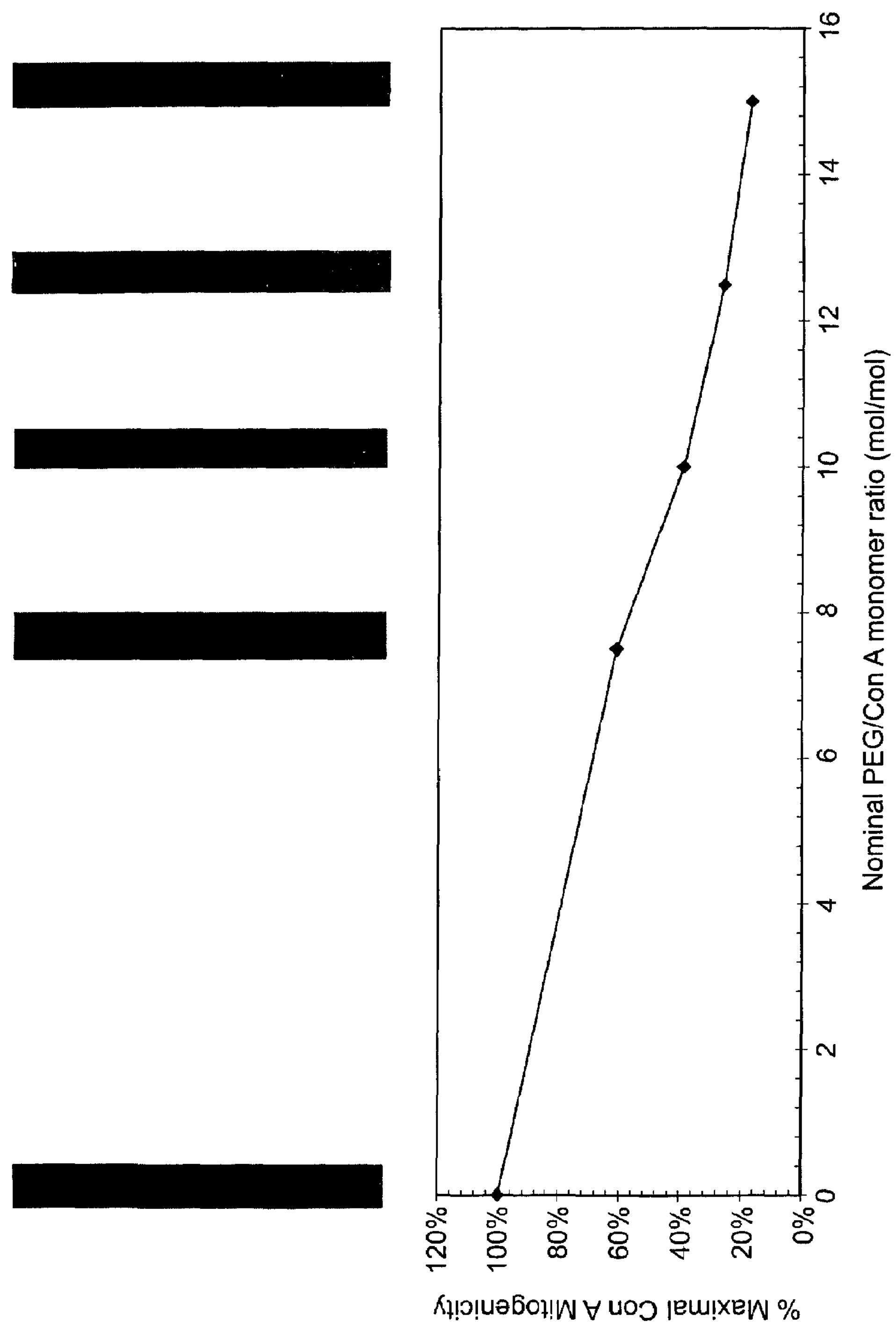
FIG. 3. % maximal Con A mitogenicity vs. desired degree of pegylation with the corresponding SDS-PAGE gel image data for the HT-1 series.
Figure 4:
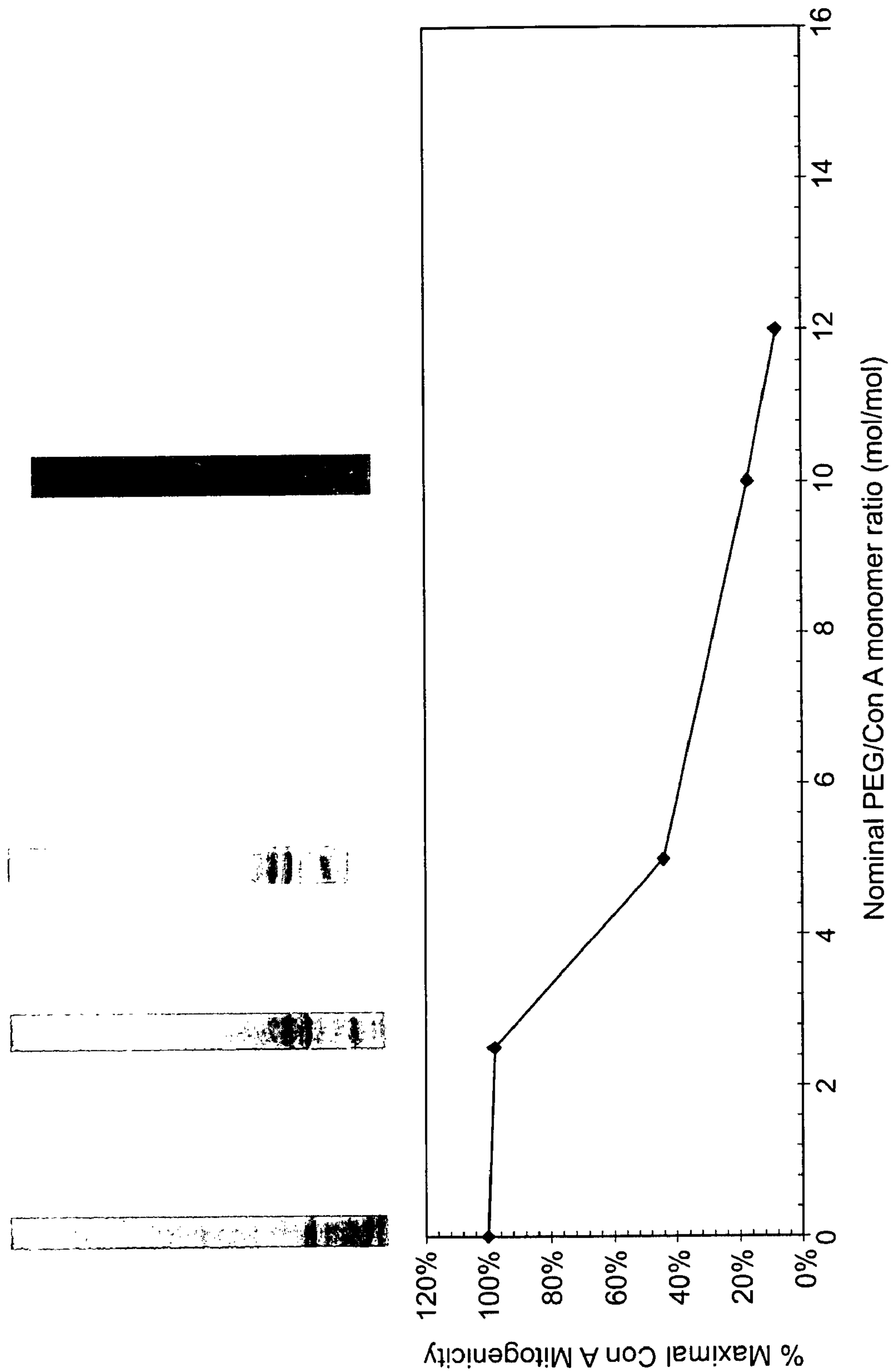
FIG. 4. % maximal Con A mitogenicity vs. desired degree of pegylation with the corresponding SDS-PAGE gel image data for the HT-2 series.
Figure 5:
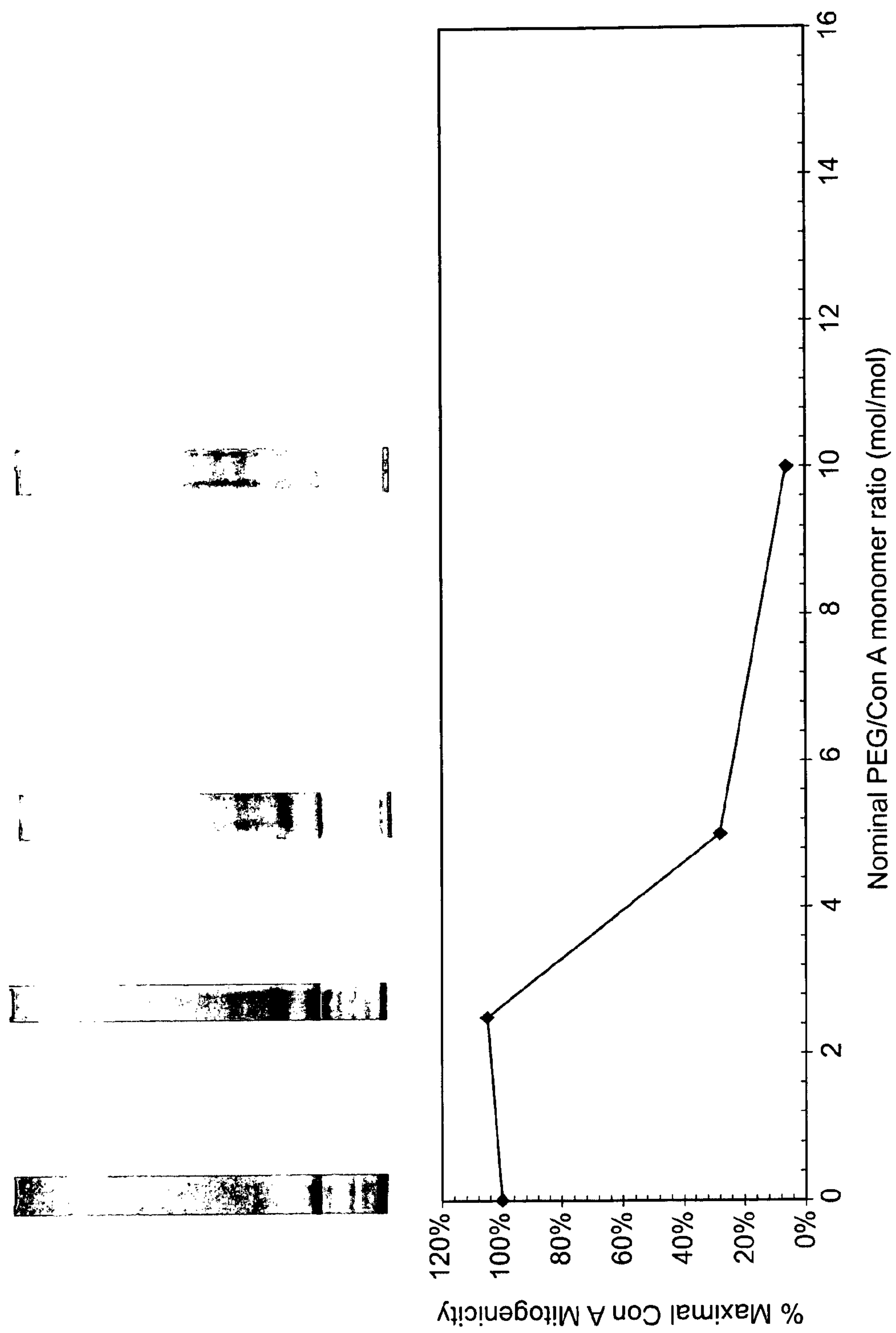
FIG. 5. % maximal Con A mitogenicity vs. desired degree of pegylation with the corresponding SDS-PAGE gel image data for the HT-5 series.
Figure 6:
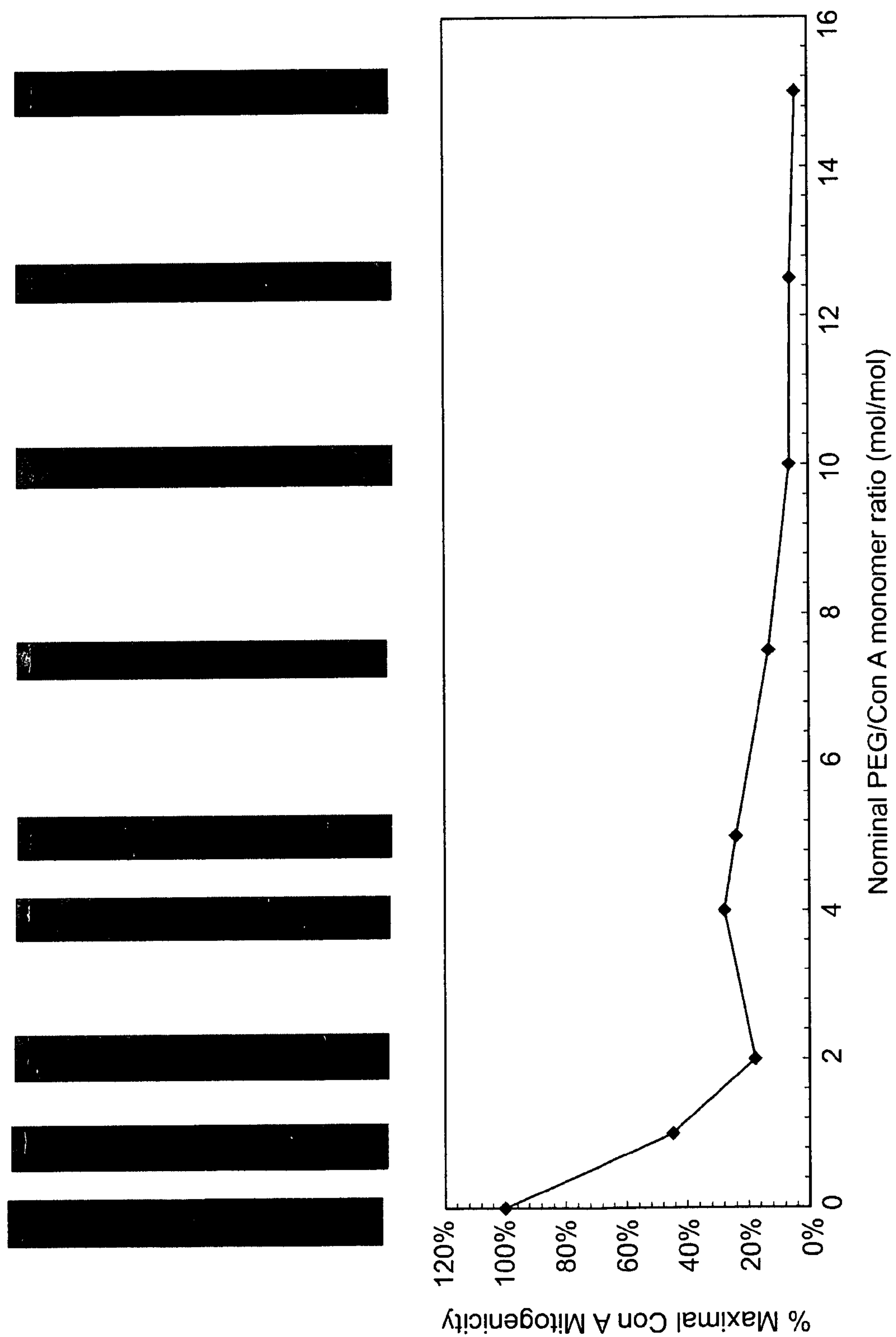
FIG. 6. % maximal Con A mitogenicity vs. desired degree of pegylation with the corresponding SDS-PAGE gel image data for the HT-10 series.

FIG. 2 shows the corresponding SDS-PAGE gel image data for each of the compositions. The "N1" column in FIG. 2 corresponds to the native Con A composition obtained on the 4-15% SDS-PAGE gel. The "N2" column in FIG. 2 corresponds to the native Con A composition obtained on the 15%

TABLE 5

| Conditions used in this example, Park et al. and Example 8. | | | |
|---|---|---|---|
| Synthesis Variable | This Example - P39 | Kim and Park | Example 8 |
| Temperature | 4 C. | 4 C. | 25 C. |
| Reaction Time | 24 hr | 24 hr | 24 hr |
| pH | 8.5 | 8.5 | 7.0-7.4 |
| Buffer | 100 mM Sodium Borate | 100 mM Sodium Borate | 100 mM BES, 1000 mM NaCl 1 mM CaCl2, 1 mM MnCl2 |
| Con A Concentration (mg/mL) | 10 | 10 | 10 |
| Con A Type (Sigma Aldrich) | Type V | Type IV | Type V |
| PEG reagent | PEG-NPC-5k | PEG-NPC-5k | PEG-SPA-2k |
| PEG:Con A Monomer Molar Ratio Added | 5.000 | 5.000 | range |
| PEG:Con A Monomer Mass Ratio Added | 1.923 | 1.923 | range |
| PEG:Con A Monomer Molar Ratio by SDS-PAGE | 3.4 | Unknown | range |
| Sample name | PEG-5-5k-Con A | PEG-5-Con A | — |

SDS-PAGE gel. As discussed, under physiological conditions, Con A is a tetramer of about 104 kD. SDS-PAGE denatures the tetramer into its constituent monomers of about 26 kD. The arrows in FIG. 2 indicate the location of the native monomer band in the "N1" and "N2" columns. The lighter bands at lower MW are peptide fragments that are found in all commercial Con A preparations. The remaining columns correspond to pegylated Con A compositions P44-4, P44-7, P39 and P26. As compared to the "N1" and "N2" columns, these columns include heavier bands that correspond to pegylated Con A monomers. The heavier bands become more prominent as the degree of pegylation increases.

Surprisingly, despite performing the pegylation with a relatively high PEG:Con A monomer ratio, the modified Con A compositions P44-4 (Ueno sample) and P39 (Park sample) were both found to include a significant native Con A component (see arrows in FIG. 2). These results indicate that a substantial number of Con A monomers did not react at all under the prior art pegylation conditions. Inventive compositions P44-7 and P26, on the other hand, were found to have very little native band remaining. This finding is significant in light of the fact that P44-7 and P26 both exhibit dramatically reduced mitogenicity as compared to native Con A and modified compositions P44-4 and P39 (see FIG. 1). Thus, it appears that the residual mitogenicity of modified compositions P44-4 and P39 (and modified lectin compositions in general) is due at least in part to the presence of a significant amount of unmodified lectin monomers. Without wishing to be bound to any particular theory, we suggest that the degree of monomer association (and further aggregation between multimers) may influences the uniformity of lectin modification by influencing the uniformity of monomer accessibility. Thus conditions that disrupt monomer and/or multimer association and yet allow modification reactions to occur at a reasonable rate are likely to be preferred conditions for preparing modified lectins with reduced mitogenicity. The reaction conditions of Example 14 (used to prepare compositions P44-7 and P26) are examples of such preferred conditions.

Example 18

Correlation Between Mitogenicity and the Presence of Unmodified Lectin Subunits (Comparative Studies with Compositions)

This example builds on the results of Example 17 by comparing the mitogenicity and SDS-PAGE separations of a family of pegylated Con A compositions (HT-1-7.5, 10, 12.5, 15; HT-2-2.5, 5, 10, 12; HT-5-2.5, 5, 10; and HT-10-1, 2, 4, 5, 7.5, 10, 12.5, 15). Each of the pegylated compositions was synthesized according to the generalized procedure of Example 11. Table 6 shows the type of PEG reagent, desired degree of pegylation, and mass of PEG reagent used for each the pegylated Con A compositions.

TABLE 6

Synthesis parameters for modified Con A compositions HT-1, HT-2, HT-5, and HG-10 series.

| Sample | PEG Reagent | Desired Degree of PEGylation (mol PEG/mol of monomer) | g PEG/g Con A |
|---|---|---|---|
| Con A | n/a | n/a | n/a |
| HT-1-7.5 | PEG-SMB-1K | 7.5 | 0.3 |
| HT-1-10 | PEG-SMB-1K | 10 | 0.4 |
| HT-1-12.5 | PEG-SMB-1K | 12.5 | 0.5 |
| HT-1-15 | PEG-SMB-1K | 15 | 0.6 |
| HT-2-2.5 | PEG-SPA-2K | 2.5 | 0.2 |
| HT-2-5 | PEG-SPA-2K | 5 | 0.4 |
| HT-2-10 | PEG-SPA-2K | 10 | 0.8 |
| HT-2-12 | PEG-SPA-2K | 12 | 1.0 |
| HT-5-2.5 | PEG-SPA-5K | 2.5 | 0.5 |
| HT-5-5 | PEG-SPA-5K | 5 | 1.0 |
| HT-5-10 | PEG-SPA-5K | 10 | 2.0 |
| HT-10-1 | PEG2-NHS-10K | 1 | 0.4 |
| HT-10-2 | PEG2-NHS-10K | 2 | 0.8 |
| HT-10-4 | PEG2-NHS-10K | 4 | 1.6 |
| HT-10-5 | PEG2-NHS-10K | 5 | 2.0 |
| HT-10-7.5 | PEG2-NHS-10K | 7.5 | 3.0 |
| HT-10-10 | PEG2-NHS-10K | 10 | 4.0 |
| HT-10-12.5 | PEG2-NHS-10K | 12.5 | 5.0 |
| HT-10-15 | PEG2-NHS-10K | 15 | 6.0 |

The mitogenicity of each material was evaluated at 100, 10, and 1 ug/ml as described in Example 1. The SDS-PAGE separations were performed as described in Example 5. FIGS. 3 through 6 show plots of the % maximal native mitogenicity against desired degree of pegylation with the corresponding SDS-PAGE gel images for each of the HT-1, HT-2, HT-5, and HT-10 series, respectively.

The plots show that for each type of PEG reagent, a reduction in % Con A maximal mitogenicity is strongly correlated with the presence of higher MW bands in the SDS-PAGE (i.e., higher degrees of pegylation). As was the case in Example 17, most of the modified Con A compositions were found to include a significant native Con A component. In the HT-2, HT-5, and HT-10 series, far fewer native Con A monomers are present in the higher pegylated samples as compared to the lower pegylated samples suggesting that the pegylation of Con A monomers was substantially more uniform in the high PEG:Con A ratio regime than in the lower regime. This finding is significant in light of the fact that all of these samples had dramatically reduced mitogenicity as compared to native Con A and modified compositions with a nominal PEG:Con A ratio <10. Thus, it appears that the residual mitogenicity of modified compositions HT-2-2.5, HT-2-5, HT-5-2.5, HT-5-5, and HT-10-1, 2, 4, 5 and 7.5 (and modified lectin compositions in general) is due at least in part to the presence of unmodified lectin monomers.

Based on the results of Examples 17 and 18 we have provided methods for reducing the mitogenicity of lectin compositions that involves (a) selecting conditions that ensure the uniform modification of lectin monomers (as with HT-2-10, HT-5-10, and HT-10-10 in this example and as further described in Examples 14 and 21) and/or (b) treating the compositions by removing unmodified lectin monomers after chemical modification (e.g., as described in Examples 22-24).

(C) Effect of Lectin Modification on Saccharide Binding

Example 19 describes the preparation of pegylated Con A compositions P24-P29, P62, and P64 under inventive conditions. These compositions were then assessed for mitogenicity and monosaccharide binding. Regardless of the extent of pegylation and the resulting decrease in mitogenicity all compositions were found to have a preserved, or in some cases improved, saccharide binding affinity.

Example 20 describes the polysaccharide binding properties of the pegylated Con A compositions P62 and P64 of Example 19. Both P62 and P64 exhibited measurable binding affinities for the polysaccharides tested.

Example 19

Effect of Pegylation on Monosaccharide Binding

This example compares the monosaccharide binding affinities and mitogenicity values of a native Con A composition and pegylated Con A compositions P24-P29, P62, and P64. Each of the pegylated compositions was synthesized according to the generalized procedure described in Example 8. Table 7 shows the type of PEG reagent, desired degree of pegylation, mass of PEG reagent, buffer type, etc. used for each these compositions. Note that in some of the preparations (e.g., P25, P27 and P29), α-methyl mannose was included in the reaction mixture. Note further that P28 and P29 are, respectively, the results of two of the same and different rounds of modification (i.e., they are both derived from "pre-modified" Con A compositions as shown in Table 7).

TABLE 7

Conditions used in preparing pegylated Con A compositions P24-P29, P62, and P64.

| Sample | PEG Reagent | Desired Degree of PEGylation (mol PEG/mol of monomer) | g PEG/g Con A | Buffer | Temperature | Protection with alpha-methyl-mannose | Starting Material |
|---|---|---|---|---|---|---|---|
| P24 | PEG2-10K-NHS | 26 | 10.0 | pH 8.5 Borate | RT | − | Con A |
| P25 | PEG2-10K-NHS | 26 | 10.0 | pH 8.5 Borate | RT | + | Con A |
| P26 | PEG-5K-SPA | 10 | 2.0 | pH 8.5 Borate | 4° C. | − | Con A |
| P27 | PEG-5K-SPA | 10 | 2.0 | pH 8.5 Borate | 4° C. | + | Con A |
| P28 | PEG-2K-SPA | 5 | 1.0 | pH 8.5 Borate | 4° C. | − | PEG-5-2K Con A (RT, BES) |
| P29 | PEG-2K-SPA | 5 | 1.0 | pH 8.5 Borate | 4° C. | + | PEG-5-2K Con A (4° C., Borate) |
| P62 | PEG-5K-SPA | 10 | 2.0 | pH 7 BES | RT | − | Con A |
| P64 | PEG-2K-SPA | 10 | 0.8 | pH 7 BES | RT | − | Con A |

The mitogenicity of each sample was then evaluated as described in Example 1. The evaluation was performed over a broader range of concentrations than in previous examples, namely at 1000, 100, 10, 1, 0.1 and 0.01 ug/ml. The binding constant of each composition for α-methyl mannose and/or mannotriose was also evaluated as described in Example 4.

Table 8 shows the % maximal native mitogenicity over all evaluated concentrations and the corresponding binding affinities for α-methyl mannose and/or mannotriose. Regardless of the extent of pegylation and the resulting decrease in mitogenicity all compositions have a preserved, or in some cases improved, binding affinity.

TABLE 8

Comparison of mitogenicity and binding affinity for pegylated Con A compositions.

| Sample | % maximal Con A mitogenicity | Ka for alpha-methyl-mannose (1/M) | Ka for mannotriose (1/M) |
|---|---|---|---|
| Con A | 100 | 6860 | n/a |
| P24 | 5 | 18400 | n/a |
| P25 | 4 | 25400 | n/a |
| P26 | 4 | 15600 | n/a |
| P27 | 4 | 14200 | n/a |
| P28 | 5 | 12500 | n/a |
| P29 | 5 | 13200 | n/a |
| P62 | 5 | 6283 | 93800 |
| P64 | 17 | n/a | 93000 |

Example 20

Effect of Pegylation on Polysaccharide Binding

This example compares the polysaccharide binding properties of the pegylated Con A compositions P62 and P64 of Example 19. The binding affinity of each composition for yeast mannan, dextran 10K, and dextran 70K was evaluated as described in Example 4. Table 9 shows the % maximal native mitogenicity (as determined in Example 19) and the corresponding binding affinities for the various polysaccharides. Both P62 and P64 exhibit measurable binding affinities for the polysaccharides tested.

TABLE 9

Mitogenicity and polysaccharide binding affinities for pegylated Con A compositions P62 and P64.

| Sample | % maximal Con A mitogenicity | Ka for Mannan (1/M) | Ka for Dextran 10K (1/M) | Ka for Dextran 70K (1/M) |
|---|---|---|---|---|
| P62 | 5 | 1710 | 8930 | 5593 |
| P64 | 17 | 2690 | 9000 | 8650 |

(D) Effect of Linker Chemistry and Buffer on Degree of Pegylation

Example 21 describes the high throughput synthesis of pegylated Con A compositions using different reagent linker chemistries and buffers. The effect of the different chemistries on the degree of pegylation (as measured by SDS-PAGE) and glycogen precipitation were assessed.

Example 21

Linker Chemistry and Buffer

Pegylated Con A compositions were synthesized according to the methods of Example 11, except for the following changes. A 2×4×6 experimental design was constructed to examine buffer choice {100 mM BES, pH 7, 1.0 M NaCl, 1 mM $MnCl_2$, 1 mM $CaCl_2$; 100 mM sodium borate, pH 8.2}, PEG:Con A monomer molar ratio added to the reaction {PEG-5.0, PEG-7.5, PEG-10.0, PEG-12.5}, and linker chemistry type {SPA, SBA, SMB, NHS, CNC, and NPC}. In this example PEG molecular weight was 5 kD for all PEG linker chemistry types. The synthesis scheme is provided in Table 10.

Figure 7:
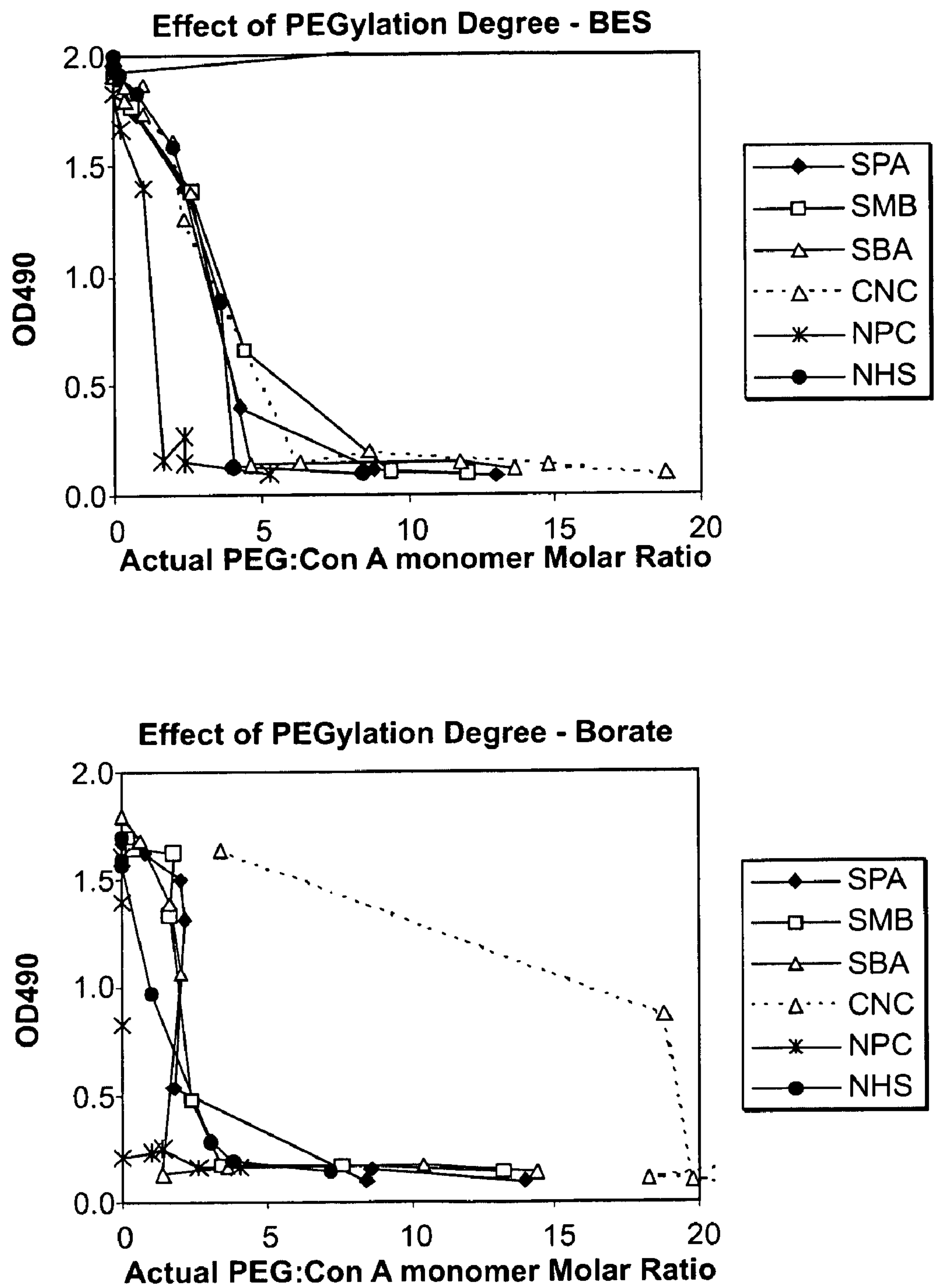
FIG. 7. Effect of PEG:Con A monomer molar ratio, buffer choice, and linker chemistry on the glycogen precipitation assay performed according to Example 7.

Briefly, 0.6 g of Con A was dissolved into the appropriate borate or BES buffers and pipetted into a 24-well plate, with each well receiving 1 ml of the appropriate Con A stock solution as shown in Table 10. The reaction plates were cooled to 4 C. in a refrigerator before addition of the PEG reagents. Next, the individual PEG reagents, PEG-SPA-5k, PEG-SBA-5k, PEG-SMB-5k, PEG-NHS-5k, PEG-NPC-5k, and PEG-CNC-5k (all from Sigma Aldrich, St. Louis, Mo.) were added. Once dissolved, the individual PEG reagents were used quickly to minimize hydrolysis, and the volumes and types of each PEG solution are shown in Table 10. The wells were allowed to react overnight, and the next day an SDS-PAGE analysis (see Example 5) and a glycogen precipitation assay (see Example 7) were performed on the contents of each well. The results of these assays are displayed in FIG. 7.

Overall it appeared that the SPA, SMB and SBA linker chemistries all performed equally, with glycogen precipitation seeming to decrease significantly above PEG-5-5k (actual not the nominal amount used in the reaction) and giving similar results with both buffers. CNC behaved in a like manner with the BES buffer, but led to very different glycogen precipitation results and to high molecular weight bands during the SDS-PAGE analysis with the borate buffer, possibly due to unwanted crosslinking reaction. The NPC chemistry (the preferred linker chemistry of Kim and Park, see Example 16) led to materials that were unable to precipitate glycogen, even at low PEG:Con A monomer molar ratios. It was also noted that the NPC linker did not give rise to any PEG:Con A monomer molar ratios of greater than 5, despite the fact that in some cases the nominal PEG:Con A monomer molar ratio was as high as 12.5.

TABLE 10

Experimental design and liquid volumes for the investigation into PEG-5k linker chemistry.

| Well ID | Con A/ Buffer | Amount of Con A Sol'n (mL) | PEG-5k Linker | Amount of PEG solution (mL) | PEG: Con A monomer ratio |
|---|---|---|---|---|---|
| 1 | BES | 1 | SPA | 0.417 | 12.5 |
| 2 | BES | 1 | SPA | 0.334 | 10 |
| 3 | BES | 1 | SPA | 0.250 | 7.5 |
| 4 | BES | 1 | SPA | 0.167 | 5 |
| 5 | BES | 1 | SMB | 0.417 | 12.5 |
| 6 | BES | 1 | SMB | 0.334 | 10 |
| 7 | BES | 1 | SMB | 0.250 | 7.5 |
| 8 | BES | 1 | SMB | 0.167 | 5 |
| 9 | BES | 1 | SBA | 0.417 | 12.5 |
| 10 | BES | 1 | SBA | 0.334 | 10 |
| 11 | BES | 1 | SBA | 0.250 | 7.5 |
| 12 | BES | 1 | SBA | 0.167 | 5 |
| 13 | BES | 1 | CNC | 0.417 | 12.5 |
| 14 | BES | 1 | CNC | 0.334 | 10 |
| 15 | BES | 1 | CNC | 0.250 | 7.5 |
| 16 | BES | 1 | CNC | 0.167 | 5 |

TABLE 10-continued

Experimental design and liquid volumes for the investigation into PEG-5k linker chemistry.

| Well ID | Con A/ Buffer | Amount of Con A Sol'n (mL) | PEG-5k Linker | Amount of PEG solution (mL) | PEG: Con A monomer ratio |
|---|---|---|---|---|---|
| 17 | BES | 1 | NPC | 0.417 | 12.5 |
| 18 | BES | 1 | NPC | 0.334 | 10 |
| 19 | BES | 1 | NPC | 0.250 | 7.5 |
| 20 | BES | 1 | NPC | 0.167 | 5 |
| 21 | BES | 1 | NHS | 0.417 | 12.5 |
| 22 | BES | 1 | NHS | 0.334 | 10 |
| 23 | BES | 1 | NHS | 0.250 | 7.5 |
| 24 | BES | 1 | NHS | 0.167 | 5 |
| 25 | Borate | 1 | SPA | 0.417 | 12.5 |
| 26 | Borate | 1 | SPA | 0.334 | 10 |
| 27 | Borate | 1 | SPA | 0.250 | 7.5 |
| 28 | Borate | 1 | SPA | 0.167 | 5 |
| 29 | Borate | 1 | SMB | 0.417 | 12.5 |
| 30 | Borate | 1 | SMB | 0.334 | 10 |
| 31 | Borate | 1 | SMB | 0.250 | 7.5 |
| 32 | Borate | 1 | SMB | 0.167 | 5 |
| 33 | Borate | 1 | SBA | 0.417 | 12.5 |
| 34 | Borate | 1 | SBA | 0.334 | 10 |
| 35 | Borate | 1 | SBA | 0.250 | 7.5 |
| 36 | Borate | 1 | SBA | 0.167 | 5 |
| 37 | Borate | 1 | CNC | 0.417 | 12.5 |
| 38 | Borate | 1 | CNC | 0.334 | 10 |
| 39 | Borate | 1 | CNC | 0.250 | 7.5 |
| 40 | Borate | 1 | CNC | 0.167 | 5 |
| 41 | Borate | 1 | NPC | 0.417 | 12.5 |
| 42 | Borate | 1 | NPC | 0.334 | 10 |
| 43 | Borate | 1 | NPC | 0.250 | 7.5 |
| 44 | Borate | 1 | NPC | 0.167 | 5 |
| 45 | Borate | 1 | NHS | 0.417 | 12.5 |
| 46 | Borate | 1 | NHS | 0.334 | 10 |
| 47 | Borate | 1 | NHS | 0.250 | 7.5 |
| 48 | Borate | 1 | NHS | 0.167 | 5 |

(E) Removal of Unmodified Lectin Subunits Further Reduces the Mitogenicity of Modified Lectin Compositions Examples 22-24 describe experiments that demonstrate the benefits of removing native subunits and/or subunits with low degrees of chemical modification from modified lectin compositions. Specifically, these experiments demonstrate that such removal steps can be used to further reduce the mitogenicity of modified lectin compositions.

Example 22 describes the use of ion exchange chromatography.

Example 23 describes the use of column affinity chromatography.

Example 24 describes the use of affinity chromatography with beads in solution.

Example 22

Ion Exchange Chromatography

Some of the inventive pegylated Con A compositions were further purified using ion-exchange chromatography in order to remove native Con A subunits and modified Con A subunits with low degrees of pegylation. Specifically, P19 was synthesized according to the general methods described in Example 8 using PEG-SPA-2k at a PEG:Con A monomer ratio of 5 in a pH 7 BES buffer at room temperature and then purified and lyophilized according to Example 7. The lyophilized P19 powder was then reformulated at 10 mg/ml in 10 mM sodium acetate, pH 4.5. Under these conditions, it is known by those skilled in the art that Con A undergoes a phase transition from a predominantly tetrameric quaternary structure to a primarily dimeric quaternary structure. The resulting solution was stirred and then centrifuged at 3,000×g for 10 minutes (Allegra 21R, Beckman Coulter, Fullerton, Calif.) to remove a small fraction of insoluble mass. The supernatant was then chromatographed at room temperature using a HPLC (Waters Breeze System, Milford, Mass.) connected to a 8 mm×7.8 cm SP-5PW cation exchange column (Tosoh Biosciences, Montgomeryville, Pa.) using a gradient method. Two mobile phases were used, mobile phase A containing 10 mM sodium acetate (pH 4.5) and mobile phase B containing 10 mM sodium acetate (pH 4.5) and 1.0 M sodium chloride. The gradient that gave optimal separation between modified and unmodified subunits was found to be a linear ramp from 100% A to 70:30% A:B over 60 minutes. The desired fractions were then collected, dialyzed against deionized water to remove sodium chloride, and lyophilized.

Figure 8:
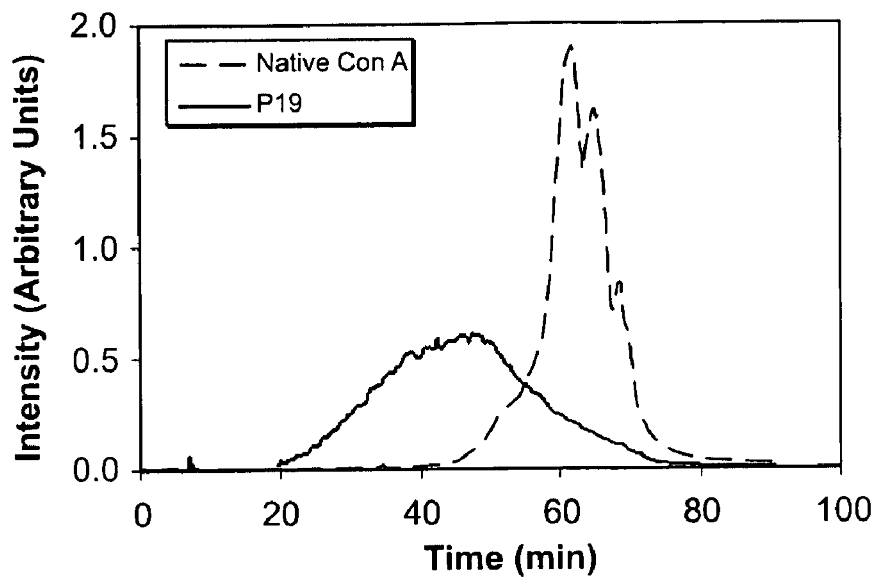
FIG. 8. Ion-exchange HPLC chromatograms of modified Con A formulation (black) and native Con A (blue).
Figure 9:
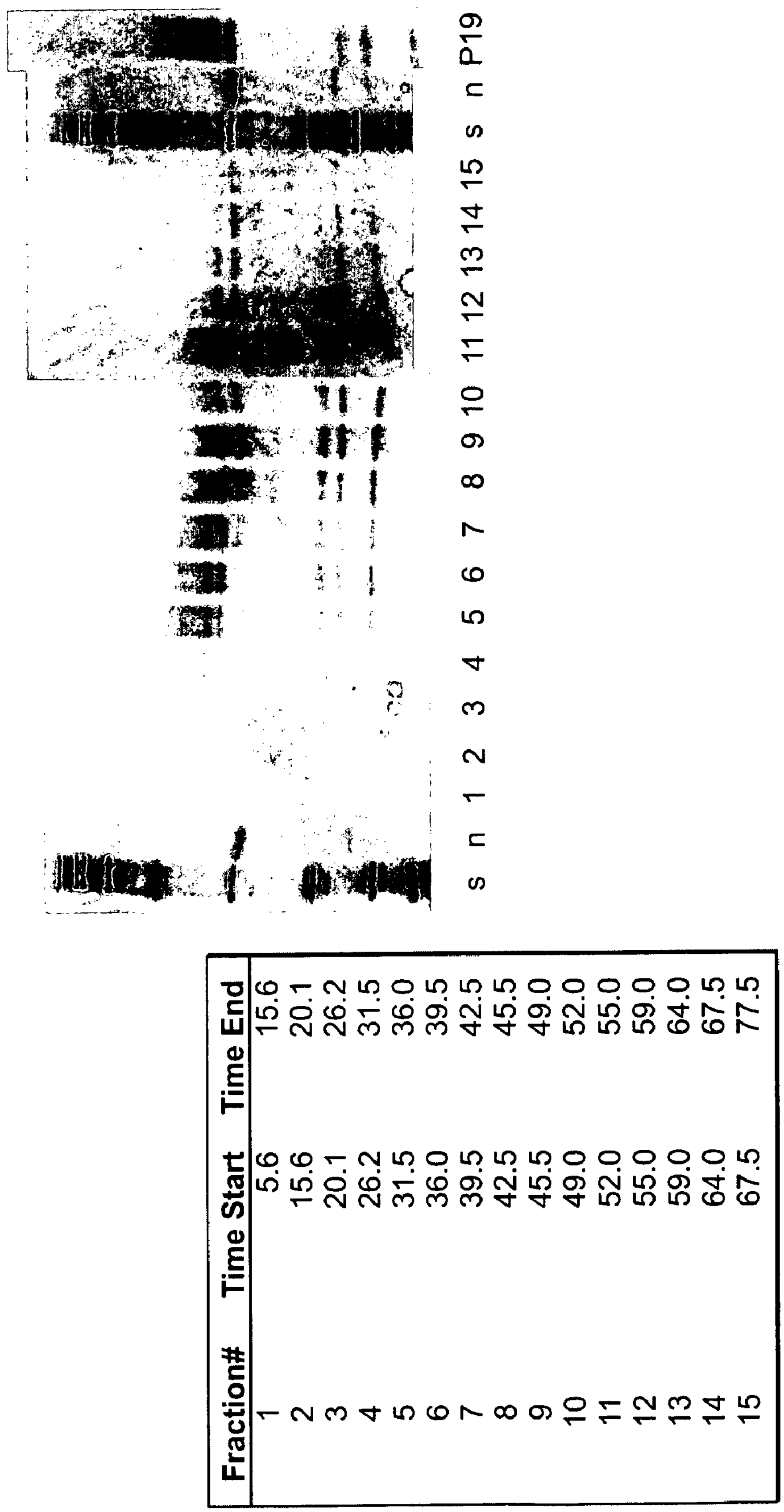
FIG. 9. Ion-Exchange separation fractions, chromatogram times (in minutes) and SDS-PAGE analysis on chromatographic fractions. The presence of the native band of Con A (~26 kDa) correlates with the native Con A set of peaks in the chromatogram. Fractions 4-7 are substantially free of the native Con A subunit.

FIG. 8 compares the chromatograms of the P19 and native Con A compositions over time. Fifteen fractions were taken from the P19 composition. FIG. 9 shows the SDS-PAGE gels that were obtained from each of these fifteen fractions (lanes 1-15) and the native Con A composition (lane "n"). Fractions 1-3 were devoid of any material. Fractions 4-7 included Con A subunits with high degrees of pegylation and showed no bands at the molecular weight for native unmodified Con A subunits (compare lanes 4-7 with lane "n"). In contrast, intermediate fractions 8-11 contained a mixture of modified and unmodified subunits while the later fractions 13-14 contained predominantly unmodified subunits.

Example 23

Affinity Chromatography Using a Column

Modified lectin compositions are further purified using column affinity chromatography. The lyophilized powders are dissolved at 10 mg/ml in 100 mM BES buffer, pH 7.0, 1.0 M NaCl, 1 mM $MnCl_2$, and 1 mM $CaCl_2$. The solutions are passed through an affinity column (Pharmacia, Groton, Conn.) packed with mannan-agarose beads (Sigma Aldrich, St. Louis, Mo.) at 1 ml/min using a mobile phase of 100 mM BES buffer, pH 7.0, 1.0 M NaCl, 1 mM $MnCl_2$, and 1 mM $CaCl_2$. The column can be connected to a HPLC (Waters Breeze System, Milford, Mass.) equipped with a UV-VIS detector set at 280 nm to measure protein content of the mobile phase. The basis for the affinity separation is that native Con A and subunits with low degrees of pegylation have a higher binding affinity for mannose-containing polysaccharides (such as mannan) than do subunits with high degrees of pegylation. The native and lower pegylated subunits will therefore release from a polysaccharide column under higher glucose conditions than the more pegylated subunits.

Under the above conditions, a significant portion of the modified Con A composition (including native, low pegylation and high pegylation subunits) will bind to the column and some fraction may pass through the column unbound. This fraction, A, will be discarded. Likewise, the mobile phase buffer can then be altered to include 50 mg/dl of glucose, and the column containing bound modified Con A will be allowed to equilibrate, after which a portion of the bound protein will again be eluted from the column and discarded (fraction B). The buffer can then be altered a second time to include a concentration of glucose (e.g., about 800 mg/dl) sufficient to release the highly pegylated subunits (fraction C). This fraction will be saved, and will contain modified Con A subunits that are substantially free of native Con A subunits and modified Con A subunits with low degrees of pegylation. Finally, the buffer will be altered a fourth time to include 0.1 M methyl-α-mannopyrannoside, a potent inhibitor of Con A binding. After the column is equilibrated, another smaller fraction (fraction D) will be eluted from the column that is enriched in the native Con A and modified Con A with low degrees of pegylation. The fractions A-D will be assayed by SDS-PAGE. The expected results for the P64 composition of Example 19 are shown in Table 11 (see also Example 24).

TABLE 11

Expected SDS-PAGE results for pegylated Con A composition P64 after affinity separation.

| Fraction | Glucose Concentration (mg/dl) | Ratio of SDS-PAGE line densities (MW < PEG-5-5k/MW > PEG-5-5k) (%) |
|---|---|---|
| Initial mixture (P64) | — | 5.0% |
| A | 0 | 0.1% |
| B | 50 | 0.2% |
| C | 800 | 0.4% |
| D | 0.1 M Me-α-Man | 25.0% |

Example 24

Affinity Chromatography Using Beads in Solution

Modified Con A stock solutions were made by dissolving lyophilized P62 or P64 from Example 19 in 100 mM BES buffer, pH 7.0, 1.0 M NaCl, 1 mM $MnCl_2$, and 1 mM $CaCl_2$ so that the final protein content on a Con A equivalent (i.e., the mass of the modified Con A without the weight of the PEG groups) was 5 mg/ml. 0.3 ml of the P62 and P64 solutions were then each mixed with 0.3 ml of ~400 mg/ml mannan-agarose bead suspension (Sigma Aldrich, St. Louis, Mo.) pre-equilibrated with the same buffer as the P62 and P64 solutions. The suspensions were vortexed briefly at room temperature and P62 and P64 were allowed to bind to their respective beads for 1 hour. The beads were centrifuged (Allegra 21R, Beckman Coulter, Fullerton, Calif.) at 2000×g for 10 minutes. The supernatant was removed and discarded, and the beads were washed 3× with 100 mM BES buffer, pH 7.0, 1.0 M NaCl, 1 mM $MnCl_2$, and 1 mM $CaCl_2$ and centrifuged 3× to obtain beads that contained only bound P62 or P64.

Figure 10:
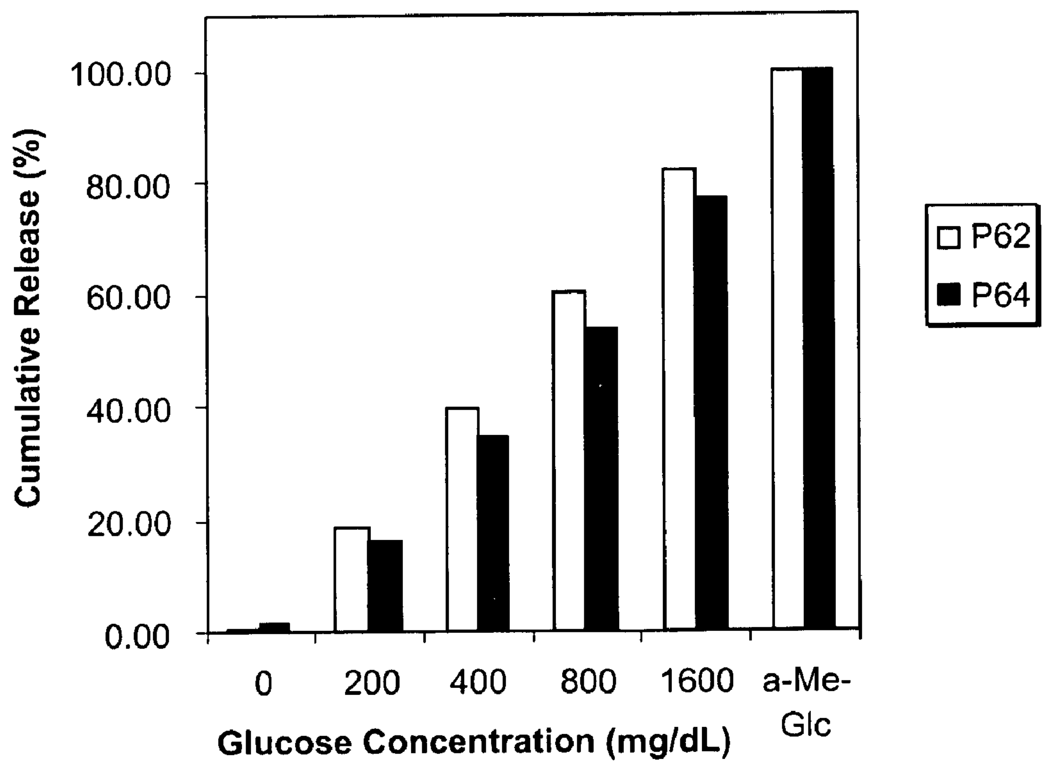
FIG. 10. Cumulative release of bound P62 and P64 modified Con A formulations at various glucose and methyl-α-glucoside concentrations. (100%=total amount released after using 0.1 M methyl-α-glucoside).

0.3 ml of fresh buffer was added back to the beads and the mixture was vortexed again. The beads were centrifuged as above, and 150 ul of the supernatant was removed via pipette and placed into the well of a UV-transparent 96-well microtiter plate (VWR Scientific, Bridgeport, N.J.). An aliquot of 0.3 ml of a 400 mg/dl glucose solution in 100 mM BES buffer, pH 7.0, 1.0 M NaCl, 1 mM $MnCl_2$, and 1 mM $CaCl_2$ was added to give a final concentration of 200 mg/dl glucose solution when mixed with the 150 ul bead suspension. The bead suspension was revortexed, and the P62 or P64 was allowed to bind for 15 minutes. The bead suspension was centrifuged, and 150 ul of the supernatant was pipetted out of the vial and placed into another well on the 96-well plate. The process was repeated to assay binding at 400, 800, and 1600 mg/dl glucose solutions. The process was repeated a final time using a solution of 0.1 M methyl-α-D-mannopyranoside, which is a potent inhibitor of the Con A binding site. The individual wells of the 96-well plate were assayed for their optical density at a wavelength of 280 nm, in order to characterize the protein content of each well using a commercially available plate reader (SpectraMAX, Molecular Devices, Mountain View, Calif.). The results of the binding example are shown below in FIG. 10.

(F) Other Notable Correlations Between the Properties of Modified Lectin Compositions and Their Reduced Mitogenicity Example 25 demonstrates that chemical compounds with greater molecular weights are most effective in reducing the mitogenicity of lectins.

Example 26 discusses experiments that highlight a correlation between the MAC of a modified lectin composition and its mitogenicity. Specifically, these experiments demonstrate that modified lectin compositions with a MAC above a threshold of about 6 ug/ml exhibit less than 5% of the maximal Con A mitogenicity even at the highest concentrations evaluated.

Example 27 describes a correlation that we have observed between the glycogen precipitation properties of modified lectin compositions and their mitogenicity. Specifically, a reduction in % Con A maximal mitogenicity was found to be strongly correlated with the ability of each modified Con A composition to precipitate glycogen.

Example 25

Correlation Between PEG MW and Mitogenicity

Figure 11:
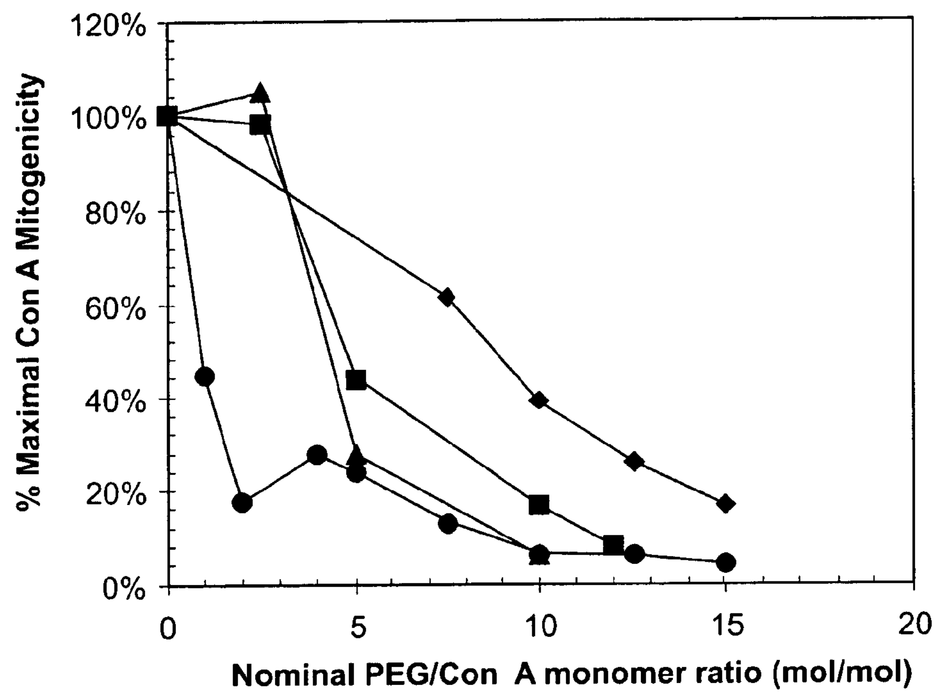
FIG. 11. % maximal Con A mitogenicity vs. desired degree of pegylation for (♦) HT-1 MW 1K, (■) HT-2 MW 2K, (▲) HT-5 MW 5K, and (●) HT-10 MW 10K.

This example compares the % maximal native mitogenicity for modified Con A compositions as a function of degree of PEG substitution for four different MW PEG reagents (1K: HT-1-7.5, 10, 12.5, 15; 2K: HT-2-2.5, 5, 10, 12; 5K: HT-5-2.5, 5, 10; and 2×5K HT-10-1, 2, 4, 5, 7.5, 10, 12.5, 15). Each of the pegylated compositions was synthesized according to the procedures of Example 18. The mitogenicity of each material was evaluated at 100, 10, and 1 ug/ml as described in Example 1. FIG. 11 is a plot of the % maximal native mitogenicity against desired degree of pegylation for each of the HT-1, HT-2, HT-5, and HT-10 series. The plot shows that for a given level of desired degree of pegylation, the larger MW PEG reagents are more effective in reducing the % maximal native mitogenicity Example 26

Correlation Between MAC and Mitogenicity

Figure 12:
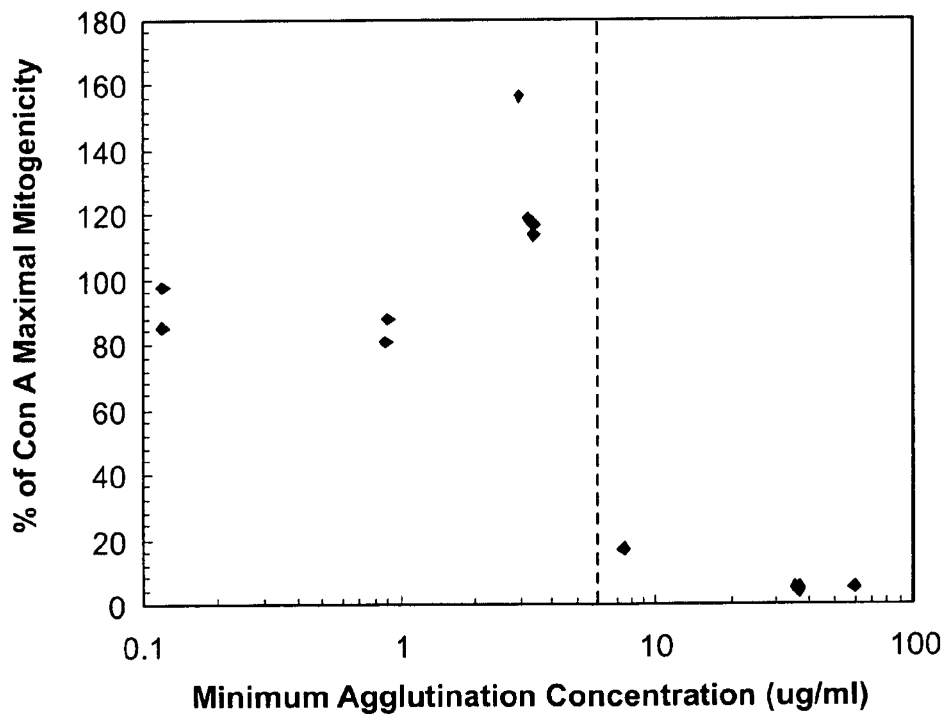
FIG. 12. Correlation between MAC and % maximal Con A mitogenicity
Figure 13:
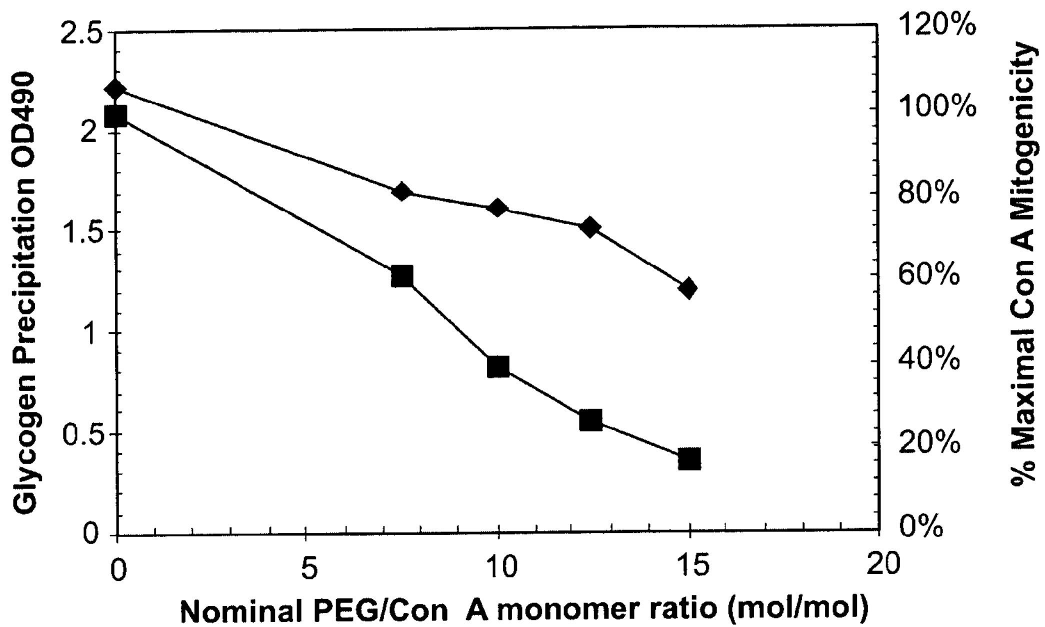
FIG. 13. Correlation between Glycogen Precipitation OD490 and % maximal Con A mitogenicity for HT-1 Series. (■) % maximal Con A mitogenicity, (♦) Glycogen Precipitation OD490.
Figure 14:
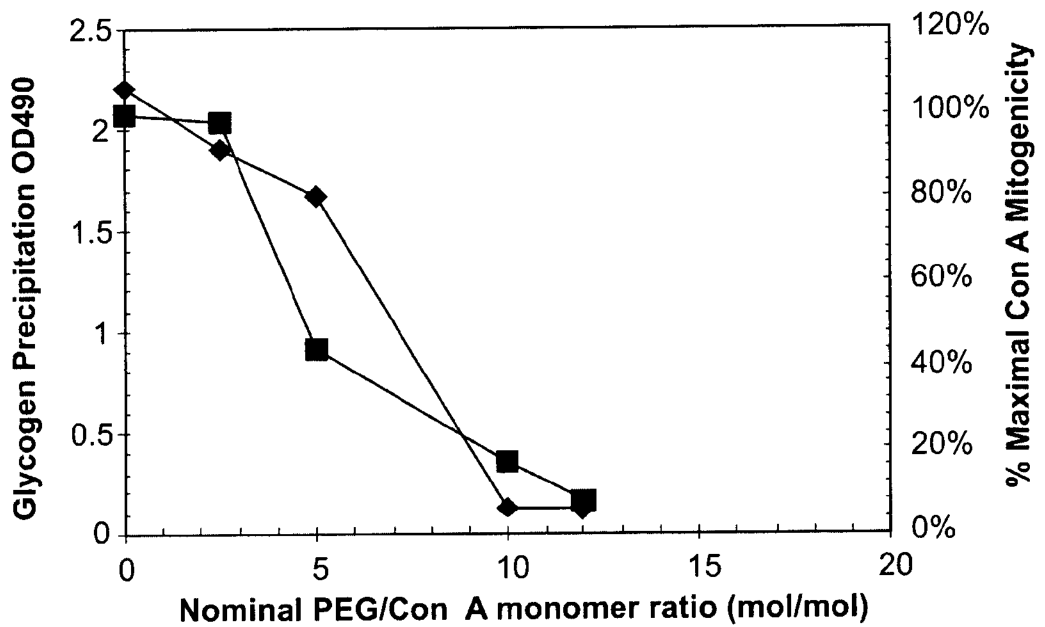
FIG. 14. Correlation between Glycogen Precipitation OD490 and % maximal Con A mitogenicity for HT-2 Series. (■) % maximal Con A mitogenicity, (♦) Glycogen Precipitation OD490.
Figure 15:
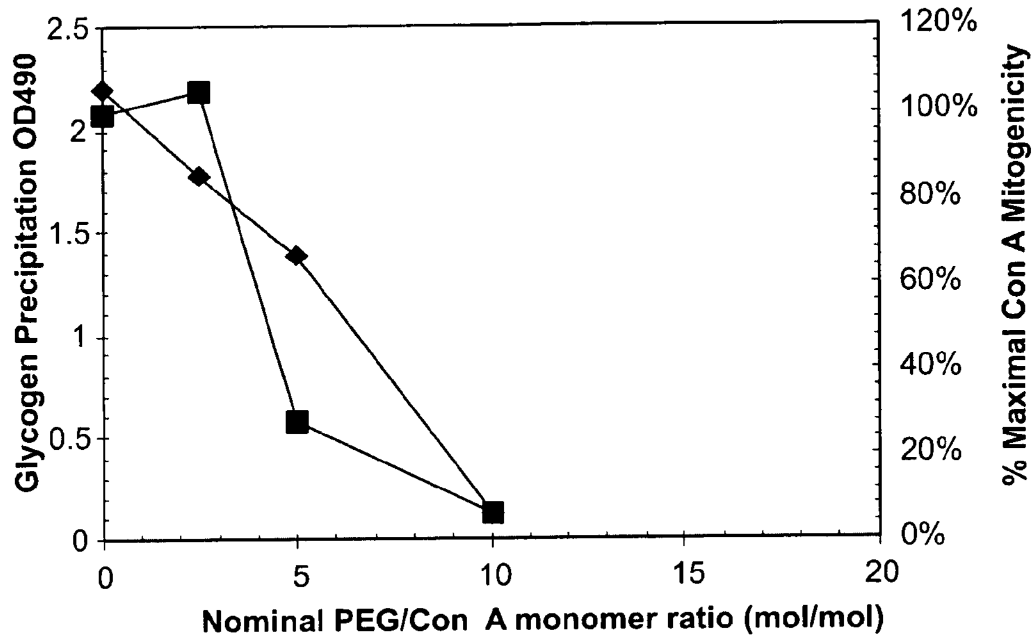
FIG. 15. Correlation between Glycogen Precipitation OD490 and % maximal Con A mitogenicity for HT-5 Series. (■) % maximal Con A mitogenicity, (♦) Glycogen Precipitation OD490.
Figure 16:
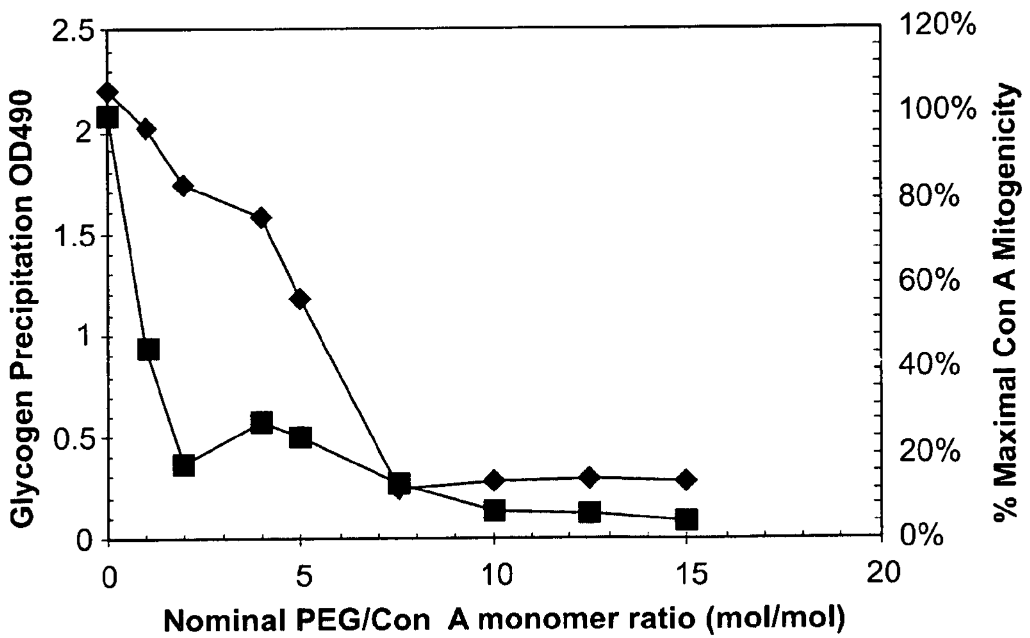
FIG. 16. Correlation between Glycogen Precipitation OD490 and % maximal Con A mitogenicity for HT-10 Series. (■) % maximal Con A mitogenicity, (♦) Glycogen Precipitation OD490.

This example compares the cell agglutination properties of a native Con A composition and modified Con A compositions P11-P16, P24-P29, P62, and P64. Each of the pegylated compositions was synthesized according to the generalized procedure of Example 8. Table 12 shows the type of PEG reagent, desired degree of pegylation, mass of PEG reagent, buffer type, etc. required for each the modified Con A compositions. The minimum agglutinating concentrations (MAC) of each composition was determined as described in Example 6. The mitogenicity of each material was evaluated at 1000, 100, 10, 1, 0.1, and 0.1 ug/ml as described in Example 1. FIG. 12 is a scatter plot of % Con A maximal mitogenicity versus MAC for all 15 compositions. The plot shows that irrespective of the method and type of Con A modification, those samples possessing a MAC greater than a threshold of about 6 ug/ml exhibit less than 5% of the maximal Con A mitogenicity even at the highest concentrations evaluated.

TABLE 12

Synthesis parameters for modified Con A compositions P11-P16, P24-P29, P62, and P64.

| Sample | PEG Reagent | Desired Degree of PEGylation (mol PEG/mol of monomer) | g PEG/g Con A | Buffer | Temperature | Protection with alpha-methyl-mannose | Starting Material |
|---|---|---|---|---|---|---|---|
| Con A | n/a | 0 | 0.0 | 0 | 0 | 0 | 0 |
| P11 | PEG-2K-SPA | 5 | 0.4 | pH 7 BES | RT | + | Con A |
| P12 | PEG-2K-SPA | 2.5 | 0.2 | pH 7 BES | RT | + | Con A |
| P13 | PEG-2K-SPA | 4 | 0.3 | pH 7 BES | RT | + | Con A |
| P14 | PEG-2K-SPA | 3 | 0.2 | pH 7 BES | RT | + | Con A |
| P15 | PEG-2K-SPA | 2 | 0.2 | pH 7 BES | RT | + | Con A |
| P16 | PEG-2K-SPA | 1 | 0.1 | pH 7 BES | RT | + | Con A |
| P24 | PEG2-10K-NHS | 26 | 10.0 | pH 8.5 Borate | RT | − | Con A |
| P25 | PEG2-10K-NHS | 26 | 10.0 | pH 8.5 Borate | RT | + | Con A |
| P26 | PEG-5K-SPA | 10 | 2.0 | pH 8.5 Borate | 4° C. | − | Con A |
| P27 | PEG-5K-SPA | 10 | 2.0 | pH 8.5 Borate | 4° C. | + | Con A |
| P28 | PEG-2K-SPA | 5 | 1.0 | pH 8.5 Borate | 4° C. | − | PEG-5-2K Con A (RT, BES) |
| P29 | PEG-2K-SPA | 5 | 1.0 | pH 8.5 Borate | 4° C. | + | PEG-5-2K Con A (4° C., Borate) |
| P62 | PEG-5K-SPA | 10 | 2.0 | pH 7 BES | RT | − | Con A |
| P64 | PEG-2K-SPA | 10 | 0.8 | pH 7 BES | RT | − | Con A |

Example 27

Correlation Between Glycogen Precipitation and Mitogenicity

This example compares the glycogen precipitation properties of a native Con A composition and modified Con A compositions HT-1-7.5, 10, 12.5, 15; HT-2-2.5, 5, 10, 12; HT-5-2.5, 5, 10; and HT-10-1, 2, 4, 5, 7.5, 10, 12.5, 15. Each of the pegylated compositions was synthesized according to the procedures described in Example 18. The mitogenicity of each material was evaluated at 100, 10, and 1 ug/ml as described in Example 1. In addition, the ability to precipitate glycogen (OD490) was assessed as described in Example 7. FIGS. 13 through 16 are plots of % Con A maximal mitogenicity and glycogen precipitation OD490 versus desired degree of pegylation for each of the HT-1, HT-2, HT-5, and HT-10 series, respectively. Each plot shows that for each type of PEG reagent, a reduction in % Con A maximal mitogenicity is strongly correlated with the ability of each modified Con A composition to precipitate glycogen.

(G) In Vivo Effects of Lectin Modification

Examples 28-33 describe various experiments that were performed to assess the impact of lectin modification on various cellular and immunogenic properties.

Example 28 demonstrates a reduction in binding of inventive modified lectins to human PBMCs.

Example 29 describes experiments showing that inventive modified lectin compositions exhibit a reduced cell cytotoxicity as compared to the native lectin.

Example 30 describes experiments that can be used to evaluate the effect of lectin modification on the induction of cell surface antigens.

Example 31 describes a method for producing cytokines from human PBMCs cultured with various concentrations of native and modified lectin compositions.

Example 32 describes a method for comparing the in vivo toxicity profiles of native and modified lectin compositions.

Example 33 compares the ability of a native and modified Con A compositions to elicit production of anti-Con A antibodies in vivo.

Example 28

Reduced Binding to Human PBMCs

This example compares the human PBMC cell-binding properties of fluorescently-labeled native Con A composition and fluorescently-labeled modified Con A composition FITC-PEG-10-5K with their resulting mitogenicity values. FITC-PEG-10-5K was synthesized according to the generalized procedure described in Example 8 using FITC-PEG-5K-NHS (Nektar Therapeutics, San Carlos, Calif.) at a PEG:Con A monomer molar ratio of 10, or a PEG:Con A mass ratio of 2. FITC-Con A was purchased from Sigma-Aldrich (St. Louis, Mo.). The mitogenicity of FITC-PEG-10-5K, FITC-PEG-5K-NHS (FITC-PEG), Con A, and FITC-Con A were evaluated at 100, 10, and 1 ug/ml as described in Example 1. In addition, the samples incubated at 10 ug/ml were run on a fluorescence assisted cell sorting (FACS) machine to obtain a histogram of fluorescence intensity versus cell count. FITC alone was added to a population of cells as a negative control to provide a background of non-specific cell staining. In addition, PBMCs incubated with a FITC-CD2 antibody, known to bind specifically to the surface of specific PBMCs, were run as a positive control.

Figure 17:
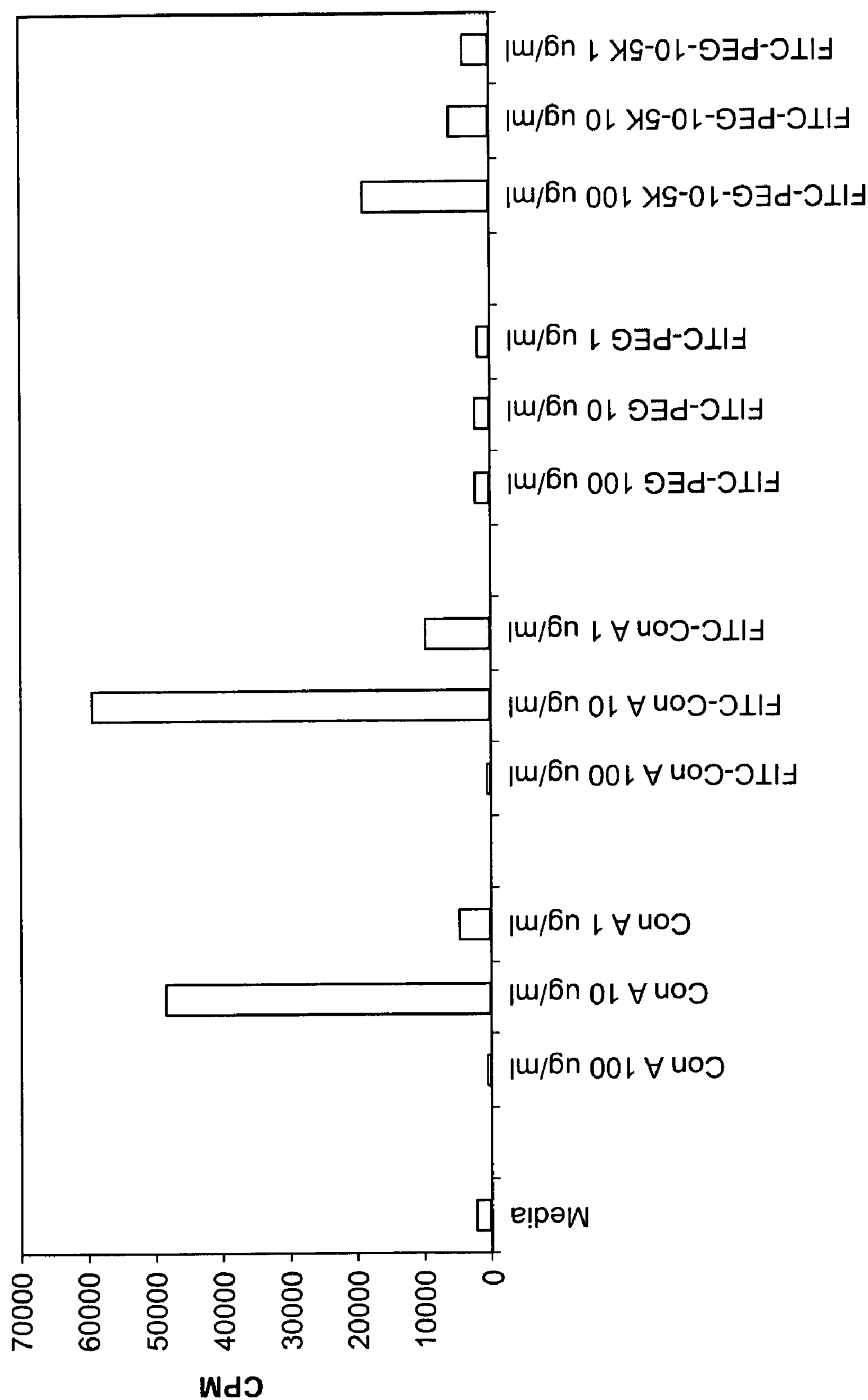
FIG. 17. Mitogenicity data for Con A, FITC-Con A, FITC-PEG, and FITC-PEG-10-5K Con A.

FIG. 17 shows the mitogenicity data obtained for each sample plotted as the CPM for each concentration of the different samples. As expected, the pegylated FITC-PEG-10-5K Con A exhibits reduced mitogenicity as compared to the unmodified FITC-Con A and Con A samples.

Figure 18:
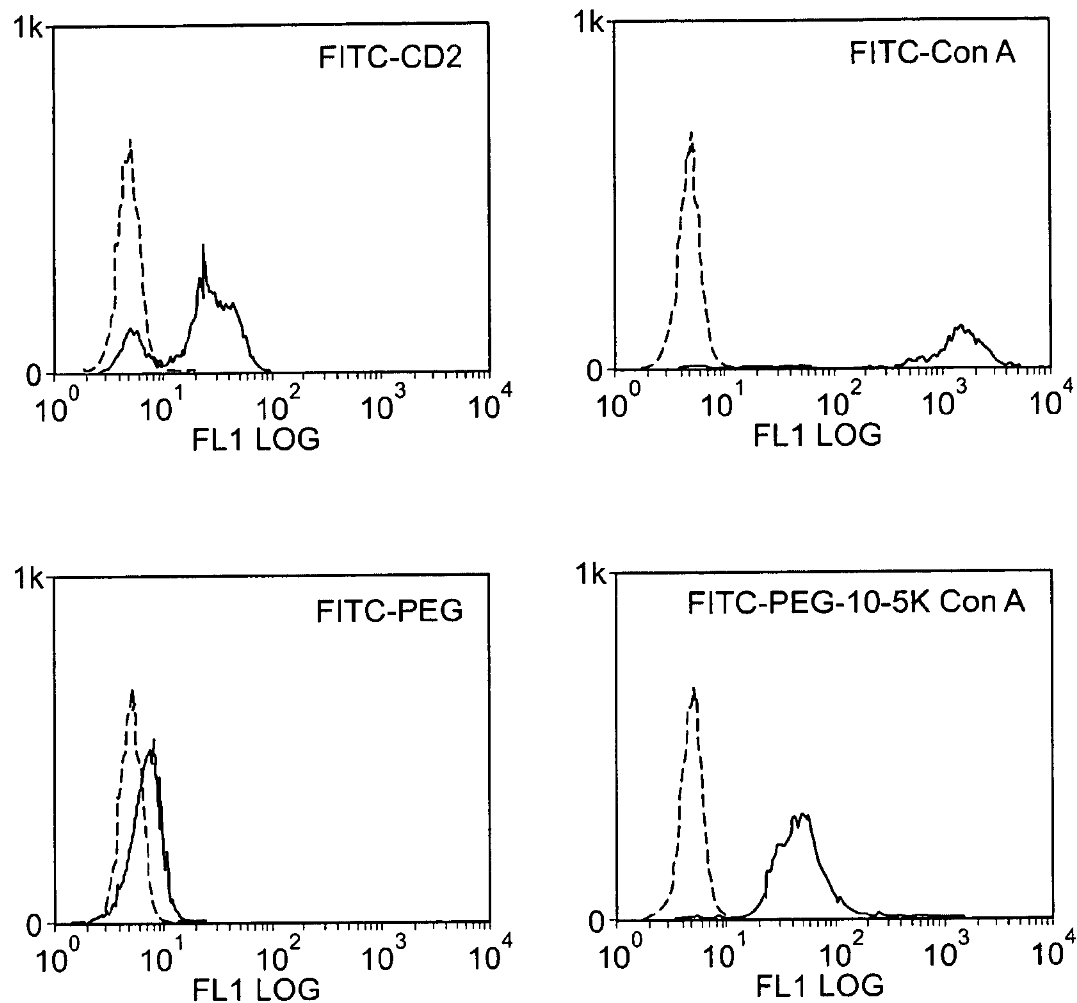
FIG. 18. FACS data for FITC-CD2, FITC-Con A, FITC-PEG, and FITC-PEG-10-5K Con A.

FIG. 18 shows the four histograms obtained from the FACS experiments. Each dotted line represents the staining of cells from FITC alone. As expected, the peak for FITC-PEG and FITC alone overlap, indicating no specific cell binding of FITC-PEG alone. In addition, the histogram for cells incubated with FITC-CD2 show a significant number of cells with specific staining. The histogram for FITC-Con A demonstrates binding of Con A to an even larger number of cells than the CD2. The histogram for FITC-PEG-10-5K Con A, however, demonstrates a significantly reduced amount of binding to the same population of cells. Without being bound to any particular theory, it appears that the reduced mitogenicity of modified Con A may be due at least in part by a reduced capacity to bind the target cells.

Example 29

Cell Viability and Mitogenicity

This example evaluates the mitogenicity and cell viability of PBMCs cultured with various concentrations of native Con A and modified Con A compositions P28-P31 and P33-P34. Each of the pegylated compositions was synthesized according to the general procedures described in Example 8. Table 13 shows the type of PEG reagent, desired degree of pegylation, mass of PEG reagent, buffer type, etc. used for each of the modified Con A compositions.

TABLE 13

Synthesis parameters for modified Con A compositions P28-P31 and P33-P34.

| Sample | PEG Reagent | Desired Degree of PEGylation (mol PEG/mol of monomer) | g PEG/g Con A | Buffer | Temperature | Protection with alpha-methyl mannose | Starting Material |
|---|---|---|---|---|---|---|---|
| Con A | n/a | 0 | 0.0 | 0 | 0 | 0 | 0 |
| P28 | PEG-2K-SPA | 5 | 1.0 | pH 8.5 Borate | 4° C. | – | PEG-5-2K Con A (RT, BES) |
| P29 | PEG-2K-SPA | 5 | 1.0 | pH 8.5 Borate | 4° C. | + | PEG-5-2K Con A (4° C., Borate) |
| P30 | PEG-5K-SPA | 10 | 2.0 | pH 7 BES | RT | – | Con A |
| P31 | PEG-2K-SPA | 10 | 0.8 | pH 7 BES | RT | – | Con A |
| P33 | PEG2-10K-NHS | 5 | 2.0 | pH 8.5 Borate | 4° C. | + | Con A |
| P34 | PEG-5K-SPA | 10 | 2.0 | pH 8.5 Borate | 4° C. | + | Con A |

The mitogenicity of each material was evaluated at 10 and 100 ug/ml as described in Example 1. Cell viability was determined using the procedure described in Example 2. Table 14 is a chart of the % maximal native mitogenicity at 10 ug/ml for each composition and the fraction cell viability at 10 ug/ml for each composition.

TABLE 14

Cell viability and mitogenicity of native Con A and modified Con A compositions P28-P31 and P33-P34.

| Sample at 10 ug/ml | Viability | % maximal Con A mitogenicity at 10 ug/ml |
|---|---|---|
| Con A | 0.84 | 100 |
| P28 | 0.99 | 8 |
| P29 | 0.99 | 3 |
| P30 | 0.99 | 7 |
| P31 | 0.98 | 5 |
| P33 | 0.99 | 12 |
| P34 | 0.96 | 4 |

The table shows that the measured reduction in mitogenicity for each of the modified Con A compositions is not an artifact of the compositions being potentially cytotoxic and therefore masking any potential proliferation. However, the data (not shown) also demonstrated that when native Con A is incubated with PBMCs at 100 ug/ml, less than 5% of the cells are still viable. Thus the reduced mitogenicity that is observed with native Con A at 100 ug/ml is an artifact that simply reflects its ability to induce cell-mediated cytotoxicity. Notably, each of the modified Con As demonstrates at least 95% cell viability at the same high concentration with still significant reductions in mitogenicity.

Example 30

Activation of Cell Surface Antigens

This example provides a method for evaluating the activation of antigens on the surface of human T-cells cultured with various concentrations of native lectin and modified lectin compositions. For example, compositions may be synthesized according to the general procedures described in Example 8. The induced activation of T-cell antigens for each composition is then evaluated at 100, 10, and 1 ug/ml. Briefly, PBMCs are cultured for 1, 3 or 7 days in RPMI1640 medium with 10% FCS, with or without native lectin, modified lectin, or medium alone. Cells are washed, labeled with specific mouse monoclonal antibodies, an anti-mouse fluoresceinated secondary antibody, and then analyzed by fluorescence assisted cell sorting (FACS). Specific surface structures analyzed include CD2, CD3, CD4, CD8, CD25 (the high affinity IL-2 receptor), CD98, and Class II MHC. A variety of other cell surface structures can be analyzed if required. The results from this assay will likely show that inventive modified lectin compositions with reduced mitogenicity have a significantly reduced ability to activate antigens on the surface of human T-cells as compared to the native lectins.

Example 31

Production of Cytokines

This example describes a method for producing cytokines from human PBMCs cultured with various concentrations of native and modified lectin compositions. For example, pegylated Con A compositions synthesized according to the general procedures described in Example 8 may be assayed. The production of cytokines for each material is evaluated at 100, 10, and 1 ug/ml. Briefly, PBMCs are cultured for 7 days with native or modified lectin and then washed, placed in fresh medium, and cultured with stimuli (the same lectin, PMA/ionomycin, or anti-CD3). Cytokine production is measured by ELISA for IL-2, IL-4, IL-10 and gamma-interferon after 48-72 hours of the second culture, using cell-free culture supernatant. In addition, cytokine production is also measured after overnight culture of 7 day activated cells by intracellular FACS. For this assay Brefeldin A is included in the second culture medium, and cells are permeabilized before staining for FACS. These assays indicate whether specific cytokines cause Th1 or Th2 skewing. The results from these assays will likely show that the modified lectin compositions with reduced mitogenicity will have significantly reduced ability to induce T-cell cytokine production as compared to unmodified native lectin.

Example 32

In Vivo Toxicity of Modified Lectin Compositions

This example describes a method for comparing the in vivo toxicity profiles of native Con A composition and modified Con A compositions P24 and P41.

P24 is prepared according to the generalized procedure of Example 8 using PEG2-10K-NHS (Nektar Therapeutics, San Carlos, Calif.) at a PEG:Con A monomer molar ratio of 26, or a PEG/Con A mass ratio of 10 with the following changes: the reaction was carried out in borate buffer at 37 C.

P41 is prepared according to the generalized procedure of Example 8 using FITC-PEG-5K-NHS (Nektar Therapeutics, San Carlos, Calif.) at a PEG:Con A monomer molar ratio of 10, or a PEG:Con A mass ratio of 2 with the following changes: the reaction was carried out in borate buffer at room temperature.

Sterile solutions of Con A, P24, and P41 in a pH 7.4 Tris-HCl buffer containing 0.150 M NaCl are then injected subcutaneously at a dose of 3 mg of Con A equivalents/kg into six male Sprague-Dawley rats (Charles River Laboratories, Wilmington, Mass.) every day for a total of 28 days. In addition, a sterile pH 7.4 Tris-HCl buffer containing 0.150 M NaCl is injected daily into six rats as a negative control. On days 0, 7, 14, and 28, 0.5 ml of blood is collected via tail vein bleeding and centrifuged, after which the serum is collected and frozen until assayed for toxicology markers. Less than 0.1 ml of serum is added to a Vetscan Comprehensive Diagnostic rotor and inserted into a Vetscan blood chemistry analyzer (Abaxis) for analysis of ALB, ALP, ALT, AMY, BUN, CA, CRE, GLOB, GLU, K, NA, PHOS, TBIL, TP. It is expected that P24 and P41 will cause minimal changes in marker concentration, while native Con A will exert in vivo toxic effects that are measurable on the blood chemistry analyzer.

Example 33

Reduced Antigenicity of Modified Con A

This example compares the ability of a native Con A composition and modified Con A compositions P24 and P41 to elicit production of anti-Con A antibodies in vivo. P24 and P41 were prepared as described in Example 32.

Sterile solutions of Con A, P24, and P41 in a pH 7.4 Tris-HCl buffer containing 0.150 M NaCl were injected subcutaneously at a dose of 3 mg of Con A equivalents/kg into three male Sprague-Dawley rats (Charles River Laboratories, Wilmington, Mass.) each week. In addition, sterile pH 7.4 Tris-HCl buffer containing 0.150 M NaCl was injected each week into three rats as a negative control. On weeks 0 through 8 of the experiment, 0.5 ml of blood was collected via tail vein bleeding and centrifuged, after which the serum was collected and frozen until assayed for antibodies.

Anti-Con A IgG-class antibodies were assayed using a custom-made enzyme-linked immunosorbent assay (ELISA). To each well of a 96-well microplate coated with Con A (Proteocell, Quebec, Calif.), 0.1 ml of serum, diluted by 1:1000 in 1× antibody conjugate solution, was added and incubated at room temperature for 30 minutes, after which each well of the plate was washed with 3×0.200 ml of wash buffer. 0.1 ml of 1× HRP-conjugated anti-rat IgG antibody, diluted 1:10,000 from a commercially available anti-rat IgG kit (Alpha Diagnostic International, San Antonio, Tex.) was then added and the wells were incubated at room temperature for 30 minutes, after which the wells were emptied and washed four times with the kit wash buffer. After extensive washing, 0.1 ml of TMB substrate was added from the kit, and the wells were incubated for 10 minutes, after which 0.1 ml of 1× stop solution was added from the kit. The absorbance of each well of the plate was read at a wavelength of 450 nm using a 96-well UV VIS plate reader (SpectraMax, Molecular Devices, Sunnyvale, Calif.). The absorbance value (OD450) obtained for each serum sample was then used as a determinant for the concentration of anti-Con A IgG antibodies present in the sample.

Figure 19:
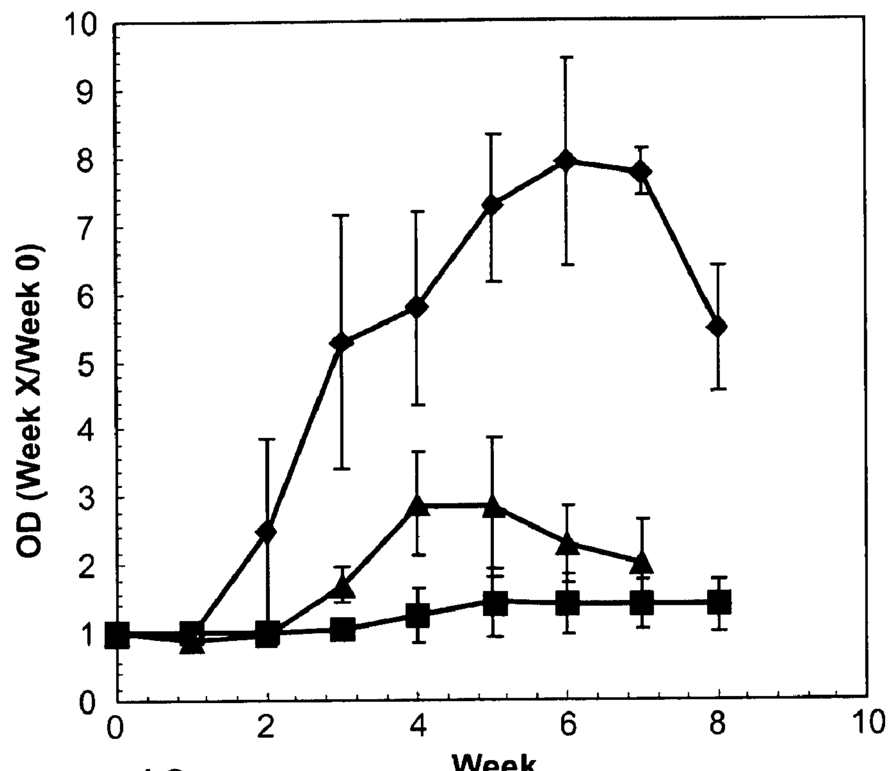
FIG. 19. Production of anti-Con A IgG antibodies (OD) in rats immunized with (♦) Con A, (▲) P41, and (■) P24.

FIG. 19 is a plot of the OD450 obtained each week divided by the OD450 obtained on Week 0 for native Con A immunizations along with those obtained for the P24 and P41 immunizations. Based on the diminished capacity to elicit the production of a measurable concentration of anti-Con A antibodies, these results demonstrate that P24 is completely non-antigenic, while P41 is only slightly antigenic when compared to native Con A.

In addition, the mitogenicity of native Con A, P24, and P41 were evaluated at 1000, 100, 10, 1, 0.1, and 0.01 ug/ml as described in Example 1. P24 exhibited less than 6% of the maximal native mitogenicity at all evaluated concentrations while P41 exhibited less than 5% of the maximal Con A mitogenicity at all evaluated concentrations. Taken together, these results indicate that modified Con A compositions P24 and P24 are both non-mitogenic and non-antigenic.

(H) Exemplary Uses of Inventive Lectin Compositions

Examples 34-39 describe certain uses of the inventive lectin compositions. As discussed earlier, the inventive lectin compositions exhibit reduced mitogenicity and are therefore useful for a number of in vivo applications.

Examples 34-35 describe the preparation of fluorescently labeled polysaccharides and their subsequent use with inventive lectin compositions in FRET applications.

Example 36 describes the use of inventive lectin compositions in viscometric glucose sensors.

Example 37 describes the use of inventive lectin compositions in a glucose-responsive drug delivery system that makes use of an insulin-saccharide drug conjugate (e.g., the system of U.S. Pat. No. 4,348,387).

Example 38 describes the use of inventive lectin compositions in a glucose-responsive drug delivery system that makes us of free insulin that has been entrapped within a reversible gel.

Example 39 describes the use of inventive lectin compositions in a glucose-responsive drug delivery system that makes use of an insulin-polysaccharide drug conjugate (e.g., the system of U.S. Patent Publication No. 2004/0202719).

Example 34

Preparation of Fluorescently-Labeled Polysaccharides

This example describes a method for making fluorescent polysaccharides, specifically tetramethylrhodamine isothiocyanate (TRITC, Sigma Aldrich, St. Louis, Mo.) derived mannan which is sometimes used in FRET-based glucose sensors. The TRITC-mannan compound is used in the application of Example 35.

Briefly, in a Schlenk tube under nitrogen, 1 g of mannan (Sigma Aldrich, St. Louis, Mo.) was dissolved in 20 ml of dimethylsulfoxide (DMSO, Sigma Aldrich, St. Louis, Mo.) at 95 C. until the solution was clear. Next two drops of pyridine (anhydrous, Sigma Aldrich, St. Louis, Mo.) were added to the mixture. 20 mg of TRITC powder was added directly to the heated solution, and then 10 ul of a dibutyltin dilaurate (Sigma Aldrich, St. Louis, Mo.) was added and the mixture allowed to react for 2 hours, after which time the flask was removed from the temperature bath and allowed to cool. The TRITC-mannan was purified by several precipitation cycles using 50:50 ethanol:diethyl ether mixtures, where the precipitate was centrifuged at 2000×g for 10 min (Allegra 21R, Beckman Coulter, Fullerton, Calif.) and redissolved in the minimum amount of deionized water to redissolve the centrifuged particle cake between each precipitation step. This was repeated until no visible red or orange color was visibly seen in the supernatant after centrifuging the solution under the above conditions. The precipitate was redissolved in deionized water a final time and lyophilized to give the purified TRITC-mannan product.

Example 35

Use of Modified Lectin Compositions in FRET Applications

This method describes an application of the inventive modified Con A compositions as a glucose sensor based on fluorescence resonance energy transfer (FRET). FRET is based on the fact that when two different fluorophores are brought closely together this allow for energy transfer between the two fluorophores, resulting in a decrease in the fluorescence of one or both of the fluorophores, which is called fluorescence quenching (Ballerstadt et al., *Anal. Chim. Acta* 345:203-212, 1997).

In the absence of a monosaccharide inhibitor, a mixture of a fluorescent modified Con A and a fluorescent polysaccharide will form a compact gel and the neighboring fluorophores will undergo FRET. In the presence of a monosaccharide inhibitor such as glucose, the average distance between the fluorescent modified Con A and the fluorescent polysaccharide will increase causing the level of FRET to decrease and thereby leading to an increase in the individual fluorescence signals.

Some of the highly pegylated Con A compositions that were made by the methods of Example 8 were found to bind higher affinity mannan-agarose beads in Example 24 and yet retain their monosaccharide binding affinities as measured by the method of Example 4. These compositions were also found to be free of cytotoxicity as measured by the methods of Example 2 and were found to be nearly non-mitogenic or completely non-mitogenic as measured by the methods of Example 1. Because of their ability to bind higher affinity polysaccharides and monosaccharides such as glucose, these pegylated Con A compositions would be ideally suited for this application. In addition, because of their improved safety profile these pegylated Con A compositions may provide for a safe and efficacious in vivo glucose sensor.

The following in vitro tests were therefore performed using the modified Con A composition P62 of Example 8. The synthesis and purification of FITC-PEG-10-5k-Con A (FP62) was the same as for P62 except that fluorescein isothiocyanate (FITC, Sigma Aldrich, St. Louis, Mo.) PEG-5k (Nektar Therapeutics, San Carlos, Calif.) was substituted for PEG-5k. The purified FITC-modified Con A was then mixed with TRITC-mannan synthesized according to Example 34.

Three stock solutions were made as follows:

(i) FP62 Stock—60 mg of FITC was dissolved in 2 ml of 100 mM BES, pH 7, 1.0 M NaCl, 1 mM $MnCl_2$ and 1 mM $CaCl_2$.

(ii) TRITC-mannan Stock—60 mg of TRITC-mannan was dissolved in 2 ml of 100 mM BES, pH 7, 1.0 M NaCl, 1 mM $MnCl_2$ and 1 mM $CaCl_2$.

(iii) Glucose Stock—a 1200 mg/dl glucose solution was made by dissolving 1200 mg glucose in 100 ml of 100 mM BES, pH 7, 1.0 M NaCl, 1 mM $MnCl_2$ and 1 mM $CaCl_2$.

1:2 serial dilutions of the FP62 and TRITC-mannan stock solutions were then performed in 100 mM BES, pH 7, 1.0 M NaCl, 1 mM $MnCl_2$ and 1 mM $CaCl_2$ separately so that the final concentrations of FP62 and TRITC-Mannan were 30, 3, 0.3, 0.03, 0.003, 0.0003, 0.00003, and 0.000003 mg/ml. FIG. 20 describes how the stock solutions were mixed together on a 96-well microtiter plate (VWR Scientific, Bridgeport, N.J.). The plate was designed so that the final concentrations of all components are decreased by a factor of 3× after mixing all solutions together.

After mixing the solutions together, the fluorescence of the plate was assayed by a fluorescence plate reader (ƒmax, Molecular Devices, Sunnyvale, Calif.) using the 485/525 nm filter pair for FITC and 544/590 nm filter pair for measuring TRITC fluorescence.

After measuring with both sets of filter pairs using the 1200 mg/dl glucose buffer at room temperature, the plate was heated to 37 C. using the plate reader incubator function. After 30 minutes of equilibration, the plate was read for both FITC and TRITC fluorescence a second time. After which the plate was allowed to recool to room temperature.

Figure 21:
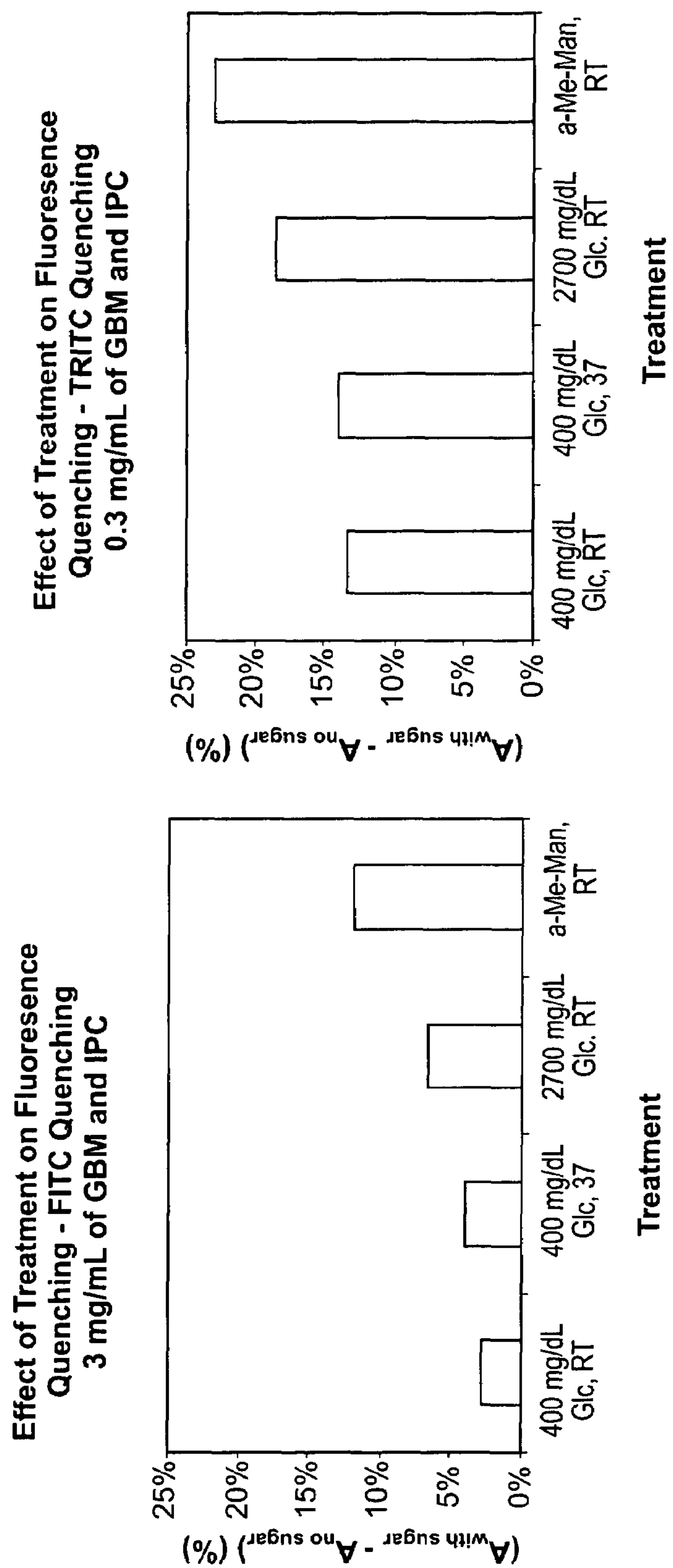
FIG. 21. (left) Effect of monosaccharide treatment on inhibition of FITC-FRET for FP62-TRITC-Mannan ratio of 1 at a concentration of 3 mg/ml. (right) Effect of monosaccharide treatment on inhibition of TRITC-FRET for FP62-TRITC-Mannan ratio of 1 at a concentration of 0.3 mg/ml.

Rows 2, 4, 6, and 8 all received another 50 ul of a 9600 mg/dl glucose solution, while Rows 1, 3, 5, and 7 all received another 50 ul of buffer. The plate was read a third time at room temperature, and the process was repeated a final time using 0.1 M Methyl-α-mannopyrannoside. The FITC and TRITC fluorescence data are shown in FIG. 21 for the two ratios that showed the largest change in signal relative to the controls.

Inhibition of FITC-quenching by the saccharides was observed in both the FITC and TRITC measurements. However, overall the TRITC-mannan showed the largest change in fluorescence in the presence of glucose at FP62 and TRITC-mannan concentrations of 0.3 mg/ml. This example demonstrates that physiologically relevant glucose levels (400 mg/dl) were able to cause a 13% increase in fluorescence compared to the FP62/TRITC-mannan mixture without glucose. Further FRET quenching occurred at higher temperatures and monosaccharide concentrations, and further optimization of the glucose sensor could be made by adjusting the affinity of the polymer, optimizing the fluorescence loading of the modified Con A and TRITC-mannan, and rerunning the experiment on a fluorescence spectrophotometer to allow for the maximum FRET or FRET quenching compared to the plate reader/filter pair setup.

Example 36

Viscosimetric Glucose Sensor

This example demonstrates how modified Con A composition P64 was used in a system that is capable of detecting glucose based on the changes in viscosity of a glucose-responsive solution. P64 was synthesized according to the generalized procedure of Example 8 using PEG-SPA-2K at a PEG:Con A monomer molar ratio of 10, or a PEG:Con A mass ratio of 1. P64 was then dissolved in a 20 mM BES buffer at pH 7 containing 1 mM $MnCl_2$ and $CaCl_2$ at a concentration of 100 mg Con A equivalents/ml. Separately, yeast mannan (Sigma-Aldrich, St. Louis, Mo.) was dissolved in five solutions of 200 mM BES buffer at pH 7 at a concentration of 50 mg/ml with each solution containing 0, 100, 800, 1600, and 3200 mg/dl of glucose, respectively. 0.700 ml of the P64 stock solution was mixed with each of the five mannan stock solutions containing the varying concentrations of glucose such that the five resulting solutions contained 0, 50, 400, 800, and 1600 mg/dl of glucose.

Figure 22:
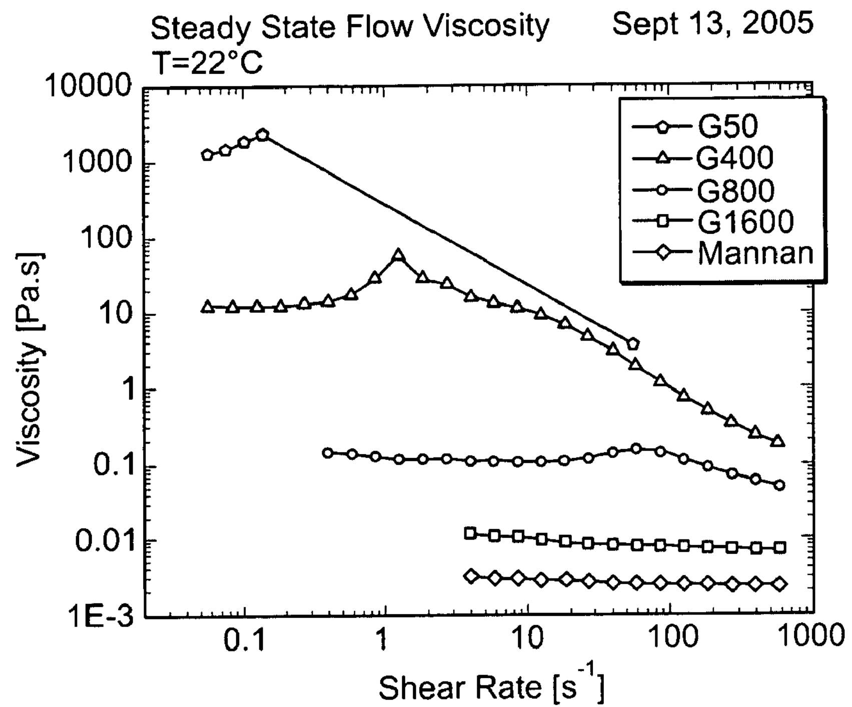
FIG. 22. Viscosity profiles of P64-mannan viscous liquids as a function of glucose concentration at 22° C.
Figure 23:
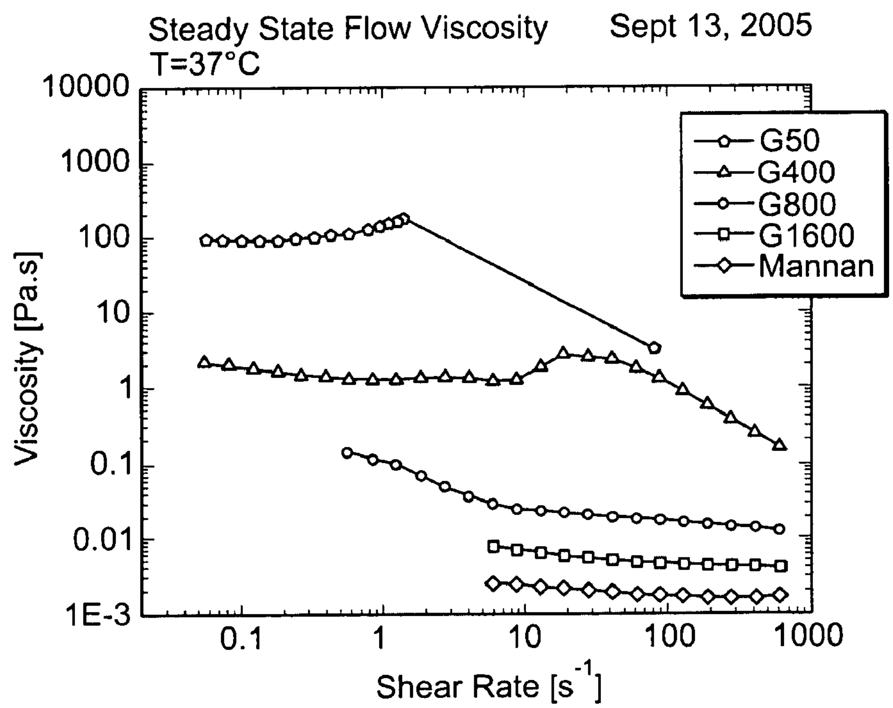
FIG. 23. Viscosity profiles of P64-mannan viscous liquids as a function of glucose concentration at 37° C.

The viscosity of each solution was measured as a function of shear rate using a microviscometer set up in a cone-and-plate geometry. The cone measures 4 cm in diameter and has a 2 degree angle, requiring a sample volume of 0.58 ml. A solvent trap was used to reduce sample evaporation. Steady state flow viscosity was measured for a range of shear rates for each sample at both 22 C. and 37 C. FIGS. 22 and 23 show that the viscosity of the gel solutions decrease by almost five orders of magnitude as the glucose concentration increases from 50 mg/dl (G50) to 1600 mg/dl (G1600).

Therefore, when this liquid is contacted by a body fluid, the measured viscosity will directly correlate to the fluid's glucose concentration. Unlike previous systems that use toxic, mitogenic, native Con A (e.g., see U.S. Pat. Nos. 6,210,306; 6,267,002; 6,477,891; and 6,938,463), the inventive modified Con A compositions with significantly lower mitogenicity and minimal toxicity will not induce adverse side effects when in contact with the body fluid.

Example 37

Glucose-Responsive Insulin Delivery System that Uses an Insulin-Monosaccharide Conjugate This example demonstrates how inventive modified Con A compositions can be used in a glucose-responsive drug delivery system such as the one described in U.S. Pat. No. 4,348,387 that makes use of native Con A and an insulin-maltose drug conjugate. For example, the native Con A of the '387 patent could be advantageously replaced with inventive modified Con A composition P64. The mechanism of glucose-responsive release would remain essentially the same as described in U.S. Pat. No. 4,348,387. Thus, release of the soluble insulin-maltose from immobilized lectin (in this case inventive modified lectin) would be controlled primarily by competitive binding between free glucose and the insulin-maltose conjugate.

Preparation of a Maltose-Insulin Conjugate

Maltose is incubated with porcine insulin at a molar ratio of 650:1 for 5 days at 37 C. in 0.1 M sodium phosphate buffer pH 8. The incubation is carried out in the presence and absence of 0.25 M sodium cyanoborohydride. Unreacted maltose is removed by gel filtration and the conjugated insulin is separated by affinity chromatography, e.g., on a Con A column. The insulin conjugate can be stored at 4 C. and is stable for at least seven weeks regardless of whether or not reducing agent had been added.

Binding of Maltose-Insulin to Modified Con A

The elution profile can be obtained for 20 mg of unmodified insulin and maltose-insulin applied to columns (24.0×1.5 cm I.D.) of immobilized modified Con A composition P62. The initial buffer can be 1 mM $MgCl_2$, 1 mM $CaCl_2$, 50 mM NaCl, 25 mM sodium phosphate, pH 7.4. At a particular point in time, 0.2 M glucose in the column buffer can begin. Fractions (e.g., 2.0 ml) can be collected at a flow rate of 10-15 ml/hour. Unmodified insulin should not bind to modified Con A. When this material is applied to the modified lectin, all of the protein should be recovered in the buffer wash, and none will be eluted by the addition of glucose. In contrast, all of the maltose-insulin derivative should be bound to the modified Con A, since P62 is known to bind mono and trisaccharides just as well if not better than native Con A. None of the maltose-insulin should be eluted by the buffer wash, and all of the maltose-insulin derivative should be displaced from modified Con A binding sites by a 1,000:1 molar excess of glucose.

Another elution profile can be obtained from 20 mg maltose-insulin derivative applied to a column (12.0×1.5 cm I.D.) of immobilized modified Con A composition P62. Initial buffer can be 1 mM $MgCl_2$, 1 mM $CaCl_2$, 50 mM NaCl, 25 mM sodium phosphate, pH 7.4. Displacement of maltose-insulin can then be accomplished using 1.0 ml pulses of column buffer containing varying amounts of glucose. Fractions (e.g., 1.7 ml) can be collected at a flow rate of 10-15 ml/hour. Glucose-pulse experiments with the modified lectin-bound maltose-insulin derivative will demonstrate that hormone release is a function of the quantity of glucose present.

Example 38

Glucose-Responsive Insulin Delivery System that Uses Free Insulin

This example demonstrates how inventive modified lectin compositions can also be used in another glucose-responsive drug delivery system. The drug delivery system is based on a modified lectin molecules that still contain multiple binding sites for sugars, with a particular affinity for glucose and mannose residues. The binding of glucose to the binding site is, however, reversible.

The inactive form of the drug system comprises glucose or mannose present as terminal moieties of a carbohydrate. The carbohydrate is a branched chain polysaccharide with many terminal glucose or mannose moieties which can bind to the binding sites modified lectin molecules and in so doing cross-link the modified lectin molecules together to form a viscous gel matrix. Insulin is premixed with the gel, so that when the modified lectin is added to the mixture, a gel is formed between the carbohydrate and the modified lectin with the insulin relatively immobilized inside the gel matrix and thus unable to escape rapidly.

The binding of carbohydrate to modified lectin is reversed when there is an increase in the concentration of free glucose in the physiological environment. The free glucose displaces the terminal glucose or mannose from the binding sites of the modified Con A molecules. The matrix undergoes a conformational change allowing mobilization and release of the insulin into the environment.

Once the level of free glucose falls (e.g., in response to the action of the released insulin), the displaced terminal glucose or mannose molecules will re-bind to the modified Con A molecules and the matrix will re-gel, thus again restricting insulin to remain within the matrix The mechanism of this drug system is thus repeatable and releases insulin in response to a number of free glucose insults, in a similar manner to the in vivo feedback mechanism of the pancreatic cells.

Examples of carbohydrates with naturally occurring glucose residues include dextran and glycogen. Synthetic carbohydrates that contain terminal mannose residues include dextran and glycogen covalently modified with mannose via divinylsulfone or cyanogen bromide coupling. Examples of carbohydrates with naturally occurring mannose residues include mannan. In this particular example, mannan derived from yeast (Sigma-Aldrich, St. Louis, Mo.) is used. The drug delivery system would be formulated in exactly the same manner described in Example 36 for preparing a glucose-responsive viscous solution, except that human recombinant insulin (Sigma-Aldrich, St. Louis, Mo.) is dissolved along with the mannan solution at a concentration of 5 mg/ml.

Experiments carried out in vitro will show release of the insulin from the drug system in response to a glucose load. The release is carried out in 200 mM BES pH 7 buffer containing sodium chloride and trace quantities of manganese and calcium, important for saccharide moiety binding to lectin at both 22 C. and 37 C. The change in release rate will scale with the observed change in viscosity according to the following equation (Wilke et al., *AlChE J.,* 1:264, 1955):

$$D_v=7.4\times10^{-8}(\psi_B M_B)^{1/2}T/\mu V_A^{0.6}$$

Where $D_v$=diffusivity, $cm^2/s$

T=absolute temperature, K $\mu$=viscosity of solution, cP $V_A$=molar volume of solute as liquid at its normal boiling point, $cm^3$/g mol $\psi_B$=association parameter for solvent $M_B$=molecular weight of solvent With all parameters remaining essentially constant throughout the change in glucose concentration, the release rate will scale inversely with the viscosity. Based on the relative changes in viscosity measured in Example 36 for inventive Con A composition P64, Table 15 shows how the relative insulin release rate would be expected to increase with increasing glucose concentration.

TABLE 15

Calculated relative increase in insulin release rate based on measured glucose responsive viscosity changes in P64-mannan mixtures.

| Glucose | 22 deg. C. | | 37 deg. C. | |
|---|---|---|---|---|
| Concentration (mg/dl) | Viscosity (Pa-s) | Relative Insulin Release Rate | Viscosity (Pa-s) | Relative Insulin Release Rate |
| 50 | 1100 | 1.0E+00 | 100 | 1.0E+00 |
| 400 | 10.2 | 1.1E+02 | 1.5 | 6.7E+01 |
| 800 | 0.1 | 1.1E+04 | 0.11 | 9.1E+02 |
| 1600 | 0.01 | 1.1E+05 | 0.008 | 1.3E+04 |
| Mannan control | 0.0035 | 3.1E+05 | 0.0027 | 3.7E+04 |

The system could be implanted inside a diabetic patient with up to several months supply of insulin. Since inventive modified Con A composition P64 is not toxic, it is not necessary to enclose the matrix in a non-erodible material which allows the diffusion of free glucose and insulin into and out of the matrix, but does not allow the escape of the modified Con A molecules.

However, if such a material is desired, a suitable example is an acrylic permanent gel, covalently cross-linked in situ to form a three dimensional grid structure. Use of this material allows an implant to be recoverable and possibly "recharged" with insulin and reused. The acrylic network will also help to prevent overload of the receptor by a high level of irrelevant sugar with subsequent loss of specificity as well as preventing dose-dumping. In such a matrix, restriction of drug diffusion may occur by either an increase in viscosity or precipitation via the polysaccharide-modified lectin reaction.

Alternatively, the polysaccharide perimeter may be cross-linked with a specific agent, for example, epichlorohydrin to form a membrane of cross-linked polysaccharide around the gel.

It is worth noting that the inventive method is not limited to control by endogenous glucose levels. For example, when administering anything other than insulin or a drug which is intended to control blood sugar, the drug or agent may be released not by a feed-back mechanism but by a controlled administration of sugar, bringing literally to life the notion of a spoonful of sugar making the medicine go down.

Example 39

Glucose-Responsive Insulin Delivery System that Uses an Insulin-Polysaccharide Conjugate This example demonstrates how inventive modified lectin compositions can be used in another type of glucose-responsive drug delivery system such as the one described in U.S. Patent Publication No. 2004/0202719 that makes use of native Con A and an insulin-dextran drug conjugate. In this example, the lectin is advantageously replaced with modified Con A composition P64 and the insulin-polysaccharide conjugate is replaced with an insulin-mannosylated-glycogen conjugate. However, the mechanism of glucose-responsive release remains essentially the same, i.e., a gel formed between the two components is eroded with glucose such that it releases the insulin-polysaccharide conjugate from the surface in a glucose-responsive manner. The release is controlled primarily by competitive binding and not by diffusion as described in Example 38.

Mannosylated glycogen is synthesized according to the following method. Briefly, 1 g of Oyster Glycogen, Type II (Sigma Aldrich, St. Louis, Mo.) was dissolved in 56.67 ml of deionized water, after which time an equal volume of 56.67 ml of a pH 11.4, 1.0 M sodium carbonate buffer was added to the glycogen solution. The mixture was stirred for 15 min. Next, 0.86 ml of divinyl sulfone (Sigma Aldrich, St. Louis, Mo.) is added to the solution, and allowed to react for 1 hour. D-mannopyranose (mannose) (Sigma Aldrich, St. Louis, Mo.) was then added to achieve the desired mannose loading on the glycogen. In this example, a high loading of mannose was desired, so 10 g of mannose was added, dissolved, and allowed to react with the glycogen solution overnight. The next day, the solution was extensively ultrafiltered and concentrated against a 50 kD polyether sulfone membrane (MW cut-off 50 kD, Amicon stirred cell, Millipore, Inc., Billerica, Mass.) using deionized water, after which time the concentrated solution was placed into 50 kD equilibrium dialysis tubing (Spectrapor, VWR Scientific, Bridgeport, N.J.) and dialyzed against deionized water (100× volume turnover, 2 changes of deionized water daily for 5 days) to remove unreacted mannose from the mannosylated-glycogen. The retentate mannosylated-glycogen solution was lyophilized to yield a purified product in the form of a white powder.

Insulin-mannosylated glycogen was then synthesized by first dissolving 1 g of mannosylated glycogen in 12.5 ml of deionized water and 12.5 ml of dimethylsulfoxide (Sigma Aldrich, St. Louis, Mo.). Next, a 1.06 M solution of 1-cyano-4-dimethylaminopyridinium tetrafluoroborate (CDAP, Sigma Aldrich, St. Louis, Mo.) was prepared by mixing 125 mg of CDAP in 0.5 ml of dimethylsulfoxide, and the CDAP solution was cooled to just above 4 C. using an ice bath, so as not to freeze the CDAP solution. A third solution was made, consisting of 0.2 M triethylamine in deionized water, which was also cooled using an ice bath.

0.2 ml of the cooled liquid CDAP solution was then added dropwise to the mannosylated glycogen solution, and the mixture was allowed to stir for 1 minute. Next, 0.2 ml of a 200 mM triethylamine solution was added to the above mixture dropwise. After 2 minutes, the pH was adjusted to 9 using 0.3 M sodium hydroxide. Next, 15 ml of a 10 mg/ml insulin solution (human recombinant in 25 mM HEPES, pH 8.2, Sigma Aldrich, St. Louis, Mo.) was added dropwise to the glycogen solution and allowed to stir briefly. The pH was then adjusted to 9.15 using a 0.3 M sodium hydroxide solution or a 0.1 N hydrochloric acid solution as necessary. The final mixture was allowed to react overnight.

The insulin-mannosylated-glycogen conjugate was ultrafiltered against a 50 kD membrane using a stirred cell (Amicon, Millipore, Inc., Billerica, Mass.) using three volume turnovers, and the retentate solution was lyophilized. The lyophilized powder was dissolved in 1.0 M acetic acid and chromatographed using HPLC and a size exclusion column (Superdex 30 HiLoad 16/60 column, GE Healthcare, Piscataway, N.J.) with 1.0 M acetic acid as the mobile phase. The peak representing the high molecular weight insulin-mannosylated-glycogen was collected, and the fraction was lyophilized to obtain a pure powder. The powder could be redissolved and run on HPLC a second time if further purification was required. The insulin loading of the insulin-mannosylated-glycogen conjugate was determined by amino acid analysis, and the conjugate was assayed for impurities by SDS-PAGE.

Figure 24:
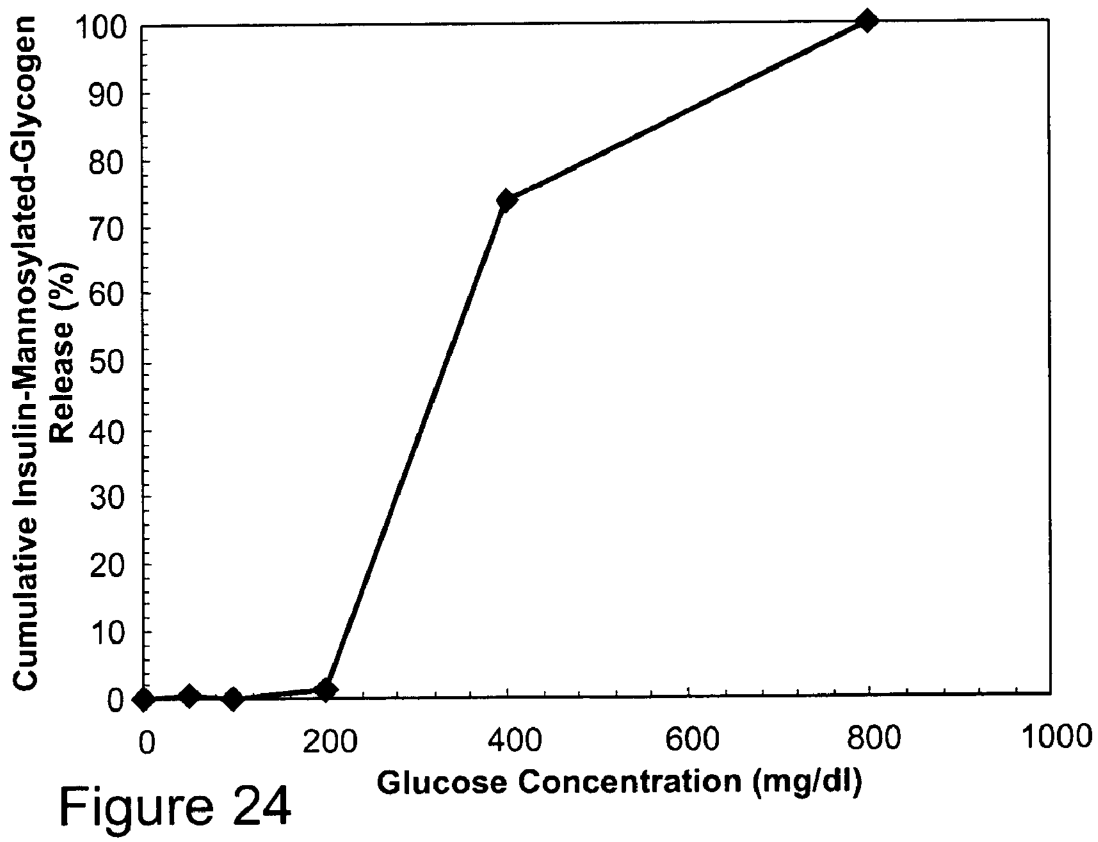
FIG. 24. Glucose setpoint as measured by methods in Example 12 for a drug delivery system comprised of insulin-mannosylated-glycogen and P64.

P64 was dissolved at 100 mg of Con A equivalents/ml in 20 mM pH 7 BES buffer containing 1 mM $MnCl_2$ and $CaCl_2$, and separately, insulin-mannosylated glycogen was dissolved at 50 mg/ml in 200 mM pH 7 BES buffer. 0.1 ml of the P64 solution was added to 0.1 ml of the insulin-mannosylated glycogen. After the gel formed, it was washed extensively in buffer and then run through a glucose set point assay as described in Example 12. FIG. 24 shows the cumulative amount of insulin-mannosylated glycogen released and demonstrates the type of glucose-responsive release profile obtained from these drug delivery systems. However, these materials have much less risk than those based on native Con A, because, based on our studies, the modified constructs are completely safe for use in vivo.

(H) Crosslinked Lectins

Example 40 describes experiments investigating the properties of crosslinked Con A compositions.

Example 41 describes the use of these crosslinked Con A compositions in a glucose-responsive insulin delivery system that uses an insulin-polysaccharide conjugate (i.e., see Example 39).

Example 40

Crosslinked Con A Compositions

Normally, non-mitogenic Con A compositions are incapable of forming precipitates with glycogen as measured by the methods of Example 7. This example describes the synthesis of a non-mitogenic modified Con A composition that is capable of forming precipitates with glycogen and is non-mitogenic as measured by the methods of Example 1. These compositions are obtained via a two step process, wherein the first step comprises the covalent crosslinking of native Con A subunits using a difunctional crosslinking agent. The second step involves modification of the crosslinked Con A subunits with pegylation reagents.

Briefly, 0.5 g of native Con A (Type V, Sigma Aldrich, St. Louis, Mo.) was dissolved in 50 ml of a 100 mM BES buffer, pH 7, containing 1.0 M NaCl and 1 mM $MnCl_2$ and 1 mM $CaCl_2$, and the mixture was cooled to 4° C. in an ice bath. After the Con A had dissolved, 0.188 g of the difunctional crosslinking agent ethylene glycol-bis(succinic acid-N-hydroxy-succinimide ester), Sigma Aldrich, St. Louis, Mo.) (EGBSAE) was added as a dry powder to the solution at 4 C. The solution was stirred at a rate high enough to create a well mixed suspension of the EGBSAE in solution without causing native Con A protein precipitation. The mixture was allowed to react and warm to room temperature overnight.

The following day, the entire reaction mixture was pipetted into two 50 ml capacity centrifuge tubes (Corning, VWR Scientific, Bridgeport, N.J.), and the mixture centrifuged at 3000×g for 10 minutes to remove any insoluble materials. The supernatant was kept and ultrafiltered against a 50 kD membrane in a stirred cell (Amicon, Millipore, Inc., Billerica, Mass.) against 100 mM BES buffer, pH 7, containing 1.0 M NaCl and 1 mM $MnCl_2$ and 1 mM $CaCl_2$ for at least three volume turnovers to remove any soluble unreacted crosslinking reagent. During the final ultrafiltration step, the solution concentration was made equal to the initial reaction volume of 50 ml and transferred into a fresh beaker. This solution contained the crosslinked native Con A protein, and this solution was cooled to 4 C.

In a separate beaker, 1.3 g of PEG-5k-SPA (Nektar Therapeutics, San Carlos, Calif.) was dissolved in 11.4 ml of 100 mM BES buffer, pH 7, containing 1.0 M NaCl and 1 mM $MnCl_2$ and 1 mM $CaCl_2$ and the solution was vortexed until all of the PEG reagent had dissolved. The entire PEG-5k-SPA solution was then pipetted dropwise into the stirred crosslinked Con A solution over the course of a few minutes, and the reaction mixture was allowed to react and warm to room temperature overnight.

The following day, the entire reaction mixture was pipetted into two 50 ml capacity centrifuge tubes (Corning, VWR Scientific, Bridgeport, N.J.), and the mixture centrifuged at 3000×g for 10 min to remove any insoluble materials. The supernatant was kept and ultrafiltered against a 50 kD membrane in a stirred cell (Amicon, Millipore, Inc., Billerica, Mass.) against 100 mM BES buffer, pH 7, containing 1.0 M NaCl and 1 mM $MnCl_2$ and 1 mM $CaCl_2$ for at least three volume turnovers to remove any soluble unreacted pegylation reagents or pegylation reaction byproducts. The pegylated crosslinked Con A solution was then lyophilized to obtain purified powder PXL-13-1.

Figure 25:
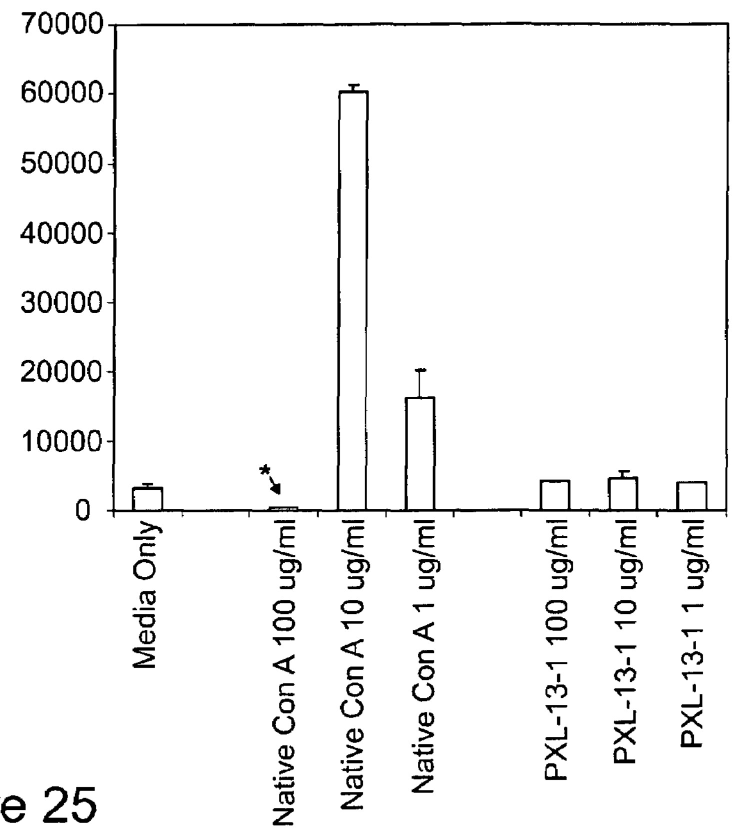
FIG. 25. In vitro mitogenicity assay analysis of crosslinked and pegylated Con A (PXL-13-1) versus cell media only and native Con A. The crosslinked and pegylated Con A is clearly non-mitogenic with respect to the controls. (*)-Native Con A at concentrations of 100 ug/ml is cytotoxic and gives a false non-mitogenic response. The cytotoxicity is measured via the methods of Example 2.
Figure 26:
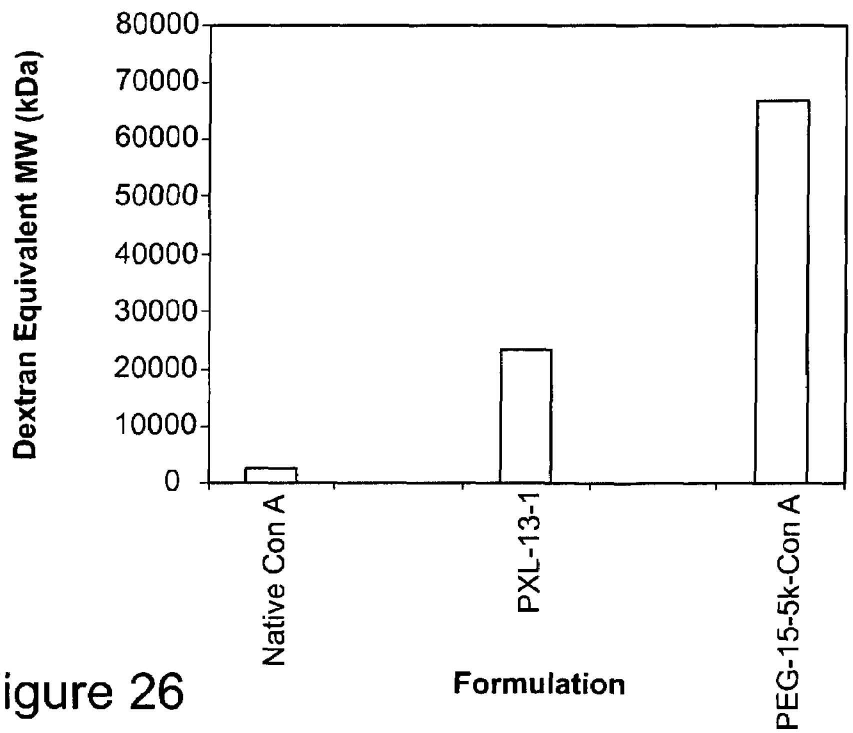
FIG. 26. Size exclusion HPLC data for native Con A, crosslinked and pegylated Con A (PXL-13-1 with PEG-15-5k), and PEG-15-5k-Con A (no crosslinking). In this case both the PXL-13-1 and PEG-15-Con A were reacted with the same amount of pegylation reagent, but the pre-crosslinked PXL-13-1 has less than half of the equivalent MW. Both PXL13-1 and PEG-15-Con A are also much larger than the dextran-equivalent MW of native Con A.
Figure 27:
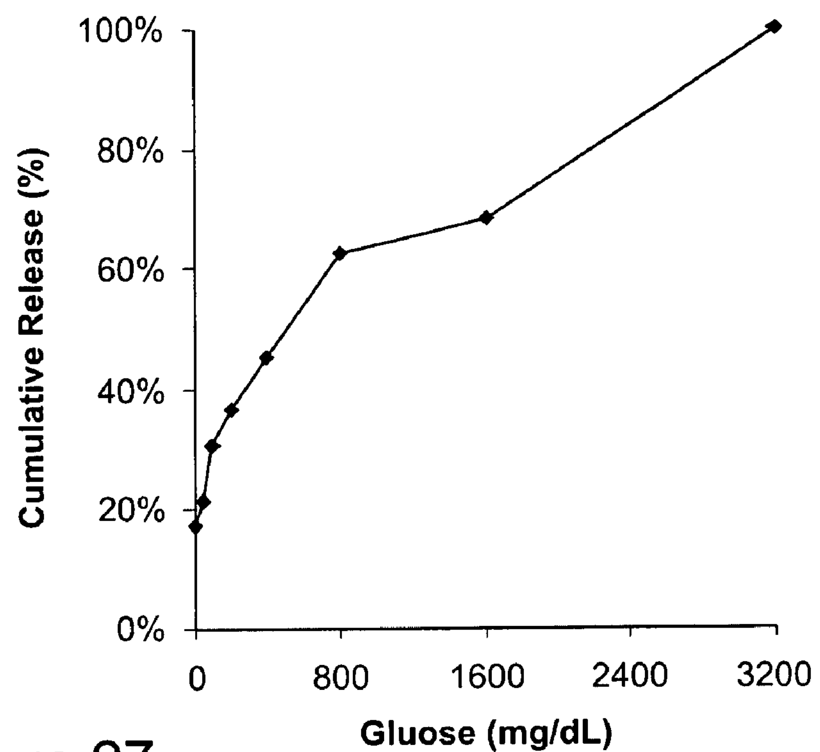
FIG. 27. Glucose setpoint as measured by methods in Example 12 for a drug delivery system comprised of insulin-glycogen and PXL-13-1.

A glycogen precipitation assay was carried out according to Example 7, and the OD490 value obtained was 1.04, indicating a preserved ability to precipitate with glycogen. In addition, the mitogenicity and size exclusion data of PXL-13-1 are shown in FIGS. 25 and 26. PXL-13-1 exhibits significantly reduced mitogenicity as compared to native Con A (see FIG. 25). While PXL-13-1 is more compact than the correspondingly non-crosslinked modified Con A it remains larger than native Con A (see FIG. 26).

Example 41

Glucose-Responsive Insulin Delivery System that Uses an Insulin-Polysaccharide Conjugate and Crosslinked Con A This example demonstrates how the crosslinked Con A of Example 40 can be used in a glucose-responsive drug delivery system such as the one described in U.S. Patent Publication No. 2004/0202719. In this example, the lectin is replaced with crosslinked and modified Con A composition PXL13-1 and the insulin-polysaccharide conjugate is replaced with an insulin-glycogen conjugate. However, the mechanism of glucose-responsive release is essentially the same, i.e., the gel formed between the two components is eroded with glucose such that it releases the insulin-polysaccharide conjugate from the surface in a glucose-responsive manner. The release is controlled primarily by competitive binding and not by diffusion as described in Example 38.

Insulin-glycogen was synthesized by first dissolving 1 g of glycogen (Type II Oyster, Sigma Aldrich, St. Louis, Mo.) in 12.5 ml of deionized water and 12.5 ml of dimethylsulfoxide (Sigma Aldrich, St. Louis, Mo.). Next, a 1.06 M solution of 1-cyano-4-dimethylaminopyridinium tetrafluoroborate (CDAP, Sigma Aldrich, St. Louis, Mo.) was prepared by mixing 125 mg of CDAP in 0.5 mL of dimethylsulfoxide, and the CDAP solution was cooled to just above 4 C. using an ice bath, so as not to freeze the CDAP solution. A third solution was made, consisting of 0.2 M triethylamine in deionized water, which was also cooled using an ice bath.

0.2 ml of the cooled liquid CDAP solution was then added dropwise to the glycogen solution, and the mixture was allowed to stir for 1 minutes. Next, 0.2 ml of a 200 mM triethylamine solution was added to the above mixture dropwise. After 2 minutes, the pH was adjusted to 9 using 0.3 M sodium hydroxide. Next, 15 ml of a 10 mg/ml insulin solution (human recombinant in 25 mM HEPES, pH 8.2, Sigma Aldrich, St. Louis, Mo.) was added dropwise to the glycogen solution and allowed to stir briefly. The pH was then adjusted to 9.15 using a 0.3 M sodium hydroxide solution or a 0.1 N hydrochloric acid solution as necessary. The final mixture was allowed to react overnight.

The insulin-glycogen conjugate was ultrafiltered against a 50 kD membrane using a stirred cell (Amicon, Millipore, Inc., Billerica, Mass.) using three volume turnovers, and the retentate solution was lyophilized. The lyophilized powder was dissolved in 1.0 M acetic acid and chromatographed using HPLC and a size exclusion column (Superdex 30 HiLoad 16/60 column, GE Healthcare, Piscataway, N.J.) with 1.0 M acetic acid as the mobile phase. The peak representing the high molecular weight insulin-glycogen was collected, and the fraction was lyophilized to obtain a pure powder. The powder could be redissolved and run on HPLC a second time if further purification was required. The insulin loading of the insulin-glycogen conjugate was determined by amino acid analysis, and the conjugate was assayed for impurities by SDS-PAGE.

PXL-13-1 was synthesized as described in Example 40 and was dissolved at 100 mg Con A equivalents/ml in 20 mM pH 7 BES buffer containing 1 mM $MnCl_2$ and 1 mM $CaCl_2$. Separately, insulin-glycogen was dissolved at 50 mg/ml in 200 mM pH 7 BES buffer. 0.2 ml of the PXL13-1 solution was added to 0.2 ml of the insulin-glycogen. After the gel formed, it was washed extensively in buffer and then run through a glucose set point assay as described in Example 12. FIG. 25 shows the cumulative amount of insulin-mannosylated glycogen released and demonstrates the type of glucose-responsive release profile obtained from these drug delivery systems. However, these materials have much less risk than those based on native Con A, because, based on our studies, the modified constructs are completely non-mitogenic as described in Example 40.

(J) In Vivo Biocompatibility

Example 42 compares the tissue biocompatibility of a gel formed by the interaction between glycogen and native Con A against a gel formed by the interaction between glycogen and an inventive modified Con A composition.

Example 42

Improved Biocompatibility In Vivo

Modified Con A composition P22 was used in this example. P22 was synthesized according to the generalized procedure described in Example 8 with PEG-SPA-2K at a PEG:Con A monomer molar ratio of 5, or a PEG:Con A mass ratio of 0.4 at 4 C. in a pH 8.5 borate buffer. Separately, P22 and Con A were dissolved in a 20 mM BES buffer at pH 7.0 containing 1 M NaCl and 1 mM $MnCl_2$ and $CaCl_2$ at a concentration of 100 mg/ml. 0.200 ml of the lectin solution (P22 or Con A) was then added to 0.200 ml of a 50 mg/ml glycogen solution in 200 mM BES buffer at pH 7 containing 1 mM $MnCl_2$ and $CaCl_2$. After the gels formed, they were centrifuged to the bottom of 1.5 ml conical centrifuge tubes and washed repeatedly with buffer. The gels were then placed into the barrel of a 1 ml syringe equipped with a 27G-½" needle and injected under the skin of six rats for each composition. The buffer was also injected under the skin of another six rats to serve as a negative control. On days 3, 10, and 38 of the experiment two rats from each group were sacrificed, after which the injection site was surgically removed, preserved in formalin solution, embedded in paraffin, sectioned and stained for histological examination.

Figure 28:
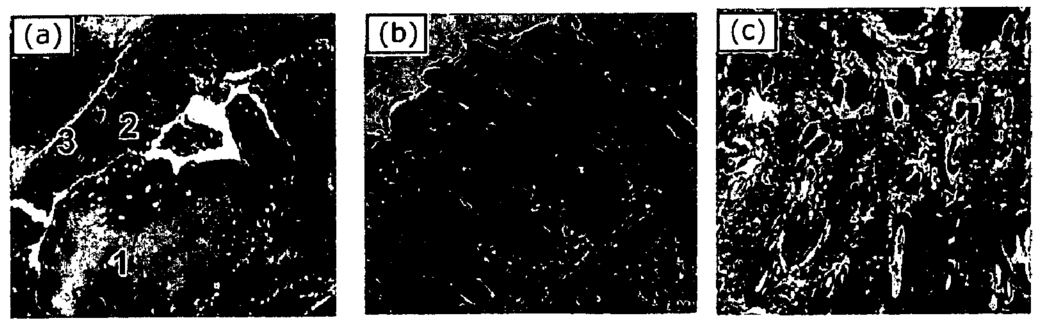
FIG. 28. Images of tissue samples extracted on Day 3 from the injection site. (a) Con A-gel: Injection site contains (1) an acellular area that is presumably part of the gel; (2) A large region of necrotic neutrophils; and (3) a thick capsule of proliferating fibroblasts, blood capillaries and some macrophages. (b) PEG-Con A-gel: Injection site appears normal with the exception that the muscle layer contained a mild to moderate population of lymphocytes and fewer plasma cells. (c) Saline: Injection site appears normal.

FIG. 28 shows representative skin sections from the injection sites for native Con A, P22, and saline injections. Image (a) is the native Con A gel; the injection site contains (1) an acellular area that is presumably part of the gel; (2) a large region of necrotic neutrophils; and (3) a thick capsule of proliferating fibroblasts, blood capillaries and some macrophages. Image (b) is the P22 gel; the injection site appears normal with the exception that the muscle layer contained a mild to moderate population of lymphocytes and fewer plasma cells. Image (c) is the saline sample; the injection site appears normal. Therefore, the modified Con A gel composition causes minimal inflammation and adverse reaction at the injection site as compared to native Con A gels that induce gross inflammation and cell death around the injection.

(K) Empirical Methods for Optimizing Lectin Modification

Example 43 describes an empirical method for identifying conditions that ensure uniform modification of a lectin monomer.

Example 44 describes an empirical method for identifying the optimal reagent for modification of a lectin composition.

Example 45 illustrates the methods of Example 44 by describing the use of dextran as an alternative to PEG for preparing modified Con A compositions.

Example 43

Optimizing Conditions for Lectin Modification

This example describes an empirical method for identifying conditions that ensure uniform modification of a lectin monomer. An amount of native lectin is dissolved in a pH 8.4 buffer solution. Separately, the same amounts of native lectin are mixed in other buffer solutions that cover a range of pH values (e.g., from pH 2 to pH 13, preferably from pH 6 to pH 10). The resulting mixtures are stirred until all components are dissolved. After dissolution, each mixture is split into three batches and the contents of each batch equilibrated at 4 C., room temperature, or 37 C. Several equal volumes from each buffer solution are then transferred into a collection of containers that are also equilibrated at the same three temperatures.

Separately, a pegylation agent is dissolved in water. This mixture is then slowly added dropwise using a pipette to each of the above solutions. The amount of pegylation agent is adjusted so that the molar ratio of pegylation agent to the number of amine groups on each monomer is varied across different containers for each buffer solution (e.g., from about 5 to 95%, preferably from about 20 to 85%). Table 16 lists various mitogenic lectins, including Con A, that may be subjected to this optimization procedure. For each lectin, there are a specific number of identical subunits containing a particular number of terminal —$NH_2$ lysine groups. This number is used to determine the amount of PEG reagent required for a desired degree of substitution. After addition, the resulting solutions are allowed to react slowly overnight.

TABLE 16

Exemplary mitogenic lectins suitable for use in this invention, including number of subunits, number of reactive groups available for modification, and the amount of PEG-5K or 2K required to achieve 100% substitution.

| Lectin | MW | number of subunits | Total Lysine Residues | Lysine/monomer | g PEG 5K/g lectin for complete substitution | g PEG 2K/g lectin for complete substitution |
|---|---|---|---|---|---|---|
| Concanavalin A | 104000 | 4 | 48 | 12 | 11.5 | 4.6 |
| Pisum sativum | 48000 | 2 | 22 | 11 | 11.5 | 4.6 |
| Lens culinaris | 49000 | 2 | 24 | 12 | 12.2 | 4.9 |
| Vicia faba | 50000 | 2 | 24 | 12 | 12.0 | 4.8 |
| Glycine max | 110000 | 4 | 28 | 7 | 6.4 | 2.5 |
| Wheat germ agglutinin | 36000 | 2 | 16 | 8 | 11.1 | 4.4 |

The following day concentrated acid or base is added to neutralize the pH to 7, and the solutions are placed inside dialysis bags that have a cut-off below the molecular weight of the lectin monomer. The solutions are extensively dialyzed against calcium and manganese ions in deionized water to remove unreacted pegylation agent and salts. The resulting solutions are then lyophilized to yield a series of modified lectin compositions. Modified lectin compositions that are substantially free of native lectin monomer are then identified by SDS-PAGE as described in Example 5. If no suitable composition is identified then testing is repeated with a different buffer, temperature and/or pegylation agent. Alternatively, the conditions that produced the composition with the lowest amount of native lectin monomer are identified and a second series of orthogonal experiments are repeated within a narrower range of conditions. Optionally, the absolute and relative concentrations of the lectin and pegylation agent are also varied across a series of samples.

In addition to SDS-PAGE, the glycogen precipitation assay may be performed as outlined in Example 7 to screen for potentially non-mitogenic compositions. Compositions still yielding an OD490 greater than about 0.5 are likely to be mitogenic according to the results of Example 27. Furthermore, the MAC value for the composition may be obtained as described in Example 6, and those compositions with values of less than 6 ug/ml are also likely to still be mitogenic according to the results in Example 26. Of course it is also possible to assay the mitogenicity of the modified lectin compositions directly using the methods of Example 1.

Example 44

Optimizing the Reagent for Lectin Modification

This example describes an empirical method for identifying a reagent that will ensure uniform modification of a lectin monomer. Suitable polymeric reagents include, but are not limited to, poly(ethylene glycol) polymers, poly(ethylene glycol)-poly(propylene glycol) block copolymers, polyureas, polysaccharides, polypeptides (e.g., polylysine), poly(ether-sulfone) polymers, poly(lactic acid) polymers, poly(lactic co-glycolic) acid polymers, poly(acrylic acid) polymers, and or random copolymers or block copolymer mixtures of any of the above. Because of the applications of these materials in aqueous systems, it is highly desirable that the polymer, functionalization chemistry, and resulting modified lectin composition remain moderately soluble in aqueous systems at physiologically relevant pH so as to be substantially soluble in the buffer, serum, or tissue of the in vitro or in vivo application. Also it is desirable to use a polymeric agent that does not cause undue protein denaturation, which would result in complete loss of lectin monosaccharide binding affinity as measured by the methods of Example 4.

In addition, protein sites of the native lectin monomer that may be available for reaction with the polymeric agent, include cysteines (thiols), carboxyl groups (C termini sites, glutamates), aromatic alcohols (tyrosines), amines (N termini sites, histidines, lysines, and asparagines), and other lectin monomer amino acid moieties. Other custom functionalities may also be introduced into the lectin monomer via site directed mutagenesis using methods that are well known to those skilled in the art (e.g., see Smith et al., *Protein Sci.* 14:64-73, 2005 and De Lorimier et al., *Protein Sci.* 11:2655-2675, 2002).

Each desired polymeric reagent and desired lectin monomer modification site will likely require a particular synthetic route to achieve functionalization of the native lectin monomer. FIG. 29 summarizes potential synthetic routes for several polymeric agent/lectin monomer site combinations. Others will be apparent to those skilled in the art.

The molecular weight and branch structure of the polymer will also likely influence the number of modifications per lectin monomer molecule in order to achieve a desired in vitro or in vivo effect. Generally as the degree of branching or the molecular weight of the polymeric agent molecular weight increases, fewer lectin monomer sites will need to be modified in order to achieve a desired effect due the increasing steric bulk of high molecular weight and highly branched polymers.

After a particular synthesis method is chosen, the temperature, pH, polymer molecular weight, concentrations of reagents, etc., can be optimized according to the methods of Example 43.

After lyophilizing the desired polymer-lectin compositions, the modified lectin compositions that are substantially free of native lectin monomer are identified by SDS-PAGE as described in Example 2. If no suitable composition is identified, then testing is repeated with a different buffer, temperature and/or polymeric reagent. Alternatively, the conditions that produced the composition with the lowest amount of native lectin monomer are identified and a second series of orthogonal experiments are repeated within a narrower range of conditions. Optionally, the absolute and relative concentrations of the lectin and polymer agent are also varied across a series of samples.

In addition to SDS-PAGE, the glycogen precipitation assay may be performed as outlined in Example 7 to screen for potentially non-mitogenic compositions. Compositions still yielding an OD490 greater than about 0.5 are likely to be mitogenic according to the results of Example 27. Furthermore, the MAC value for the composition may be obtained as described in Example 6, and those compositions with values of less than 6 ug/ml are also likely to still be mitogenic according to the results in Example 26. Of course it is also possible to assay the mitogenicity of the modified lectin compositions directly using the methods of Example 1.

Example 45

Dextranylated Con A

This example describes the preparation of a non-pegylated modified Con A composition that has reduced mitogenicity compared to native Con A. Instead of poly(ethylene glycol) as the polymeric reagent for reducing mitogenicity, dextran of molecular weight 40 kD (Sigma Aldrich, St. Louis, Mo.) was used.

Briefly, 2 separate aliquots of 2 g of dextran 40 kD were added to separate aliquots of 50 ml of deionized water, dissolved, and labeled batches A and B. The pH of Batch A was brought up to pH 10.7 using 3 M sodium hydroxide, after which 50 mg of cyanogen bromide (99.999% pure, Sigma Aldrich, St. Louis, Mo.) was added to the solution. The pH was maintained between 10.4 and 10.7 by using small aliquots of 3 M NaOH when necessary. After 20 minutes, another 50 mg of cyanogen bromide was added to the reaction mixture, and the pH was maintained for another 40 minutes.

Batch B received the same treatment as Batch A, except that B received 2×200 mg aliquots of cyanogens bromide during the experiment.

In a separate beaker, 400 mg of Type VI native Con A (Sigma Aldrich, St. Louis, Mo.) was dissolved in 40 ml of a pH 9.4, 100 mM sodium borate buffer. After all of the Con A had dissolved to give a clear solution, 11 ml of the Con A solution was added to Batch A dropwise over 1 minutes and the mixture was allowed to stir and react overnight. Likewise, 25 ml of the Con A solution was added to Batch B dropwise over 1 minute and the mixture was allowed to stir and react overnight.

Both Batch A and Batch B were purified extensively via ultrafitration using a 100 kD membrane using a stirred cell (Amicon, Millipore, Inc., Billerica, Mass.) against deionized water containing 1 mM $MnCl_2$ and 1 mM $CaCl_2$. After ten volume turnovers, the dextranylated-Con A solutions were lyophilized to obtain the purified dextranylated-Con A compositions.

Figure 30:
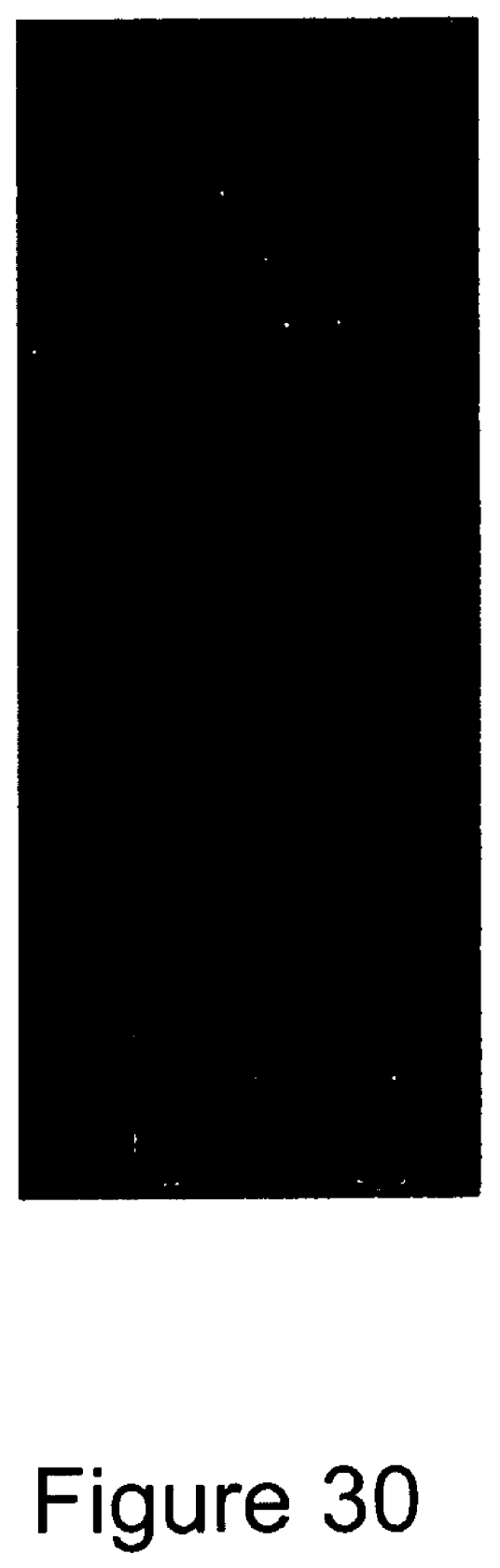
Figure 31:
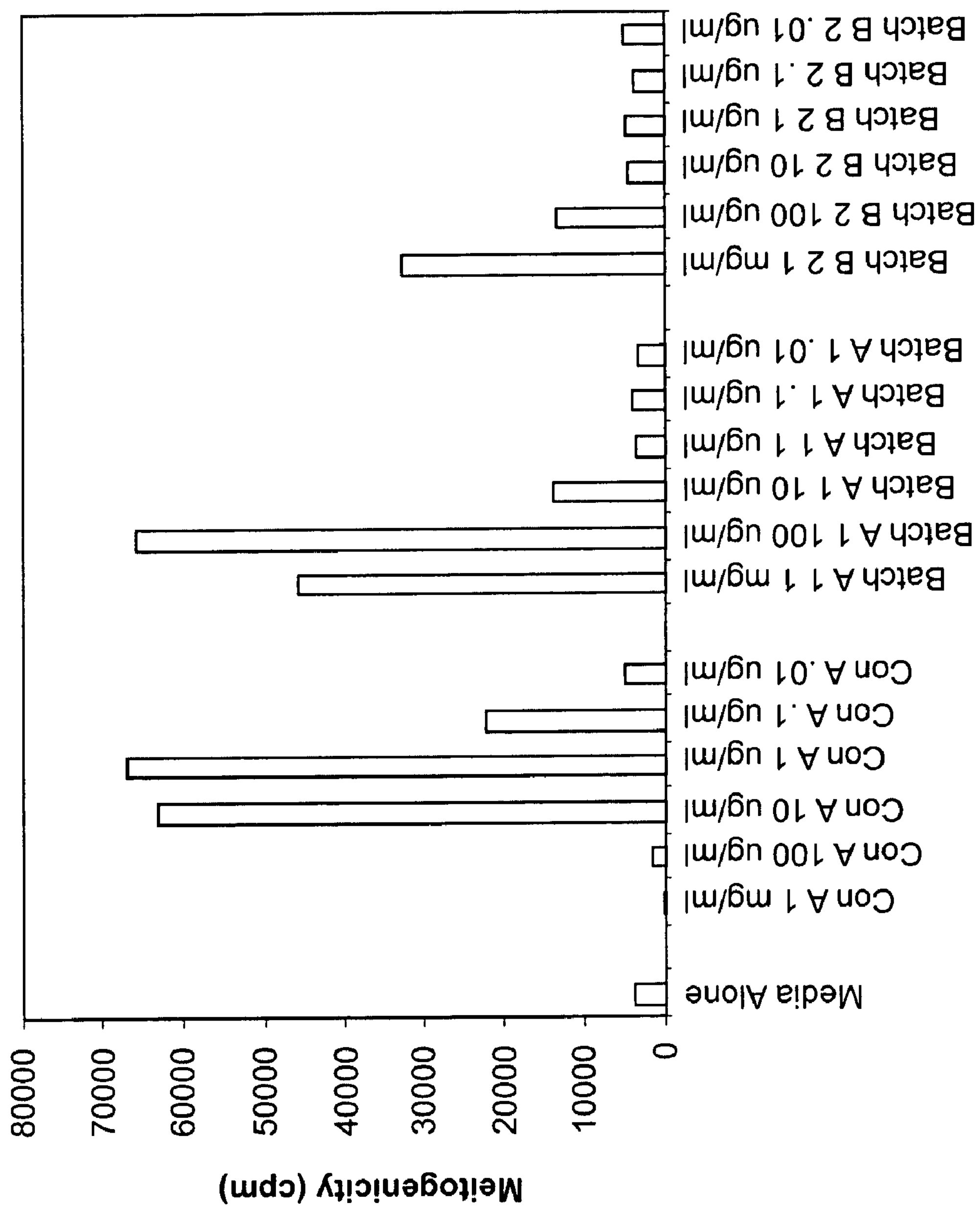
FIG. 31. Mitogenicity profiles for unmodified Con A, Batch A and Batch B.

SDS PAGE and mitogenicity results for the dextranylated Con A batches can be found in FIGS. 30 and 31. It can be seen from the SDS PAGE data that the higher degree of cyanogens bromide used with Batch B likely led to higher degrees of dextranylation of the Con A (compare lanes 4 and 5 of Figure EX 45-1). This likely explains why Batch B had the best mitogenicity profile as compared to Batch A and native Con A (see FIG. 31).

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

We claim:

1. A water-insoluble gelled matrix comprising:

therapeutic agent-mannose-containing polymer conjugates; and chemically modified lectins that bind the mannose-containing polymer portion of the conjugates and thereby cross-link the conjugates to form the water insoluble gelled matrix, wherein the matrix releases the conjugates from a surface of the matrix in a glucose-responsive manner and the chemically modified lectins are obtained by a method comprising the steps of:

providing a mitogenic lectin composition that includes a plurality of mitogenic lectins that bind glucose and mannose, wherein the mitogenic lectins are each comprised of one or more lectin subunits;

reacting the mitogenic lectins with a chemical compound to produce a chemically modified lectin composition, wherein the chemically modified lectin composition exhibits reduced T-cell mitogenicity as compared to the mitogenic lectin composition; and isolating a portion of the chemically modified lectin composition by glucose affinity chromatography, wherein the isolated portion exhibits reduced T-cell mitogenicity as compared to the chemically modified lectin composition.

2. The matrix of claim 1, wherein the glucose affinity chromatography uses a resin that comprises dextran.

3. The matrix of claim 1, wherein the mitogenic lectin composition includes Concanavalin A.

4. The matrix of claim 1, wherein the chemical compound is a pegylation agent.

5. The matrix of claim 4, wherein the pegylation agent is selected from the group consisting of N-hydroxysuccinimide activated poly(ethylene glycol), succinimidyl ester of poly (ethylene glycol) propionic acid, succinimidyl ester of poly (ethylene glycol) propionic acid butanoic acid, and succinimidyl ester of poly(ethylene glycol) alpha-methylbutanoate.

6. The matrix of claim 1, wherein the chemically modified lectins are incapable of precipitating glycogen comprised entirely of glucose units.

7. The matrix of claim 1, wherein the mannose-containing polymer is mannosylated-glycogen.

8. The matrix of claim 1, wherein the therapeutic agent comprises insulin.

9. The matrix of claim 8, wherein the unmodified lectins comprise Concanavalin A.

10. The matrix of claim 1, wherein the mitogenic lectin composition includes a mitogenic lectin that is multimeric and comprised of identical subunits in its native form.

11. The matrix of claim 10, wherein the mitogenic lectin is tetrameric in its native form and the mitogenic lectin composition comprises monomers, dimers, trimers, or tetramers of the mitogenic lectin, or any mixture thereof.

* * * * *